US012281100B2

(12) United States Patent
Helms et al.

(10) Patent No.: US 12,281,100 B2
(45) Date of Patent: Apr. 22, 2025

(54) RECYCLABLE AND RECONFIGURABLE HIGH-PERFORMANCE POLYMER NETWORKS AND USES THEREOF

(71) Applicant: The Regents of the University of California, Oakland, CA (US)

(72) Inventors: Brett A. Helms, Oakland, CA (US); Peter R. Christensen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1254 days.

(21) Appl. No.: 16/877,336

(22) Filed: May 18, 2020

(65) Prior Publication Data

US 2020/0283415 A1 Sep. 10, 2020

Related U.S. Application Data

(63) Continuation of application No. PCT/US2018/061681, filed on Nov. 16, 2018.

(60) Provisional application No. 62/587,148, filed on Nov. 16, 2017.

(51) Int. Cl.

| | |
|---|---|
| *C07D 403/06* | (2006.01) |
| *C07C 49/573* | (2006.01) |
| *C07C 225/24* | (2006.01) |
| *C07D 407/06* | (2006.01) |
| *C08G 73/02* | (2006.01) |
| *C08J 5/02* | (2006.01) |
| *C08J 9/04* | (2006.01) |
| *C08J 11/28* | (2006.01) |
| *C08K 11/00* | (2006.01) |
| *C08L 79/02* | (2006.01) |
| *C09J 179/02* | (2006.01) |
| *G10K 11/162* | (2006.01) |
| *G10K 11/18* | (2006.01) |
| *H01B 1/12* | (2006.01) |
| *H01B 3/30* | (2006.01) |

(52) U.S. Cl.
CPC .......... *C07D 403/06* (2013.01); *C07C 49/573* (2013.01); *C07C 225/24* (2013.01); *C07D 407/06* (2013.01); *C08G 73/0273* (2013.01); *C08J 5/02* (2013.01); *C08J 9/04* (2013.01); *C08J 11/28* (2013.01); *C08K 11/00* (2013.01); *C08L 79/02* (2013.01); *C09J 179/02* (2013.01); *G10K 11/162* (2013.01); *G10K 11/18* (2013.01); *H01B 1/124* (2013.01); *H01B 3/30* (2013.01); *C08J 2205/04* (2013.01); *C08J 2379/02* (2013.01); *C08L 2203/14* (2013.01)

(58) Field of Classification Search
CPC ........ C07D 403/06; C08G 73/02; C08L 79/02
See application file for complete search history.

(56) References Cited

U.S. PATENT DOCUMENTS

| | | | |
|---|---|---|---|
| 5,061,764 A | 10/1991 | Harris et al. | |
| 5,191,047 A | 3/1993 | Harris | |
| 6,765,089 B1 | 7/2004 | Toth et al. | |
| 9,453,099 B2 | 9/2016 | Zhang et al. | |

OTHER PUBLICATIONS

Kandambeth et al (Construction of Crystalline 2D Covalent Organic Frameworks with Remarkable Chemical (Acid/Base) Stability via a Combined Reversible and Irreversible Route, J. Am. Chem. Soc. 2012, 134, 19524-19527, published on Nov. 15, 2012.*
Rahimi et al., "Chemical recycling of waste plastics for new materials production", J. M. Nat. Rev. Chem. 1, 0046 (2017).
Helms et al., "Reaction: Polymer Chemistries Enabling Cradle-to-Cradle Life Cycles for Plastics.", Chem. 1, 816-818 (2016).
Otto et al., "Dynamic Combinatorial Chemistry" Chem. Rev. 106, 3652-3711 (2006).
Jin et al., "Recent advances in dynamic covalent chemistry", Chem. Soc. Rev. 42, 6634-6654 (2013).
Rowan et al., "Dynamic Covalent Chemistry", Angew. Chem. Int. Ed. 41, 898-952 (2002).
Montarnal et al. "Silica-Like Malleable Materials from Permanent Organic Networks" Science, 334, 965-968 (2011).
Fortman et al., "Mechanically Activated, Catalyst-Free Polyhydroxyurethane Vitrimers", J. Am. Chem. Soc. 137, 14019-14022 (2015).
Denissen et al., "Vinylogous Urethane Vitrimers", Adv. Funct. Mater. 25, 2451-2457 (2015).
Prutman et al., "Polylactide Vitrimers", ACS Macro Lett. 3, 607-610 (2014).
Rottger et al., "High-performance vitrimers from commodity thermoplastics through dioxaborolane metathesis", Science, 356, 62-65 (2017).
Billiet et al., "Triazolinediones enable ultrafast and reversible click chemistry for the design of dynamic polymer systems", Nat. Chem. 6, 815-821 (2014).
Diehl et al., "Click and chemically triggered declick reactionsthrough reversible amine and thiol coupling viaa conjugate acceptor", Nat. Chem. 8, 968-973 (2016).
Gratz et al., "Mechanochemical polymerization—controlling a polycondensation reaction between a diamine and a dialdehyde in a ball mill", RSC Adv., 6, 64799-64802 (2016).
International Search Report and Written Opinion for PCT/US18/61681, mailed on Feb. 1, 2019.
Third Party Observation received for PCT/US2018/061681, submitted on Mar. 8, 2020.

(Continued)

*Primary Examiner* — Gregory Listvoyb
(74) *Attorney, Agent, or Firm* — Kilpatrick Townsend & Stockton LLP

(57) ABSTRACT

The present invention relates to a composition of polymers comprising dynamic covalent diketoenamine bonds. This composition allows the formulation of polymeric materials with a wide range of architectures and properties, and further allows these materials to be recycled using thermal, chemical, or mechanical processes.

6 Claims, 30 Drawing Sheets

(56) References Cited

OTHER PUBLICATIONS

Taynton, "Development of Polyimine-Based Dynamic Covalent Networks: From Malleable Polymers to High-Performance Composites", Ph.D dissertation, University of Colorado (2015).

Loudon, Organic Chemistry (5th ed.), Greenwood Village, CO: Roberts and Company, pp. 926-930 (2009).

Nash et al., "Dde - A Selective Primary Amine Protecting Group: A Facile Solid Phase Synthetic Approach To Polyamine Conjugates", Tetrahedron Lett. 37, 2625-2628 (1996).

Kellam et al., "Solid Phase Applications of Dde and the Analogue Nde: Synthesis of Trypanothione Disulphide" Tetrahedron Lett. 38, 4849 (1997).

Kohout et al., "Mechanistic aspects of the direct C-acylation of cyclic 1,3-dioneswith various unactivated carboxylic acids" Tetrahedron, 71, 2698-2707 (2015).

* cited by examiner

H₂SO₄, 25 °C, 24 h

RECYCLABLE AND RECONFIGURABLE HIGH-PERFORMANCE POLYMER NETWORKS AND USES THEREOF

CROSS REFERENCE TO RELATED APPLICATIONS

This application claims priority as a continuation application to PCT International Patent Application No. PCT/US2018/061681, filed Nov. 16, 2018, which claims priority to U.S. Provisional Patent Application Ser. No. 62/587,148, filed Nov. 16, 2017, both of which are incorporated by reference in their entireties.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

FIELD OF THE INVENTION

The present invention is in the field of polymer networks.

BACKGROUND OF THE INVENTION

Polymers are typically the product of static covalent bond-forming reactions between monomers, yielding macromolecular materials with a wide range of useful properties but limited opportunities to recycle and reuse. Desirable is a platform allowing polymers to be reprocessed, recovering the monomers in their original form after end-of-use. Success would signal that sustainable cradle-to-cradle and closed-loop lifecycles for plastics are within reach. Here we present a new dynamic covalent bond—the diketoenamine—which allows for the preparation of linear, branched, and networked polymer architectures. Notably, poly(diketoenamine)s form spontaneously from a wide variety of triketone and aromatic and aliphatic amine monomers, yielding only water as a byproduct. Poly(diketoenamine)s are high-performance polymeric materials and can be de-polymerized from homogeneous or heterogeneous polymer waste to yield re-usable triketone monomers and amine monomers.

Of the ~100 million tons of plastic produced each year, less than 10% is recycled. (1, 2) The plastic waste that we do recycle is more likely to be incinerated rather than re-purposed. While incineration of plastic waste enables value recovery in the form of heat energy, this process only recovers a portion of the material value and adds significantly to atmospheric pollutants. Ideally, plastic materials should be designed in a closed loop, or circular fashion where materials with the same, or greater properties can be obtained at the end of a product's life.

Most polymers (e.g., polyolefins, styrenics, acrylics, etc.) are synthesized using kinetically controlled, irreversible bond-forming reactions. Not surprisingly, the implementation of irreversible bonds in polymers has made it both difficult and costly to recycle and re-purpose plastic materials. Conversely, dynamic covalent polymers are designed with the ability to exchange (i.e., interchange) certain types of chemical bonds among those present in the material. Particularly noteworthy are dynamic covalent polymers that undergo associative bond exchange reactions, e.g., via metathesis or addition-elimination schemes, the latter requiring excess nucleophile present. (3, 4, 5) For most known dynamic covalent bonds, associative exchange reactions are slow and thus require the use of a catalyst, which is undesirable for many applications. (6, 7, 8, 9, 10) Often, polymers synthesized with known dynamic covalent bonds have inferior mechanical properties to materials prepared using static covalent bonds. Furthermore, examples of de-polymerization for polymeric materials prepared from known dynamic covalent bonds are scant, inefficient, or impractical. (11, 12) Needed is a new dynamic covalent bonding motif that allows dynamic covalent polymers to be prepared with controlled architectures and properties without the use of a catalyst, while also allowing for recycling via recovery of the monomers in a usable form.

BRIEF SUMMARY OF THE INVENTION

The present invention pertains to the use of the diketoenamine bond (13, 14) to synthesize high performance dynamic covalent polymers that can be de-polymerized to regenerate pure monomer in a true, closed-loop, cradle-to-cradle process. Triketones are synthesized from carboxylic acids (or, in some cases, carboxylic acid halides) and 1,3-diones, and react with both aliphatic and aromatic amines enabling a very wide range of available polymer formulations with extensive variability in both electrophile and nucleophile. In the presence of excess amine, the diketoenamine bond exhibits catalyst-free associative bond exchange with extremely low activation energies, enabling rapid thermal processing of high $T_g$ materials. We show that diketoenamine polymers can be synthesized in a matter of minutes, e.g., using mechanical grinding, a low energy process that is both scalable and free of solvent and catalyst. Furthermore, we show that mixed diketoenamine polymer waste can be chemically de-polymerized at room temperature in acidified water to regenerate pure triketone monomers without additional purification, and regenerate pure amine monomers after neutralization using a basic ion-exchange resin.

The present invention provides for a composition of polymers comprising dynamic covalent diketoenamine bonds (FIG. 1 & FIG. 2). This composition allows the formulation of polymeric materials with a wide range of architectures and properties, and further allows these materials to be recycled using thermal, chemical, or mechanical processes.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
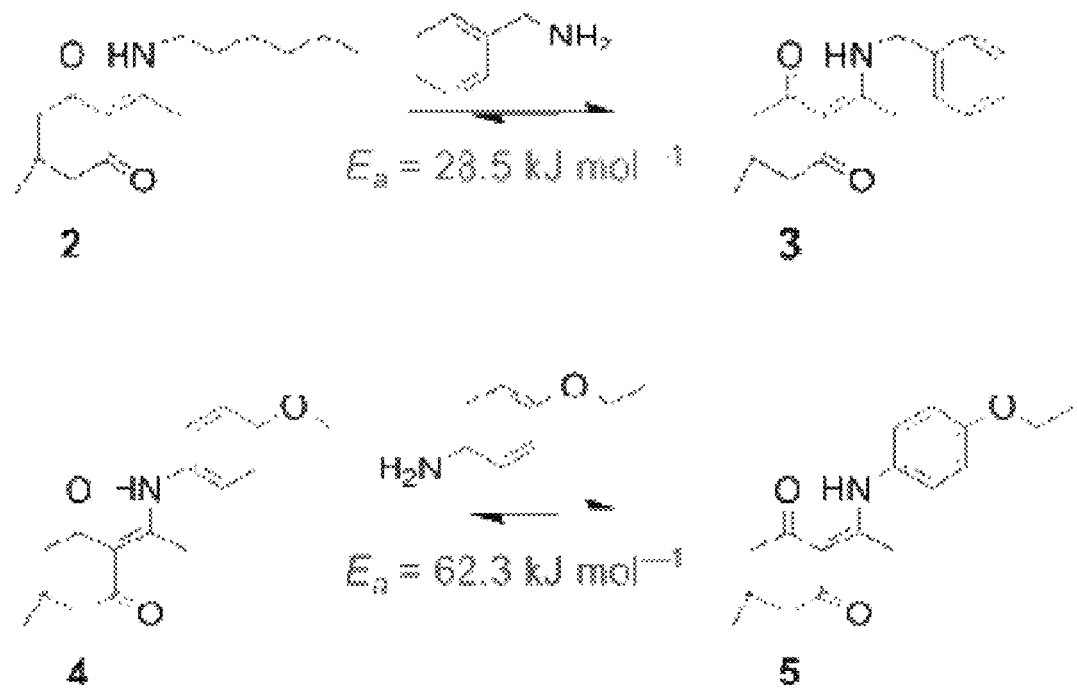
FIG. 1. Reactions featuring diketoenamine bonds.
Figure 2:
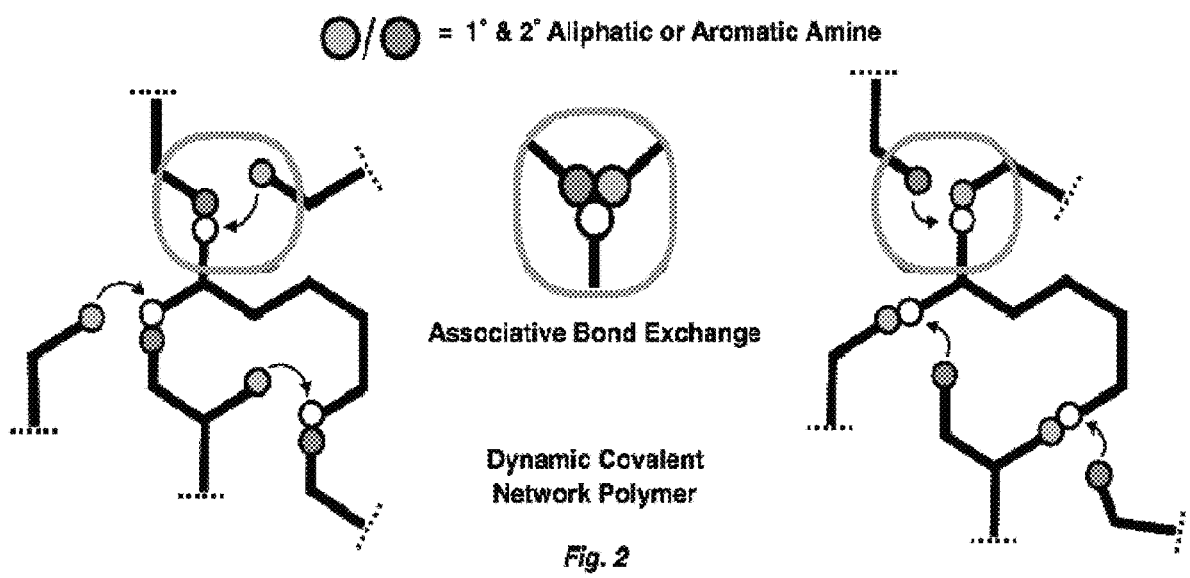
FIG. 2. A generalized reaction featuring associative bond formation and a dynamic covalent network polymer.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The present invention provides for a composition comprising a polymer, or polymer network, having at least one unit of the formula (I), (II), (III), (IV), (V), (VI), (VII), (VIII), (IX), (X), (XI), (XII), (XIII), (XIV), (XV), (XVI), (XVII), (XVIII), (XIX), and/or (XX), or a mixture thereof;

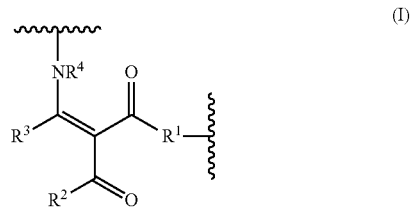

(I)

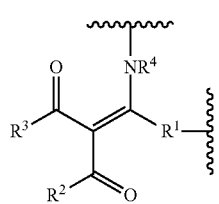
(II)
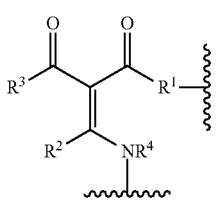
(III)
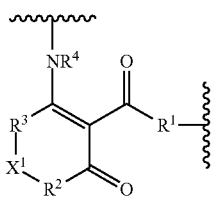
(IV)
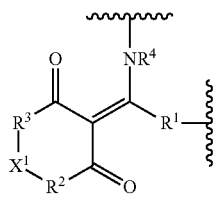
(V)
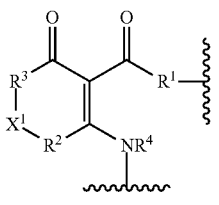
(VI)
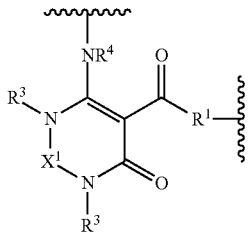
(VII)
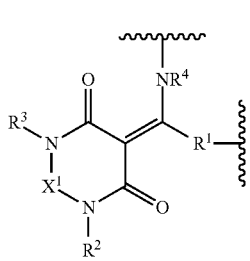
(VIII)
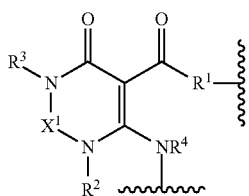
(IX)
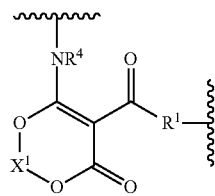
(X)
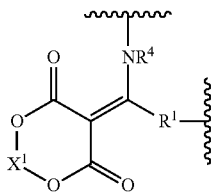
(XI)
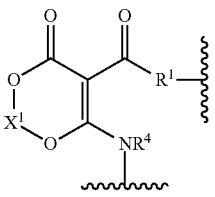
(XII)
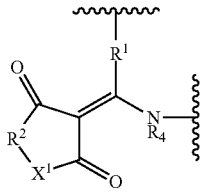
(XIII)
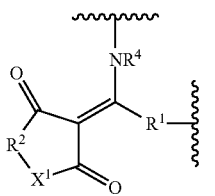
(XIV)
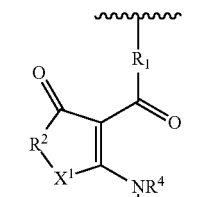
(XV)
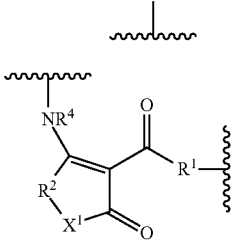
(XVI)

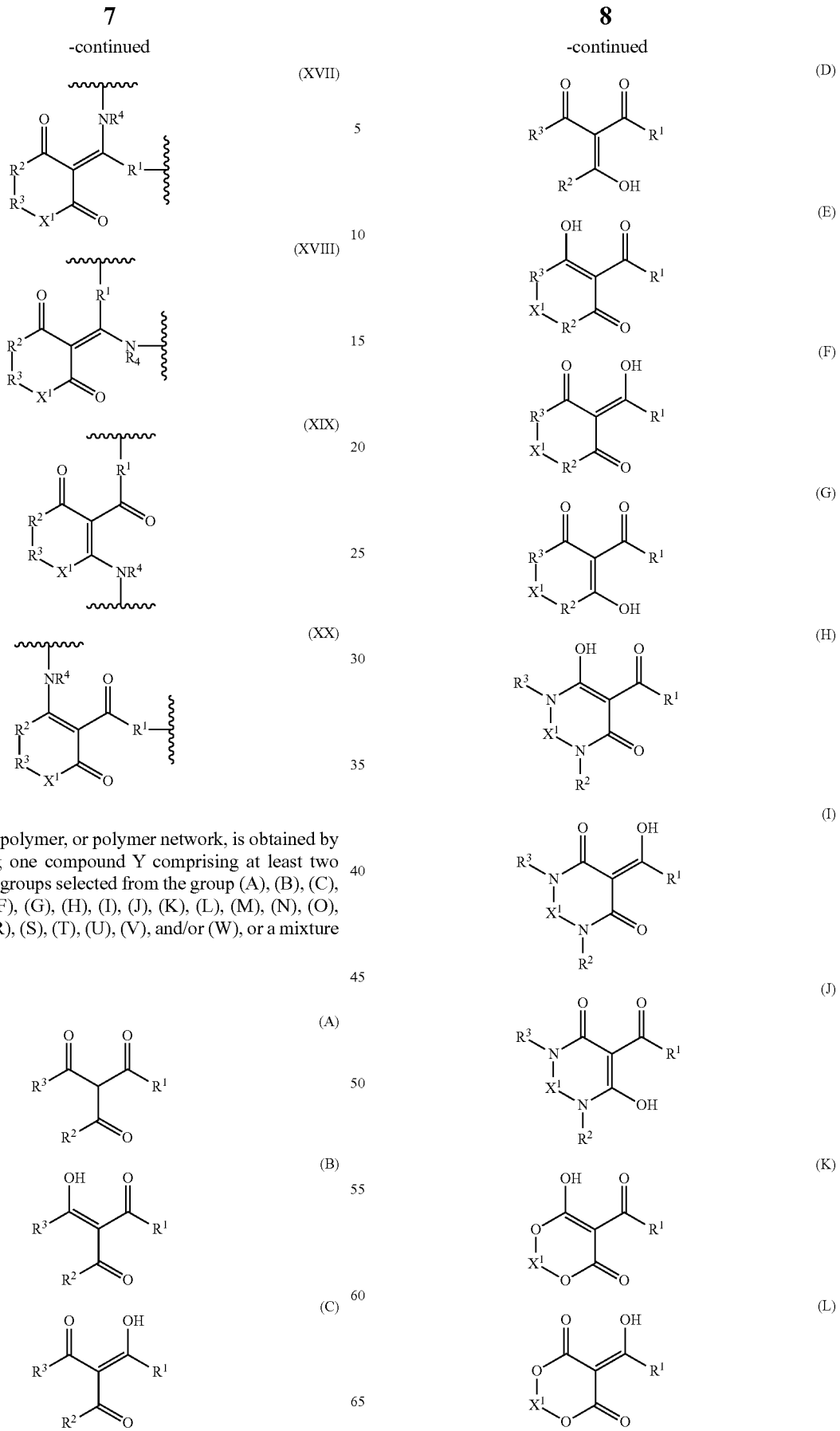
wherein said polymer, or polymer network, is obtained by connecting one compound Y comprising at least two functional groups selected from the group (A), (B), (C), (D), (E), (F), (G), (H), (I), (J), (K), (L), (M), (N), (O), (P), (Q), (R), (S), (T), (U), (V), and/or (W), or a mixture thereof;
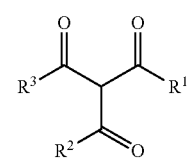
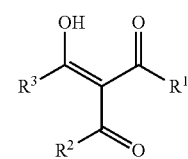
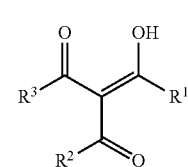

(M) 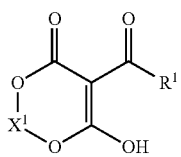

(N) 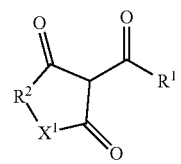

(O) 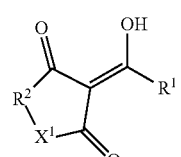

(P) 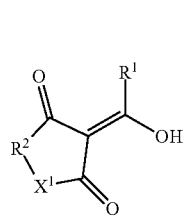

(Q) 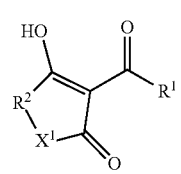

(R) 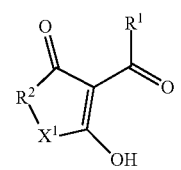

(S) 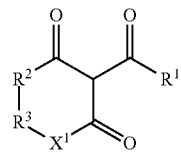

(T) 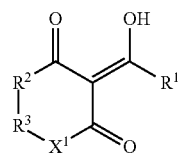

(U) 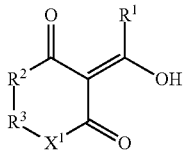

(V) 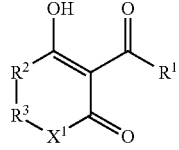

(W) 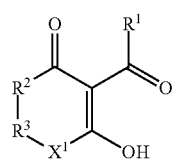

with at least one compound Z comprising at least two amine functional groups of the type —NH$_2$, —NHR$^4$, —NH$_3^+$ and/or —NHR$^4$R$^{5+}$ groups, or at least two functional groups that generates —NH$_2$, —NHR$^4$, —NH$_3^+$ and/or —NHR$^4$R$^{5+}$ in situ, or a mixture thereof;

wherein said amine is optionally (C$_{1-20}$)alkyl, (C$_{2-20}$)alkenyl; (C$_{2-20}$)alkynyl; (C$_{6-12}$)aryl, (C$_{3-8}$)cycloalkyl; (C$_{6-12}$)aryl(C$_{1-20}$)alkyl; (C$_{3-8}$)cycloalkyl(C$_{1-20}$)alkyl; hetero(C$_{1-20}$)alkyl; heterocyclyl; heterocyclyl(C$_{1-20}$)alkyl; heteroaryl; or heteroaryl(C$_{1-20}$)alkyl;

wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl, moiety, said heteroatoms being each independently a C, Si, chalcogenide (such as O, S, or Se), or a pnictide (such as N, or P);

wherein at least one carbon atom or heteroatom of said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl (C$_{1-20}$)alkyl; heterocyclyl(C$_{1-20}$)alkyl; and heteroaryl (C$_{1-20}$)alkyl; can optionally be oxidized to form at least one C=O, C=S, N=O, N=S, S=O or S(O)$_2$;

wherein said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and heteroaryl(C$_{1-20}$)alkyl; can be unsubstituted or substituted with one or more Z$^1$;

each Z$^1$ is independently selected from the group consisting of halogen; (C$_{1-20}$)alkyl; (C$_{2-20}$)alkenyl, (C$_{2-20}$) alkynyl, (C$_{6-12}$)aryl, (C$_{3-8}$)cycloalkyl, (C$_{6-12}$)aryl (C$_{1-20}$)alkyl, hetero(C$_{1-20}$)alkyl; heterocyclyl; heteroaryl; (C$_{3-8}$)cycloalkyl(C$_{6-12}$)alkyl; heterocyclyl (C$_{1-20}$)alkyl; heteroaryl(C$_{1-20}$)alkyl; halo(C$_{1-20}$)alkyl; halo(C$_{1-20}$)alkyloxy; —OR$^5$; —SR$^5$; —S(O)R$^4$; —S(O)$_2$R$^4$; —SO$_2$NR$^6$R$^7$; —NO$_2$; —NR$^5$C(O)R$^4$; —NR$^5$S(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$; and wherein the ratio R is less than, or equal to 1 (R≤1), where R=(sum(functionality of compound Y (F$_Y$)×number of moles of compound Y (N$_Y$))/(sum(functionality of compound Z (F$_Z$)×number of moles of all molecules of compound Z (N$_Z$)).

$$R = \frac{\sum F_Y N_Y}{\sum F_Z N_Z} \leq 1;$$

wherein $R_1$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide (such as O, S, or Se), or a pnictide (such as N, or P);

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S—O or S(O)$_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^6$R$^7$; nitro; —NR$^5$C(O)R$^4$; —NR$^5$(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$; and wherein $R^2$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide (such as O, S, or Se), or a pnictide (such as N, or P);

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or S(O)$_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$; and wherein $R^2$ and $R^3$ are optionally directly bonded together to form a, 5 membered cycloalkyl, heterocyclyl, or heteroaryl;

wherein $R^2$ and $R^3$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (preferably O, S, or Se), or a pnictide (preferably N, or P);

wherein each said heterocyclyl; or heteroaryl is independently optionally substituted with one or more $Z^2$ wherein each $Z^2$ is independently selected from the following group consisting of halogen; $(C_{1-20})$alkyl; $(C_{2-20})$alkenyl, $(C_{2-20})$alkynyl, $(C_{1-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-s})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^5$R$^6$; nitro; —NR$^5$C(O)R$^4$; —NR$^5$S(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$;

wherein $R^2$ and $R^1$ are optionally directly bonded together to form a, 5 membered cycloalkyl, heterocyclyl, or heteroaryl;

wherein $R^2$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Sc), or a pnictide (such as N, or P);

wherein $X^1$ and $R^2$ are optionally directly bonded together to form a, 5, 6, 7, or 8 membered heterocyclyl, or heteroaryl;

wherein $X^1$ and $R^3$ are optionally directly bonded together to form a, 5, 6, 7, or 8 membered cycloalkyl, heterocyclyl, or heteroaryl;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-2})$alkyl; halo$(C_{1-20})$alkyloxy; —OR$^5$; —SR$^5$; —S(O)R$^4$; —S(O)$_2$R$^4$; —SO$_2$NR$^5$R$^6$; nitro; —NR$^5$C(O)R$^4$; —NR$^5$S(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$;

wherein $R_3$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide (such as O, S, or Se), or a pnictide (such as N, or P);

wherein at least one carbon atom or heteroatom of said $(C_{1-20})$alkyl, $(C_{2-20})$alkenyl, $(C_{2-20})$alkynyl, $(C_{6-12})$aryl, $(C_3)$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is optionally oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is unsubstituted or substituted with one or more Z;

wherein each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{1-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^5R^7$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$; and wherein $R^3$ and $R^1$ are optionally directly bonded together to form a, 5 membered cycloalkyl, heterocyclyl, or heteroaryl;

wherein $R^3$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Se), or a pnictide (such as N, or P);

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$ wherein $R^3$ is linked to $R^1$ with a linker $X^1$ to form a 4, 5, 6, or 7 membered cycloalkyl, heterocyclyl, or heteroaryl;

wherein $X^1$ within said cycloalkyl, heterocyclyl, or heteroaryl is independently selected from the group consisting of C, Si, chalcogenide (preferably O, S, or Se), or a pnictide (preferably N, or P);

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$;

each $R^4$ is independently selected from the group consisting of hydrogen, $C_{(1-20)}$alkyl, $C_{(2-20)}$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{6-12})$aryl$(C_{1-20})$alkyl, heterocyclyl$(C_{1-20})$alkyl; heteroaryl$(C_{1-20})$alkyl, optionally comprise one or more heteroatoms in the alkyl, alkenyl or alkynyl moiety, said heteroatoms being each independently selected from O, S and N; and wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; is optionally oxidized to form at least one C=O, C=S, N=O, N=S, S=O or $S(O)_2$;

each $R^5$ is independently selected from the group consisting of hydrogen, $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{6-12})$aryl$(C_{1-20})$alkyl, heterocyclyl$(C_{1-20})$alkyl; heteroaryl$(C_{1-20})$alkyl, optionally comprise one or more heteroatoms in the alkyl, alkenyl or alkynyl moiety, said heteroatoms being each independently selected from O, S and N; and wherein at least one carbon atom or heteroatom of said $(C_{1-20})$alkyl, $(C_{2-20})$alkenyl, $(C_{2-20})$alkynyl, $(C_{6-12})$aryl, $(C_{3-s})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; is optionally oxidized to form at least one C=O, C=S, N=O, N=S, S=O or $S(O)_2$;

each $R^6$ and $R^7$ is independently selected from the group consisting of hydrogen; $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide (such as O, S, or Se), or a pnictide (such as N, or P);

and wherein at least one carbon atom or heteroatom of said $(C_{1-20})$alkyl, $(C_{2-20})$alkenyl, $(C_{2-20})$alkynyl, $(C_{1-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; is optionally oxidized to form at least one C=O, C=S, N=O, N=S, S=O or $S(O)_2$;

or wherein $R^6$ and $R^7$ together with the atom to which they are attached form a 5-, 6-, or 7-membered heterocyclyl.

The present invention provides for a method for synthesizing a polymer from one or more precursors in one or more solvents, said method comprising:

(a) dissolving, dispersing, or suspending one or more precursors individually in the same solvent, or individually in different and/or separate solvents, optionally with one or more surfactants;

(b) optionally heating the solvent or one or more solvents of the different and/or separate solvents;

(c) mixed the solvent comprising the one or more precursors together to form a polymer;

wherein said polymer is the composition of the present invention.

The present invention provides for a method for synthesizing a polymer by melting one or more solid precursors, said method comprising:
(a) melting one or more precursors together to form a polymer, wherein at least one precursor is solid prior to melting;
(b) optionally mixing the one or more precursors are solids prior to, during, and/or subsequent to the melting step, or melting the precursors which are solid are optionally first melted individually then mixed together to form a polymer;
wherein optionally the melting of the one or more precursors is in a single or twin screw compound extrusion device;
wherein said polymer is the composition of the present invention.

The present invention provides for a method for synthesizing a polymer from one or more precursors using mechanical grinding, said method comprising:
mixing one or more said precursors together in a shaking or rotating chamber to form a polymer;
wherein said shaking or rotating chamber is optionally a ball mill,
wherein optionally said shaking or rotating chamber contains a grinding medium;
wherein said grinding medium optionally comprises of one or several sizes of spheres or rods made of metallic, composite, ceramic, or polymer materials;
wherein said precursors are optionally dissolved in a solvent prior to mechanical grinding in said rotating chamber, also optionally called a ball mill;
wherein said precursors are optionally mixed together in a solvent during mechanical grinding;
wherein if one or more precursors are solids, precursors are optionally melted together before mixing;
wherein the duration of mixing of precursors within said shaking or rotating chamber, optionally with said grinding medium, is used to control the extent of polymerization;
wherein the duration of mixing of said precursors within said shaking or rotating chamber is used to control polymer properties;
wherein said polymer properties may optionally include the glass transition temperature ($T_g$), polymer solubility, modulus, tensile strength, polymer color, polymer toughness, polymer rigidity.
wherein said polymer is the composition of the present invention.

The present invention provides for a polymer alloy comprising a mixture or two or more polymers;
wherein one or more of said polymers is the composition of the present invention;
wherein at least of the two or more polymers optionally comprises one or more of the following:
polyurethane, polyurea, epoxy, phenolic resin, polyolefin, silicone, rubber, polyacrylate, polymethacrylate, polycyanoacrylate, polyester, polycarbonate, polyimide, polyamide, vitrimer, poly(vinylogous amide), poly(vinylogous urethane), and/or thermoplastic elastomers.

The present invention provides for a method of obtaining a polymer alloy using one or more solvents, said method comprising:
mixing one or more polymers together in one or more solvents to form a polymer alloy of the present invention.

The present invention provides for a method of obtaining a polymer alloy by compound extrusion, said method comprising:
melting one or more polymers together to form a polymer alloy of the present invention;
wherein optionally the mixing takes place in a compound single or twin screw extruder;

The present invention provides for a method of obtaining a polymer alloy by mechanical grinding, said method comprising:
mixing one or more polymers together in a shaking or rotating chamber to form a polymer alloy of the present invention;
wherein said shaking or rotating chamber is optionally a ball mill;
wherein said shaking or rotating chamber optionally contains a grinding medium;
wherein said grinding medium optionally comprises of one or more, or several, metallic or ceramic spheres or rods;
wherein one or more of said polymers are optionally dissolved in a solvent or melted together prior to mixing in said rotating chamber;
wherein the duration of mixing within said shaking or rotating chamber is used to control the properties of the polymer alloy formed.

The present invention provides for a composite material comprising a polymer and a filler material,
wherein said polymer is of the composition of the present invention, or is a polymer alloy of the present invention;
wherein said filler material is optionally a unit having the formula (I), (II), (III), (IV), (V), (VI), (VII), (VIII), (IX), (X), (XI), (XII), (XIII), (XIV), (XV), (XVI), (XVII), (XVIII), (XIX), and/or (XX) as described herein, or a polymer alloy as described herein, or
one or several selected from the following:
flame-retardant materials, woven or non-woven carbon fibers, woven or non-woven polyaramid fibers, woven or non-woven glass fibers, carbon black, carbon nanotubes, graphene, diamondoids, aluminum, steel, stainless steel, iron, zinc, titanium, silicon carbide, boron nitride, metal oxide, metal pnictides, metal chalcogenides, metal halides, transition metal dichalcogenides, metal alloys, MXenes, vitrimers, zeolites, metal-organic frameworks, covalent organic frameworks, alumina, silica, and/or silicate clays;
wherein said flame-retardant materials is a brominated compound, a chlorinated compound, a nitrogen-containing compound, a phosphorous-containing compound, a hydrated metal oxide such as hydrated aluminum oxide or hydrated magnesium oxide, a metal oxide such as antimony trioxide;
wherein said silicate clays is laponite, sumecton, monomorillonite (also known as bentonite), sodium fluorohectorite, or sodium tetrasilicic mica.
wherein said composite material optionally comprises a coloring agent, also called a dye or pigment.

The present invention provides for an adhesive material, comprising:
a polymer, and a polymer alloy and/or a composite material;
wherein said polymer is the composition of the present invention;

wherein said polymer alloy is as described herein;
wherein said composite material is as described herein.

The present invention provides for a bonded assembly, comprising:
two or more substrates bonded together with the adhesive material of the present invention;
wherein at least one or each substrate comprises one or more of the following: plastic, metal, ceramic, glass, composite, and/or wood.

The present invention provides for a method for extruding a polymer, said method comprising:
processing, such as extruding, one or more polymers of the present invention using a single or dual screw melt extrusion apparatus;
wherein one of said polymers is optionally a polymer alloy described herein;
wherein one of said polymers is optionally a composite material described herein;
wherein one of said polymers is optionally an adhesive material described herein.

The present invention provides for a method for shaping a polymer into a pellet, said method comprising:
processing or extruding a polymer is optionally first extruded described herein;
wherein said polymer is the composition of the present invention;
wherein said polymer is optionally a polymer alloy described herein;
wherein said polymer is optionally a composite described herein;
wherein said polymer is optionally an adhesive described herein.

The present invention provides for a polymer fiber having a diameter, width or thickness, or average thereof, ranging from about 0.5 nm to about 1.0 mm, and a length ranging from about 5 nm to up to about 5000 meters;
wherein said polymer is the composition of the present invention;
wherein said polymer is optionally a polymer alloy described herein;
wherein said polymer is optionally a composite described herein;
wherein said polymer is optionally an adhesive described herein.

The present invention provides for a porous material comprising a polymer and having one or more pores with pore sizes ranging from about 0.5 nm to about 5000 nm;
wherein said porous material (optionally a sorbent) is optionally modified to bind small molecules;
wherein said porous material (optionally a sorbent) optionally binds small molecules without modification;
wherein said porous material (optionally called a membrane) may optionally allow specific molecules, ions, solids, gases and/or liquids to transport into and/or through said porous material;
wherein said polymer is the composition of the present invention;
wherein said polymer is optionally a polymer alloy described herein;
wherein said polymer is optionally a composite described herein;
wherein said polymer is optionally an adhesive described herein.

The present invention provides for a foam comprising a polymer, a polymer alloy, a composite, an adhesive and/or a porous material, a polymer fiber that is optionally combined with one or several additives;
wherein said foam may optionally have a density of from about 0.1 to about 10 pounds per cubic foot (PCF).
wherein said polymer is the composition of the present invention;
wherein said polymer alloy is described herein;
wherein said composite material is described herein;
wherein said adhesive material is described herein;
wherein said polymer fiber is described herein;
wherein said porous material is described herein;
wherein said additive optionally is a blowing agent, a surfactant, a plasticizer, a coloring agent (also called a dye, also called a pigment), a flame retardant, a catalyst, a polymer, a poly-alcohol (also called a polyol), PTFE, and/or a polyolefin wax.

The present invention provides for a method whereby a foam is synthesized, said method comprising:
mixing compound(s) Y and compound(s) Z, as described in the composition of the present invention, with one or more additives to form a polymer;
wherein compound(s) Y and compound(s) Z have the ratio R described herein;
wherein said additives optionally comprise one or more polymer alloys, composite material, adhesive material, or any other composition described herein.

The present invention provides for an emulsion comprising a suspension of a material in a solvent, where the material is optionally a polymer, a polymer alloy, a composite, and/or an adhesive that is optionally combined with one or several additives;
wherein said emulsion may optionally have a solids content of from about 0.01% to about 80% on a per weight basis with respect to the solvent.
wherein said polymer is optionally of the composition;
wherein said polymer alloy is as described herein;
wherein said composite is as described herein;
wherein said adhesive is as described herein;
wherein said additives may optionally include, a blowing agent, a surfactant, a plasticizer, a coloring agent (also called a dye, also called a pigment), a flame retardant, a catalyst, a polymer, a poly-alcohol (also called a polyol), PTFE, and/or a polyolefin wax;
wherein the solvent is optionally water, an alcohol, and/or an organic solvent.

The present invention provides for a conductive material capable of conducting photons (light), phonons, electrons, holes, spin, ions, excitons, and/or acoustic waves (sound), said conductive material comprising a polymer, and optionally a porous material, a polymer fiber, a polymer alloy, an adhesive material, a composite material, and/or a foam that is optionally combined with one or several additives;
wherein said polymer is of the composition of the present invention;
wherein said polymer alloy as described herein;
wherein said composite material as described herein;
wherein said adhesive material as described herein;
wherein said adhesive is specifically formulated to maintain integrity when bonding two or more substrates with different coefficients of thermal expansion;
wherein said additives optionally includes electrical and/or chemical dopants added to control the conductivity of said conductive material.

The present invention provides for an insulating material having low conductivity to photons (light), phonons, electrons, holes, spin, ions, excitons, and/or acoustic waves (sound); said insulating material comprising a polymer, and optionally a porous material, a polymer fiber, a polymer alloy, an adhesive material, a composite material, and/or a foam that is optionally combined with one or several additives;

wherein said polymer is of the composition of the present invention;

wherein said polymer alloy as described herein;

wherein said composite material as described herein;

wherein said adhesive material as described herein;

wherein said additives may optionally include additives added to control the conductivity of said insulating material.

The present invention provides for a method for recycling a polymer or mixture of polymers, said method comprising:

depolymerizing a polymer or mixture of polymers with an excess of amine containing at least one of the type $R^8$—$NH_2$, $R^8$—$NHR^4$, $R^8$—$NH_3^+$ and/or $R^8$—$NHR^4R^{5+}$ groups, or at least one functional group that generates $R^8$—$NH_2$, $R^8$—$NHR^4$, $R^8$—$NH_3^+$ and/or $R^8$—$NHR^4R^{5+}$, in a composition of the present invention;

wherein said polymer or mixture of polymers is optionally depolymerized by hydrolysis in the presence an acid or a mixture of acids selected from, but not limited to, HCl, $H_2SO_4$, $H_3PO_4$, p-toluenesulfonic acid, methane sulfonic acid, trifluoroacetic acid, trifluoromethanesulfonic acid;

wherein said polymer or mixture of polymers is optionally depolymerized by hydrolysis in the presence an acid or a mixture of acids selected from, but not limited to, HCl, $H_2SO_4$, $H_3PO_4$, p-toluenesulfonic acid, methane sulfonic acid, trifluoroacetic acid, trifluoromethanesulfonic acid, alongside the presence of an amine containing at least one of the type $R^8$—$NH_2$, $R^8$—$NHR^4$, $R^8$—$NH_3^+$ and/or $R^8$—$NHR^4R^{5+}$ groups, or at least one functional group that generates $R^8$—$NH_2$, $R^8$—$NHR^4$, $R^8$—$NH_3^+$ and/or $R^8$—$NHR^4R^{5+}$;

wherein said polymer or mixture of polymers optionally contains at least one polymer of the composition (I), (II), (III), (IV), (V), (VI), (VII), (VIII), (IX), (X), (XI), (XII), (XIII), (XIV), (XV), (XVI), (XVII), (XVIII), (XIX), and/or (XX) as described herein;

wherein said polymer or mixture of polymers optionally comprises at least one polymer alloy as described herein;

wherein said polymer or mixture of polymers optionally comprises at least one composite as described herein;

wherein said polymer or mixture of polymers my optionally comprises at least one adhesive as described herein.

wherein $R^8$ is hydrogen or is selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, said heteroatoms being each independently a C, Si, chalcogenide (such as O, S, or Se), or a pnictide (such as N, or P);

and wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; can be oxidized to form at least one C=O, C=S, N=O, N=S, S=O or $S(O)_2$;

Activation Energies for Associative Bond Interchange Reactions in Diketoenamines The activation energy for diketoenamine bond exchange was estimated by monitoring the rate of exchange at different temperatures between an alkyl or aryl diketoenamine in the presence of excess (respectively) alkyl or aryl amine. Impressively, alkyl-alkyl exchange occurs at room temperature. The $E_a$ for alkyl-alkyl exchange was found to be 27 (±0.9) kJ mol$^{-1}$ and 63 (±2) kJ mol$^{-1}$ for aryl-aryl exchange.

Rates for both alkyl-alkyl (FIG. 3) and aryl-aryl (FIG. 4) exchange were measured using $^1$H NMR spectroscopy. Two identical mixtures of diketoenamine (2 for alkyl exchange kinetics; 4 for aniline exchange), an internal standard, and 1,2-dichlorobenzene-$d_4$ as a high boiling solvent were placed in a preheated oil bath and run in parallel. Excess amine (5 eq.) was added at once to each reaction and aliquots were taken at specified time intervals and analyzed by $^1$H NMR spectroscopy in CDCl$_3$. Reaction rates were calculated by monitoring the disappearance of the starting diketoenamine referenced to the internal standard.

Reaction Specific Details

Figure 3:
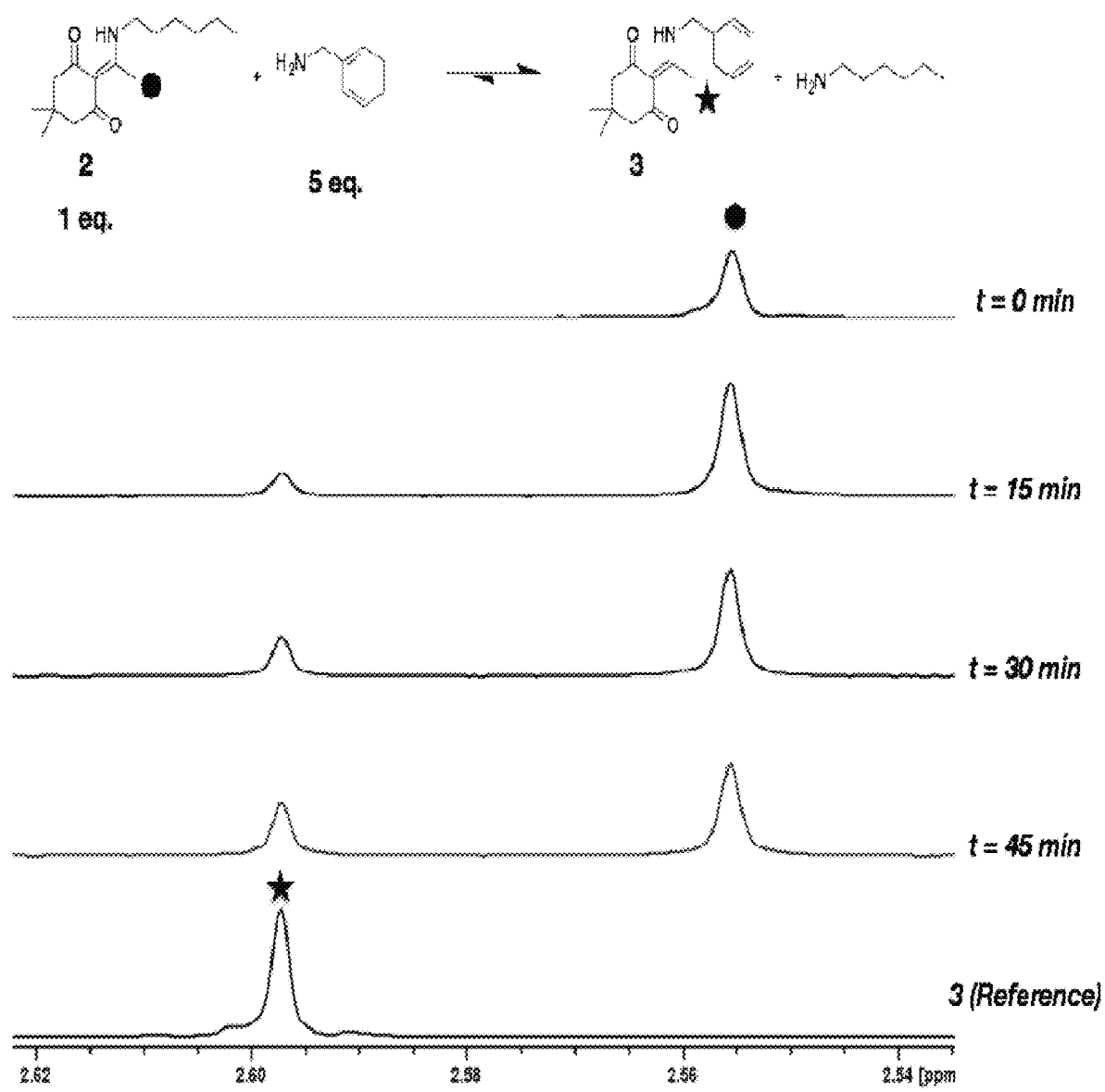
FIG. 3. Rate for alkyl-alkyl exchange measured using $^1$H NMR spectroscopy.
Figure 5:
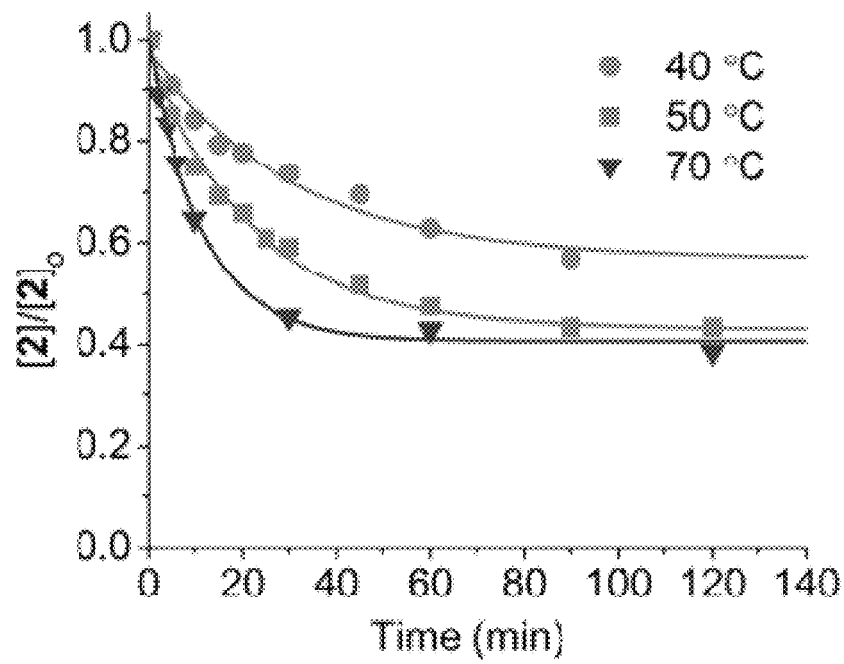
FIG. 5. Graph showing rate of alkyl-alkyl amine exchange.

Alkyl-Alkyl Amine Exchange (FIG. 3 & FIG. 5)

Two 4 mL vials containing diketoenamine 2 (25.0 mg, 0.94 mmol, 1 eq.), dimethylacetamide (7 µL, 0.09 mmol) as an internal standard, and 1,2-dichlorobenzene-$d_4$ (188 µL) were placed in a preheated oil bath at 40° C., 50° C., or 70° C. Benzylamine (51.5 µL, 0.471 mmol, 5 eq.) was then added in to each vial. 5 µL aliquots from both reactions were taken at one to five-minute time intervals and diluted in 600 µL CDCl$_3$ for $^1$H NMR spectroscopy. Rates of exchange were calculated by monitoring the change in concentration of 2 referenced to the DMA internal standard.

Figure 4:
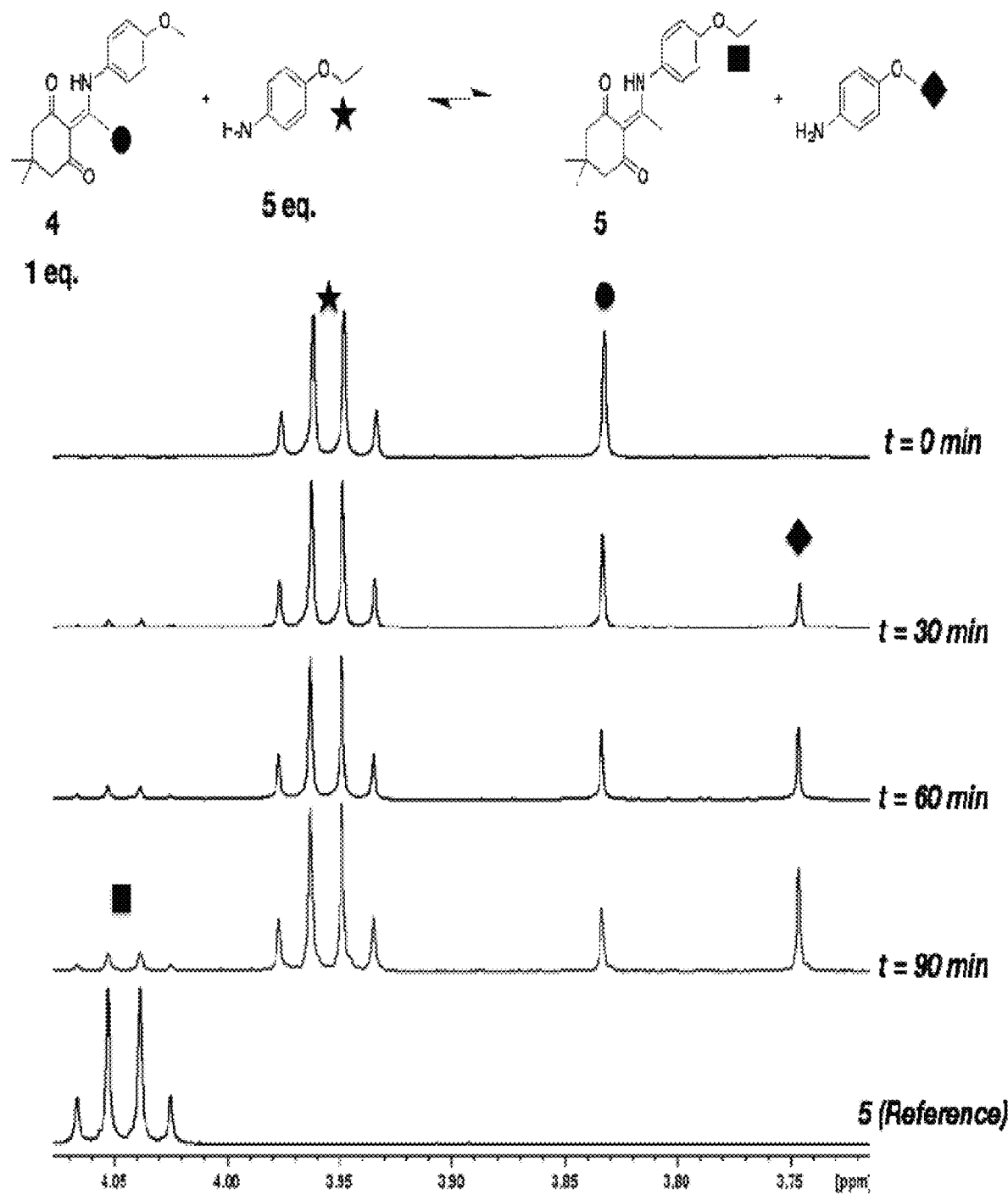
FIG. 4. Rate for aryl-aryl exchange measured using $^1$H NMR spectroscopy.
Figure 6:
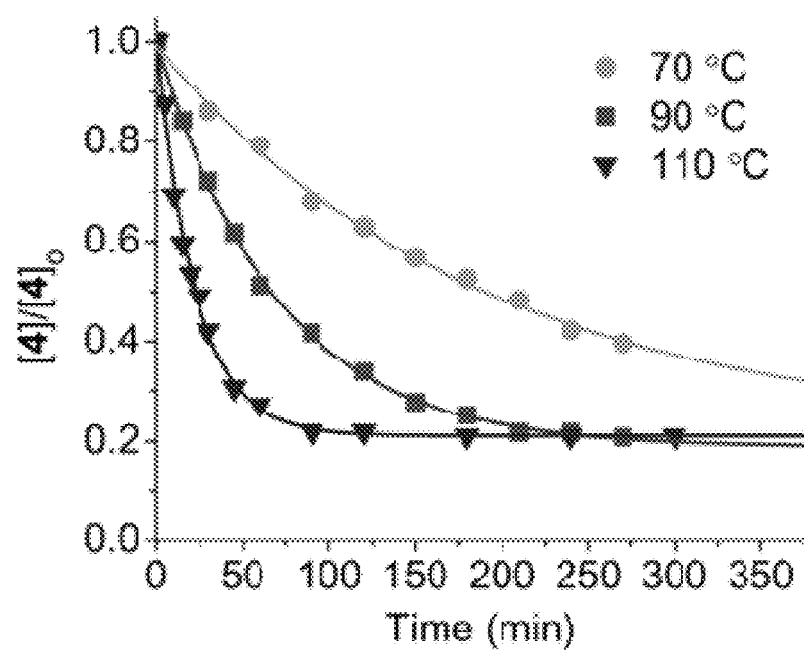
FIG. 6. Graph showing rate of aryl-aryl amine exchange.

Aryl-Aryl Amine (Aniline) Exchange (FIG. 4 & FIG. 6)

Two 4 mL vials containing compound 5 (25.0 mg, 0.087 mmol), tribromobenzene (27.1 mg, 0.086 mmol) as a standard, and 1,2-dichlorobenzene-$d_4$ (174 µL) were placed in a preheated oil bath at 70° C., 90° C., or 110° C. 1-aminohexane (56 µL, 0.435 mmol, 5 eq.) was then added. 5 µL aliquots from both reactions were taken at specified time intervals and diluted in 600 µL chloroform-d (CDCl$_3$) for $^1$H NMR spectroscopy. Rate was calculated by monitoring the concentration of 5 referenced to the 1,3,5-tribromobenzene standard at 7.29 ppm in the $^1$H NMR spectrum.

Analysis

Figure 7:
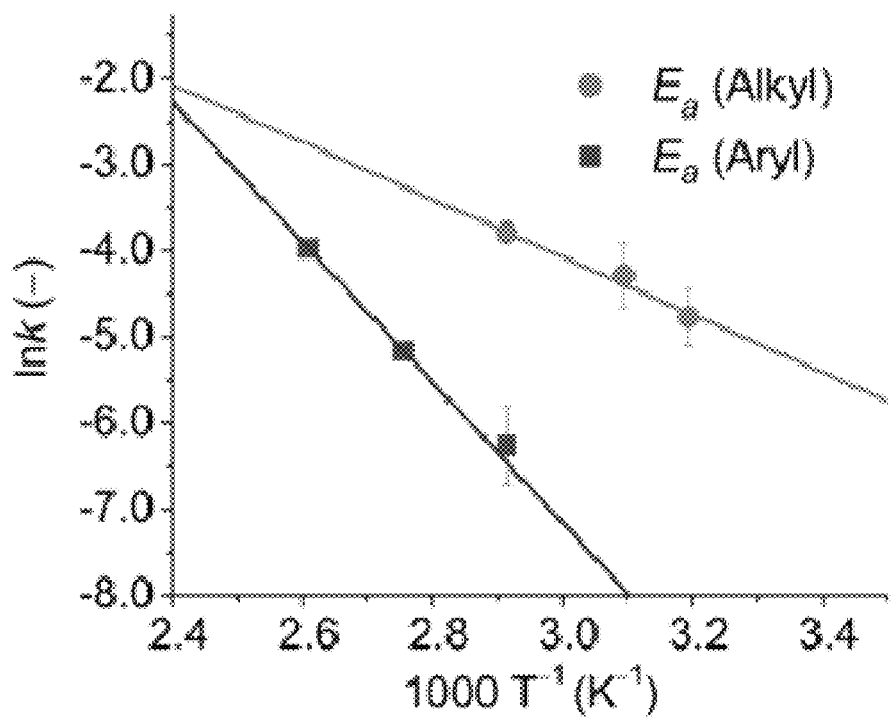
FIG. 7. Plot of $\ln(k_{obs})$ vs. $T^{-1}$ for both alkyl, and aryl amine exchange reactions using Equation 3.

Under the assumption of pseudo-first order conditions kinetics values of rate constants (k) were obtained by monitoring concentration of compound 2 (FIG. 5, Equation 1) and compound 5 for (FIG. 6, Equation 2). Activation energies for the small molecule kinetic studies were found using a plot of $\ln(k_{obs})$ vs. T$^{-1}$ for both alkyl, and aryl amine exchange reactions using Equation 3 (FIG. 7).

$$\ln\left(\frac{[2]}{[2]_0}\right) = -k_{obs}(t) \qquad \text{Equation 1}$$

where: $k_{obs} = k[\text{benzylamine}]^x$ $$\ln\left(\frac{[4]}{[4]_0}\right) = -k_{obs}(t) \qquad \text{Equation 2}$$

where: $k_{obs} = k[p-\text{ethoxyaniline}]^x$ x=order of amine (assumed to be 1)

$$\ln(k_{obs}) = \ln(A) - \frac{E_a}{RT}$$  Equation 3

Calculated Rate Constants (k)

TABLE 1

Calculated pseudo-first order rate constants (k) for alkyl-alkyl exchange (equilibration of 2 and 3) with a first order assumption in [benzylamine].

| Temperature | k (s$^{-1}$ M$^{-1}$) |
|---|---|
| 40° C. | 0.00848 ± 0.00059 |
| 50° C. | 0.01374 ± 0.00121 |
| 70° C. | 0.2263 ± 0.00033 |

TABLE 2

Calculated pseudo-first order rate constants (k) for aryl-aryl exchange (equilibration of 4 and 5) with a first order assumption in [p-ethoxyaniline].

| Temperature | k (s$^{-1}$ M$^{-1}$) |
|---|---|
| 70° C. | 0.00191 ± 0.00014 |
| 90° C. | 0.00572 ± 0.00010 |
| 110° C. | 0.01879 ± 0.00028 |

Synthesis of Polytopic Triketone Monomers

To synthesize diketoenamine polymers capable of undergoing associative bond exchange, polytopic triketone and a polytopic amine monomers are needed; additionally, excess-NH$_2$ should be present in the system and available for participating in associative bond exchange reactions with diketoenamine bonds. The polytopic character of the monomers used will influence the polymer architecture, accessing linear, branched, hyperbranched, dendritic, and networked materials. Many useful polytopic triketones are accessed synthetically from 1,3-diketones and polyacids: for example, ditopic triketone monomer DK6 was prepared from 5,5'-dimethyl-1,3-cyclohexanedione (dimedone) and adipic acid. (15) For comparison, triketone dimers were also synthesized using different length diacids, e.g., adipic acid (DK6), suberic acid (DK8), and sebacic acid (DK10) (FIG. 8).

General Synthesis of Linear Diketoenamine Polymers

Figure 8:
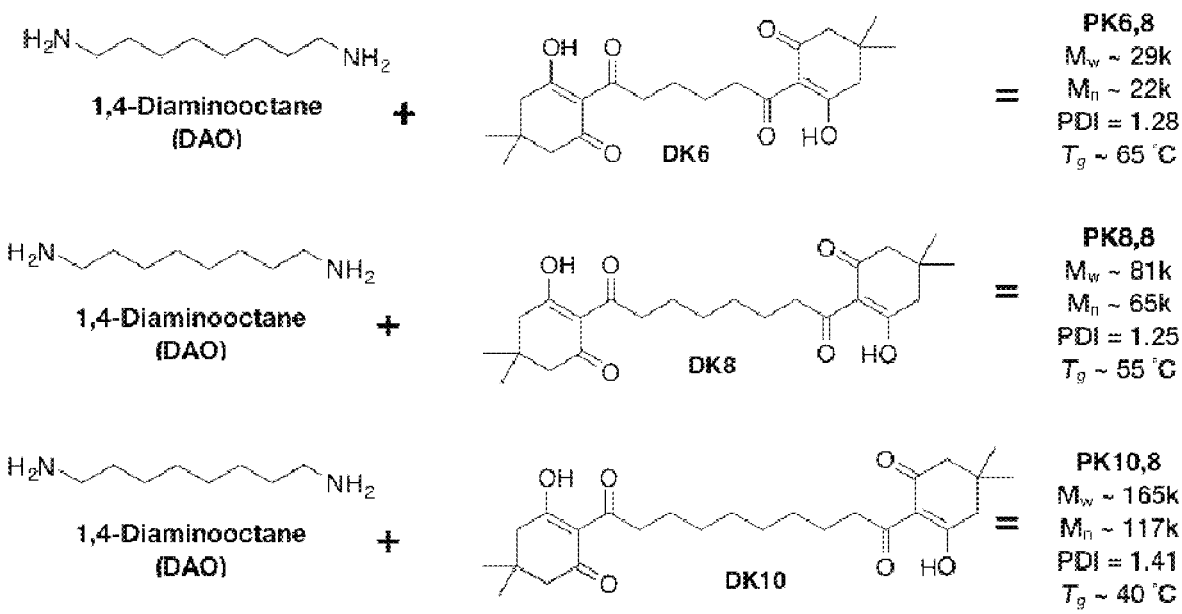
FIG. 8. Triketone dimers synthesized using different length diacids, e.g., adipic acid (DK6), suberic acid (DK8), and sebacic acid (DK10)
Figure 9:
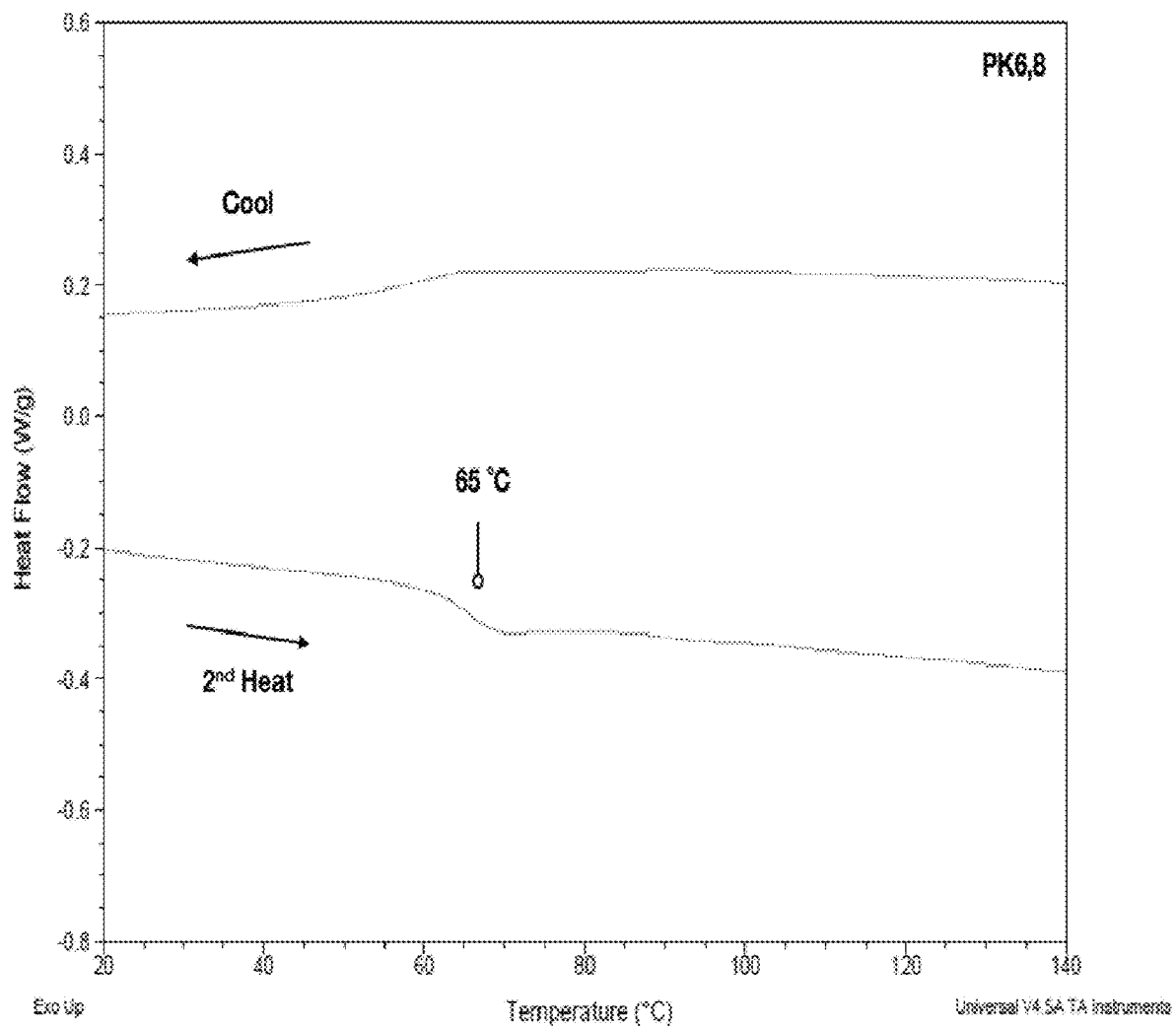
FIG. 9. Heat flow versus temperature for PK6,8.
Figure 10:
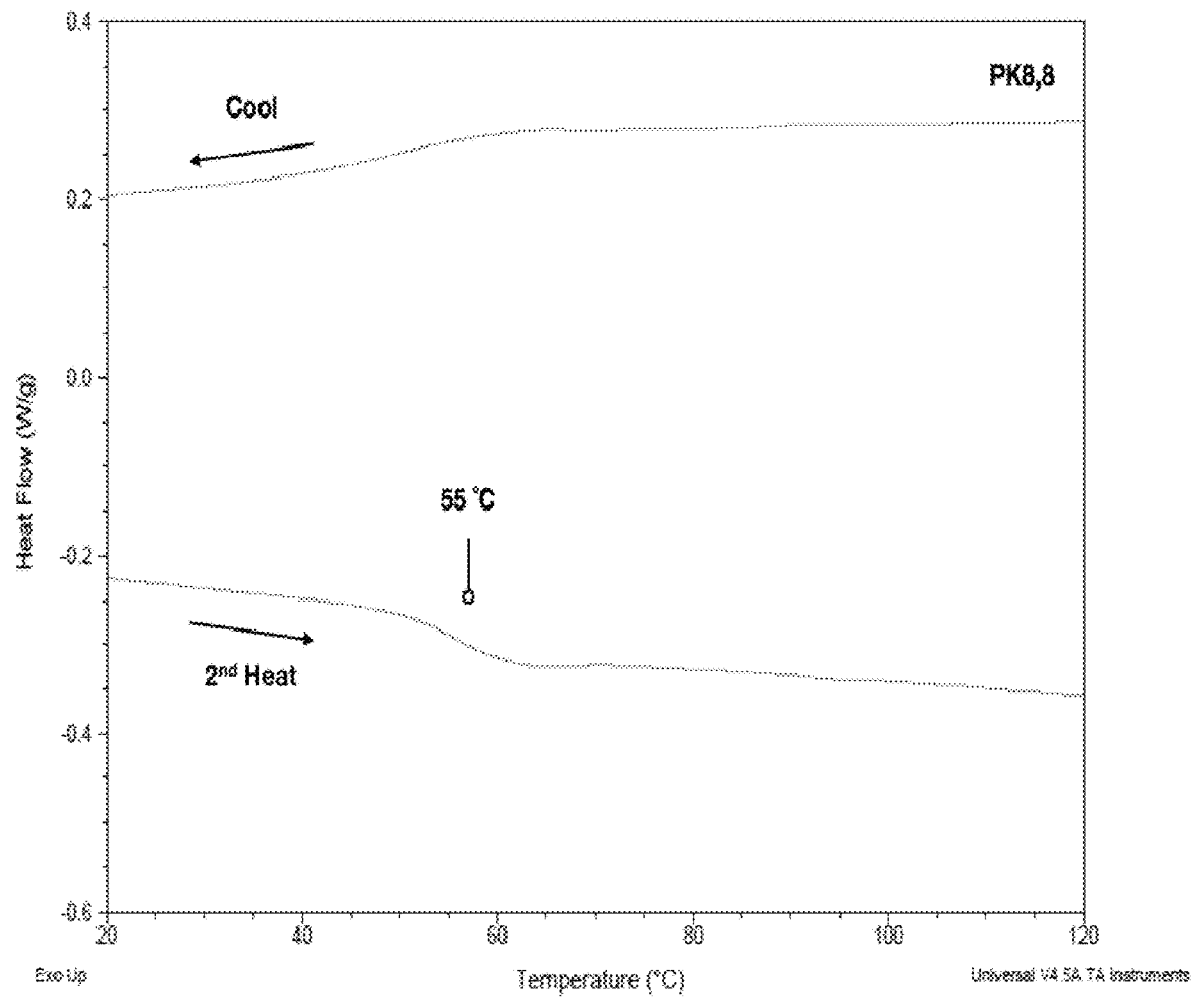
FIG. 10. Heat flow versus temperature for PK8,8.
Figure 11:
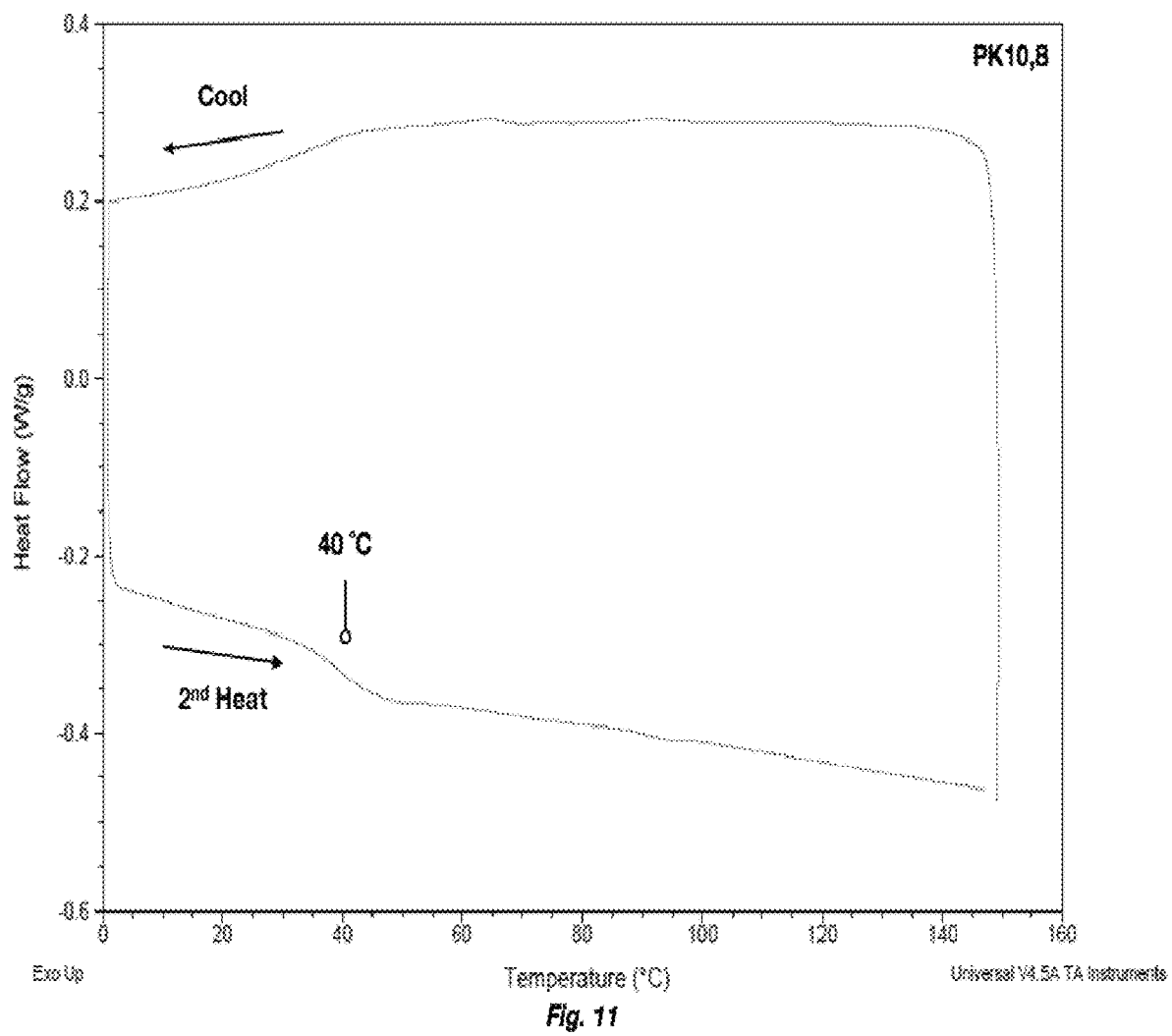
FIG. 11. Heat flow versus temperature for PK10,8.

Linear polymers were synthesized by reacting triketone DK6, DK8, or DK10 with 1,4-diaminooctane (DAO) in a 1:1 stoichiometry to yield, respectively, PK6,8, PK8,8, and PK10,8 (FIG. 8). In general, the glass transition temperature decreases with increasing length of triketone from T$_g$~65° C. (PK6,8, FIG. 9), to T$_g$~55° C. (PK8,8, FIG. 10), and T$_g$~40° C. (PK10,8, FIG. 11). Size-exclusion chromatography (SEC) was used to characterize the weight average (Mw) and number average (Mn) molecular weights, as well as the polydispersity index (PDI) of each polymer (tabulated in FIG. 8). In general, the molecular weight increases with increasing triketone linker from Mw~29 k for PK6,8 to Mw~165 k for PK8,10.

Synthesis of Network Polymers

Figure 12:
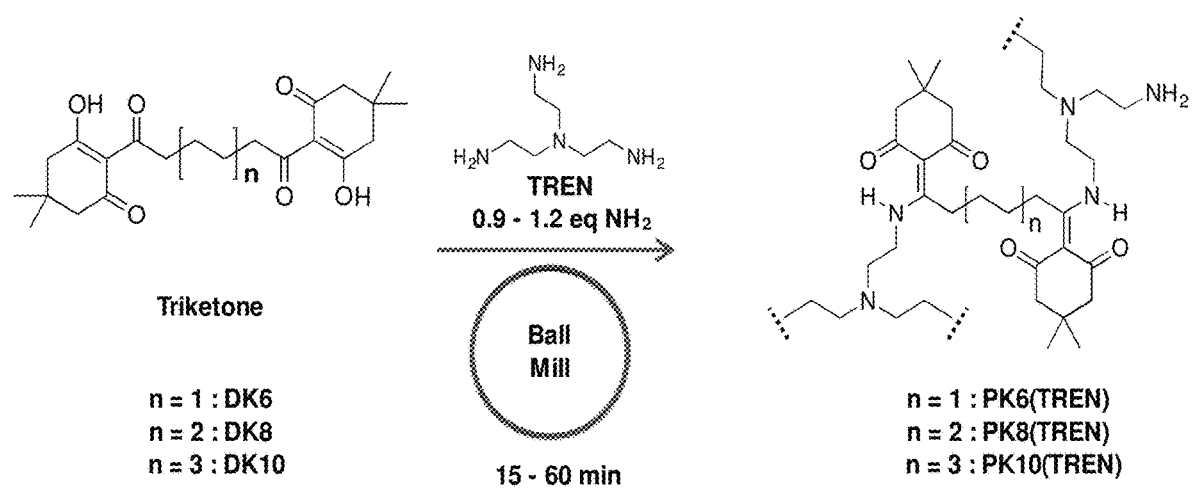
FIG. 12. Triketones DK6, DK8, and DK10 each mixed with tris(2-aminoethyl)amine (TREN) and ball-milled to form network polymer DK6(TREN), DK8(TREN), and DK10(TREN), respectively.
Figure 13:
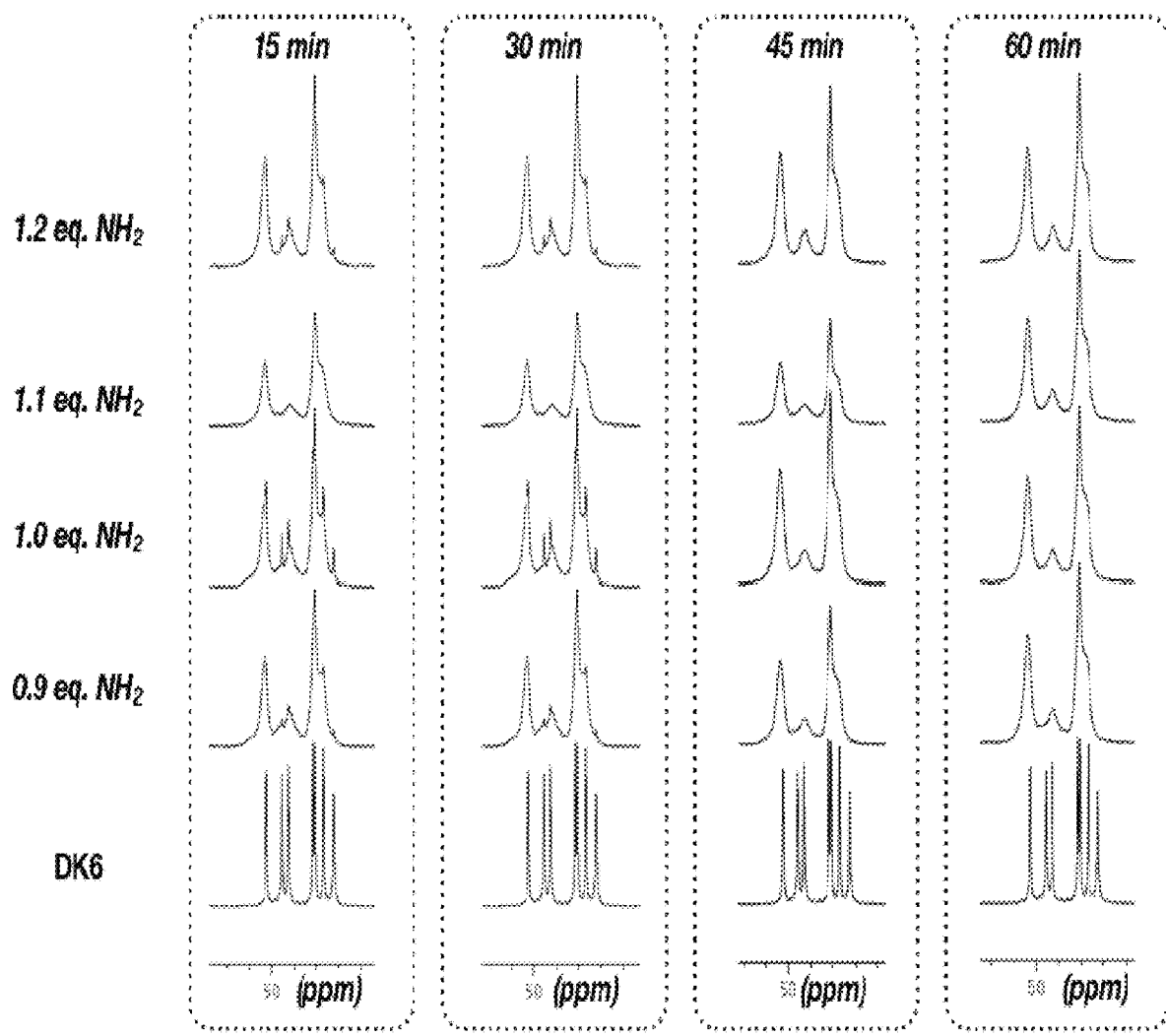
FIG. 13. Monitor of reaction by solid-state NMR.

The spontaneous and essentially quantitative conversion of triketones to diketoenamines enables polymers to be synthesized very quickly, in high yields, forming only water as a byproduct. In many cases, mechano-polymerization (e.g., ball-milling) is available to synthesize the polymers, obviating the use of solvent. (16) For example, triketone DK6 was mixed with tris(2-aminoethyl)amine (TREN) and ball-milled to form network polymer PK6(TREN) (FIG. 12). The extent of reaction was monitored by solid-state NMR (FIG. 13), glass transition temperature (T$_g$) (FIG. 14), and insoluble (gel) fraction (FIG. 15) at 15 minute intervals to understand the evolution of material properties and network density as a function of ball-milling time at both sub- and super-stoichiometric quantities of amine.

Figure 14:
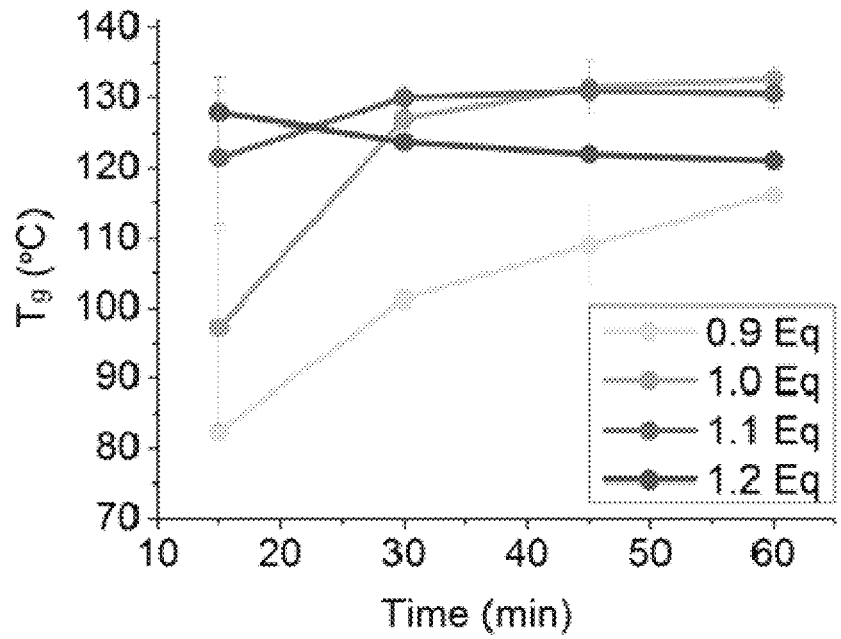
FIG. 14. Monitor of reaction by glass transition temperature ($T_g$).
Figure 15:
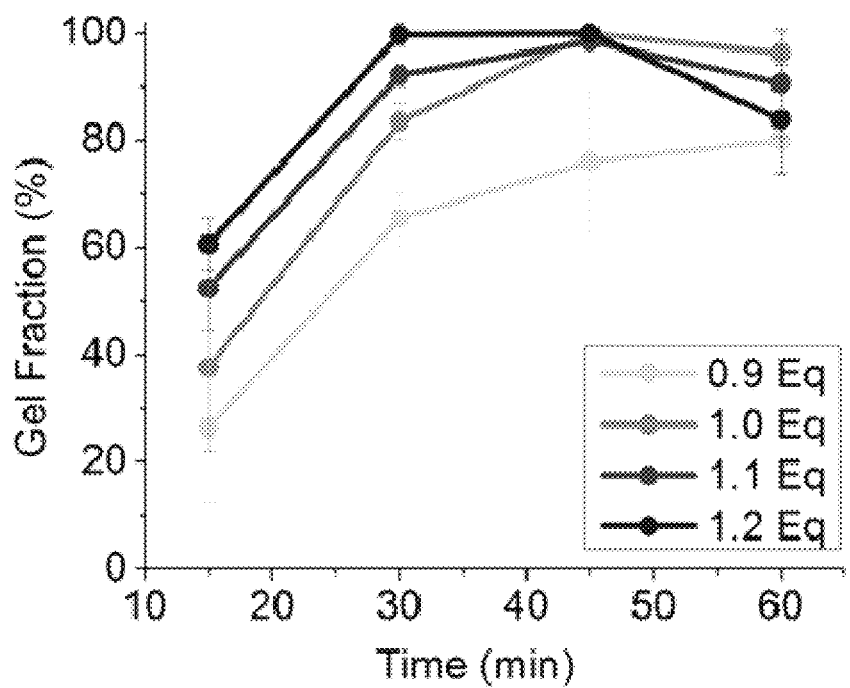
FIG. 15. Monitor of reaction by insoluble (gel) fraction percentage.

In addition to reducing the use of volatile organic compounds (VOCs) during polymerization, the data in FIG. 14 & FIG. 15 show that network polydiketoenamines with high T$_g$ (e.g., >120° C., FIG. 16) and high gel fractions (e.g., >90%) can be synthesized using ball-milling without external heat sources, and reactions are complete in less than 1 h.

Properties of Network Polymers for Specific Formulations

As a comparison, the suberoyl (DK8) and sebacoyl (DK10) ditopic triketones were ball milled with TREN (1.1 eq. NH$_2$) for 45 min to give materials that have Ts of 116° C. (PK8(TREN)) and 102° C. (PK10(TREN)), respectively (FIG. 17 & FIG. 18), indicating that even small modifications to the linker between reactive sites has significant impact on material properties.

Figure 19:
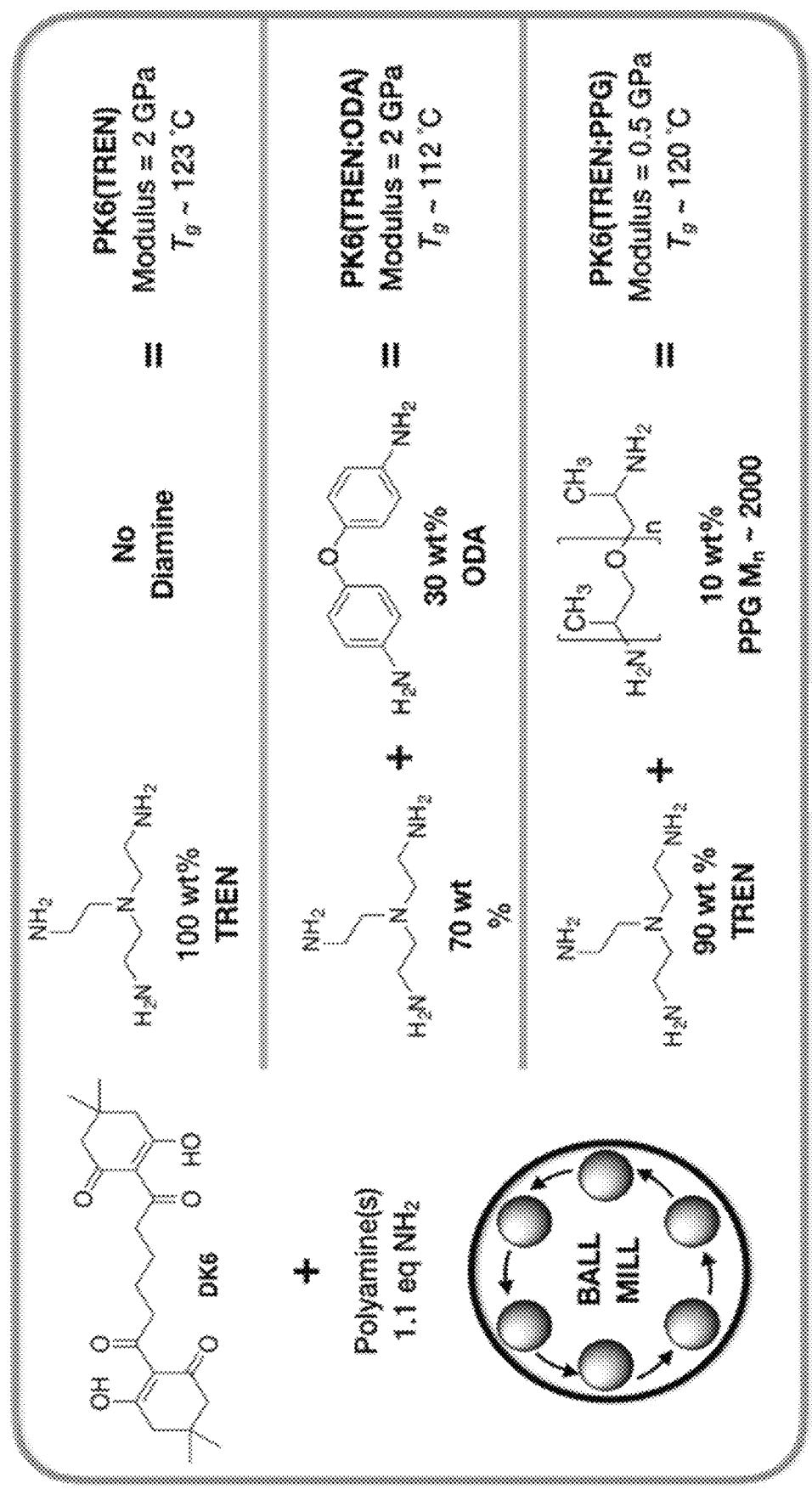
FIG. 19. Triketone DK6 each mixed with TREN, TREN and ODA, and TREN and PPG to form network polymer DK6(TREN), DK6(TREN:ODA), and DK6(TREN:PPG), respectively.

In addition to exploring diversity with respect to electrophile, the ability of triketones to react with both aliphatic and aromatic amines enables a wide range of possible formulations (FIG. 19). Accordingly, we synthesized two additional polymers using the ditopic triketone DK6 and a mixture of 70 wt % TREN and 30 wt % of 4,4'-oxydianiline (ODA), denoted as PK6(TREN:ODA), as well as 90 wt % TREN and 10 wt % poly(propylene glycol) bis(2-aminopropyl ether) (PPG), denoted as PK6(TREN:PPG).

Figure 20:
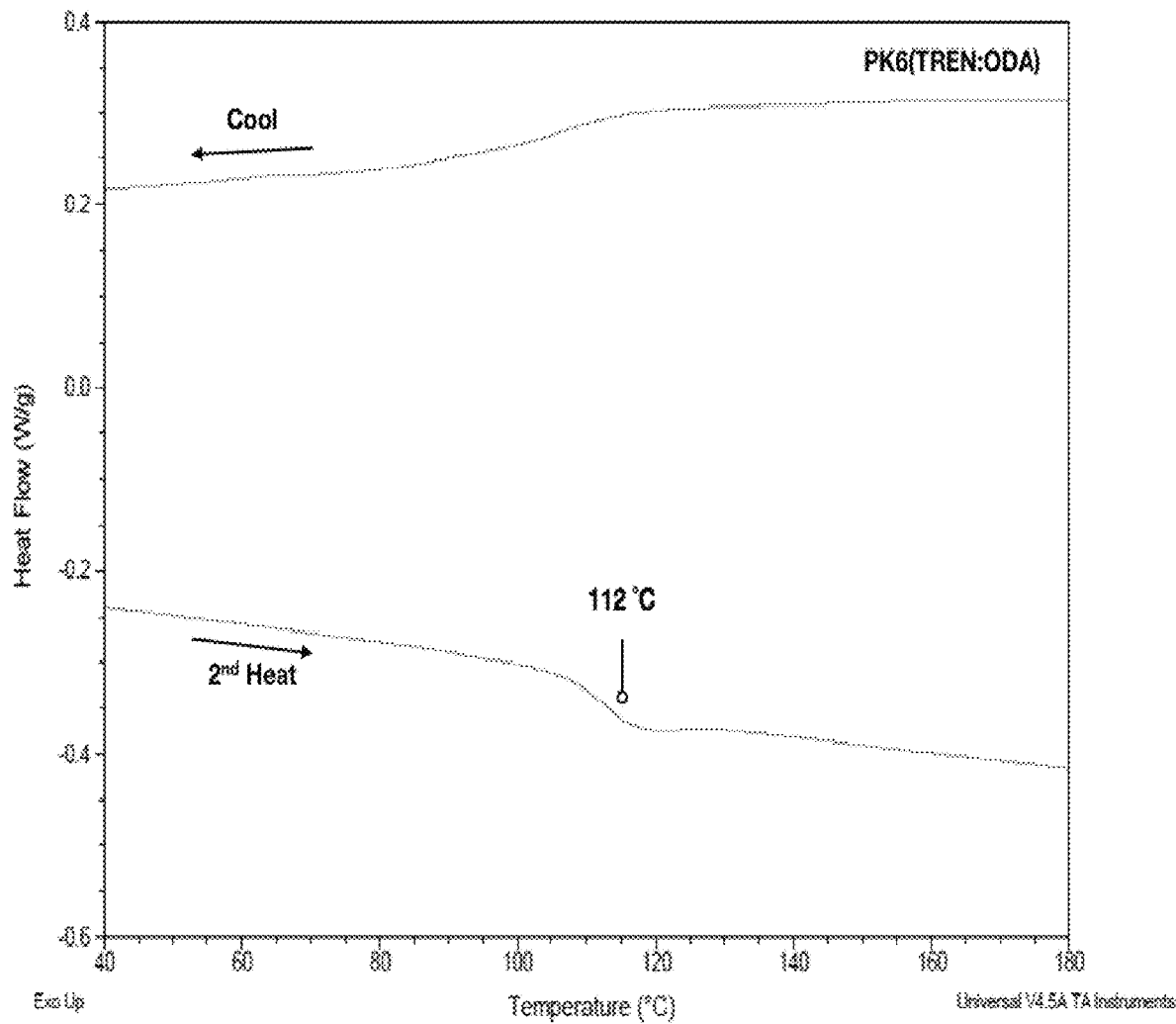
FIG. 20. Heat flow versus temperature for PK6(TREN:ODA).
Figure 21:
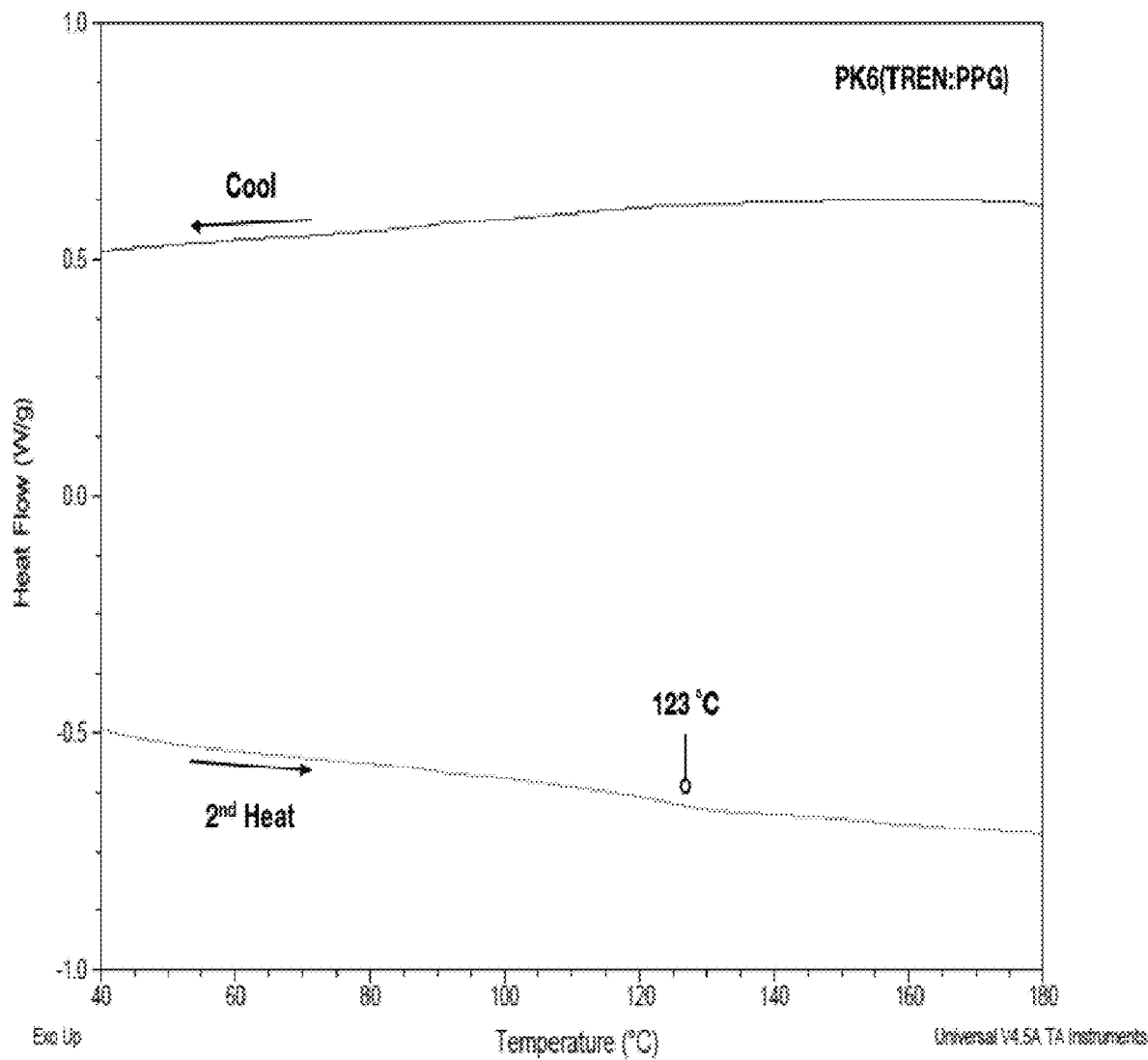
FIG. 21. Heat flow versus temperature for PK6(TREN:PPG).

By changing the type and quantity of diamine the material properties can be significantly modified while still maintaining T$_g$'s>100° C. FIG. 20 shows the DSC thermogram for PK6(TREN:ODA) with a measured T$_g$ of ~112° C. and FIG. 21 shows the DSC thermogram for PK6(TREN:PPG), with a measured T$_g$ of ~123° C.

De-Polymerization and Monomer Recovery

Figure 22:
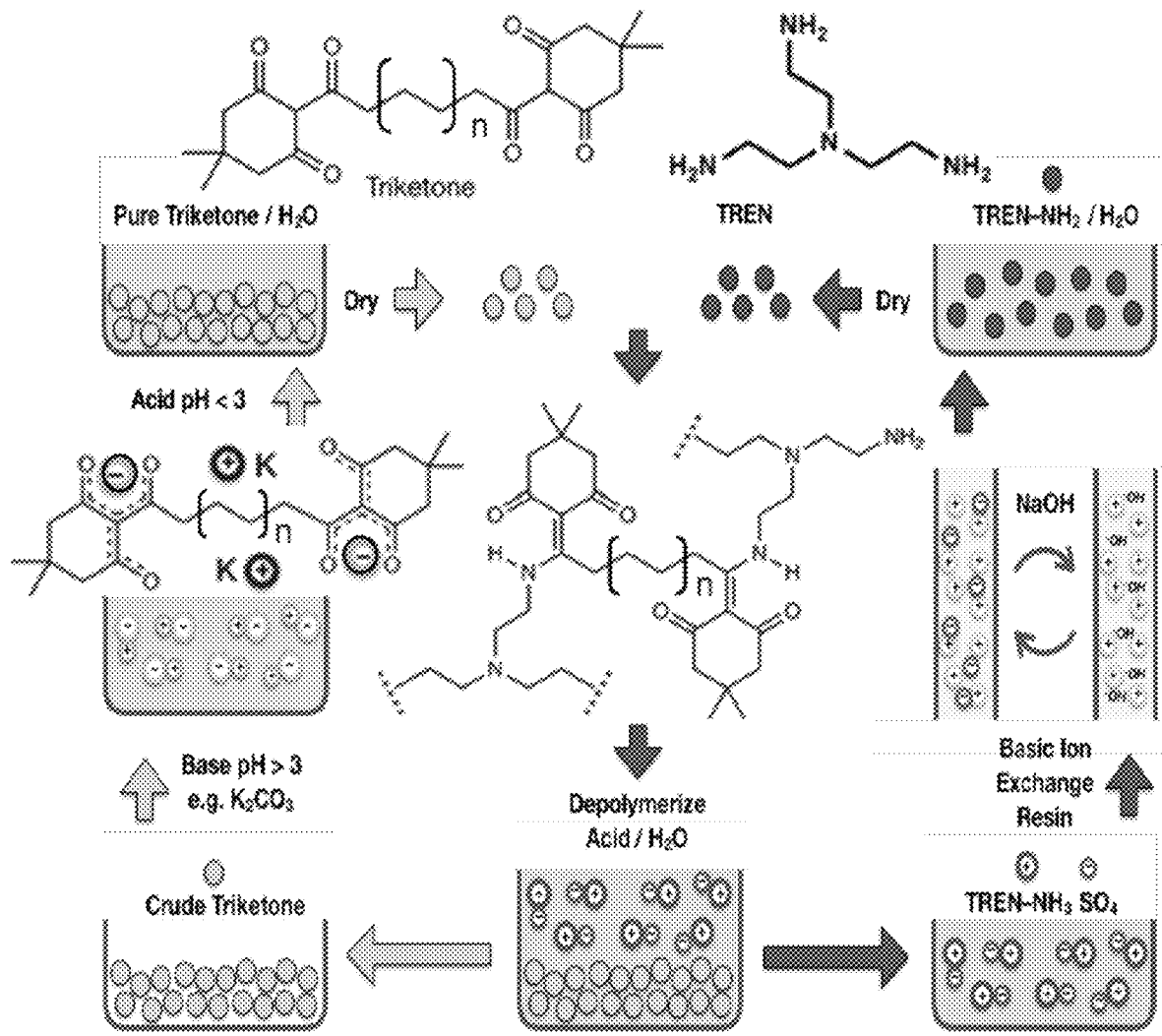
FIG. 22. Triketone recovered in a closed-loop process.
Figure 23:
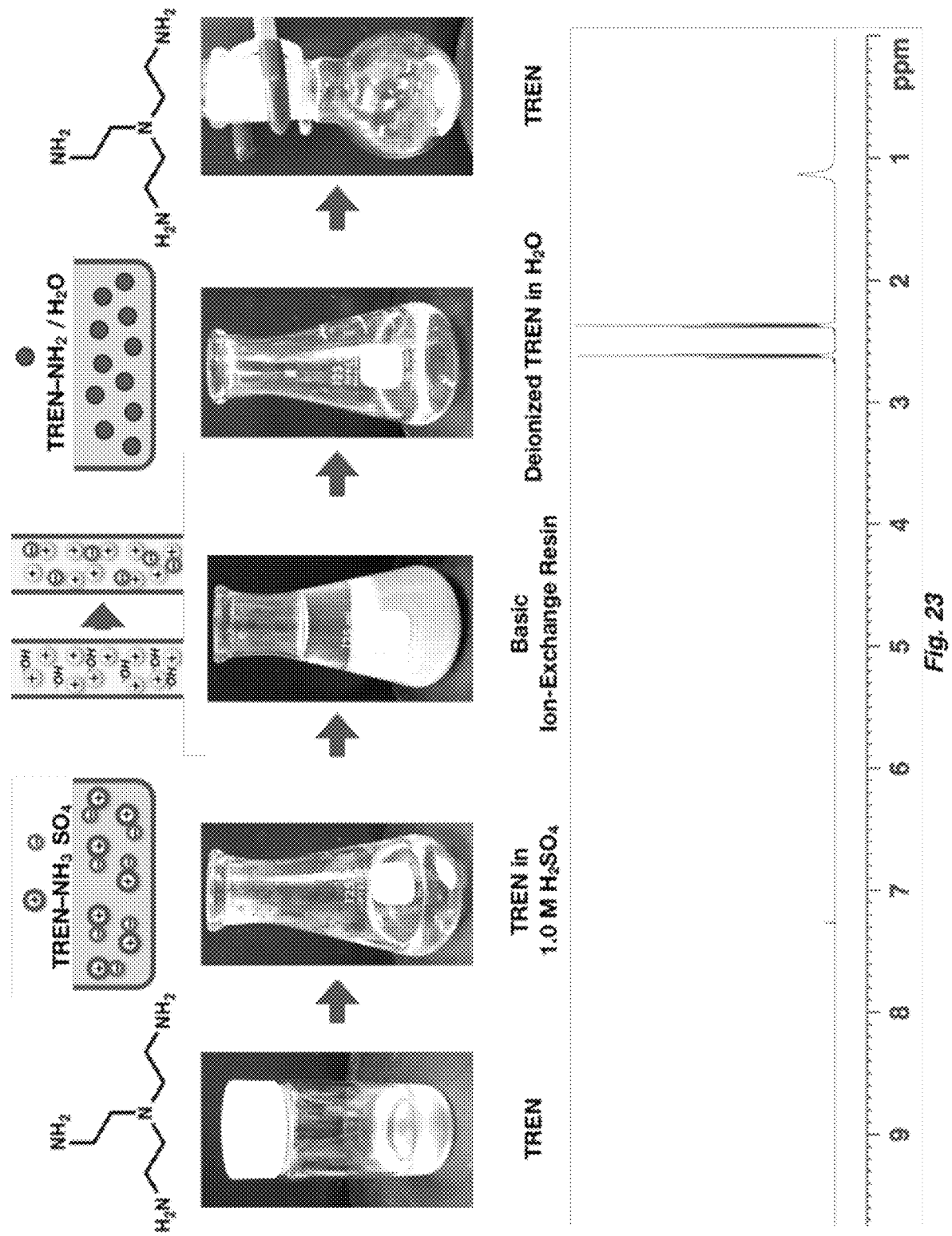
FIG. 23. Amine monomers recovered in a closed-loop process
Figure 24:
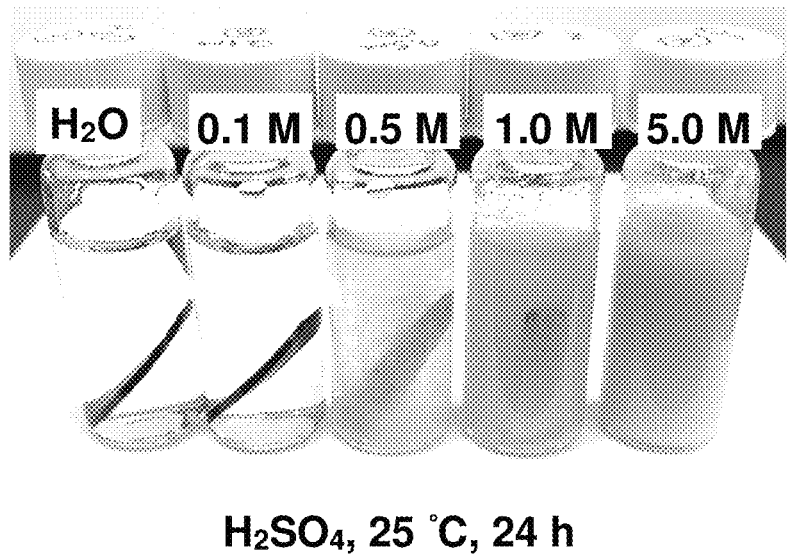
FIG. 24. Rate of depolymerization of poly(diketoenamines) is dependent on the concentration of acid.
Figure 25:
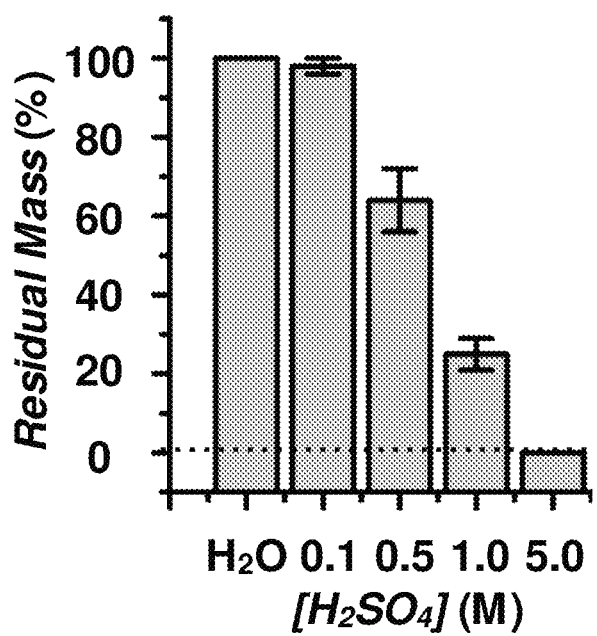
FIG. 25. Rate of depolymerization of poly(diketoenamines) is dependent on the concentration of acid.
Figure 26:
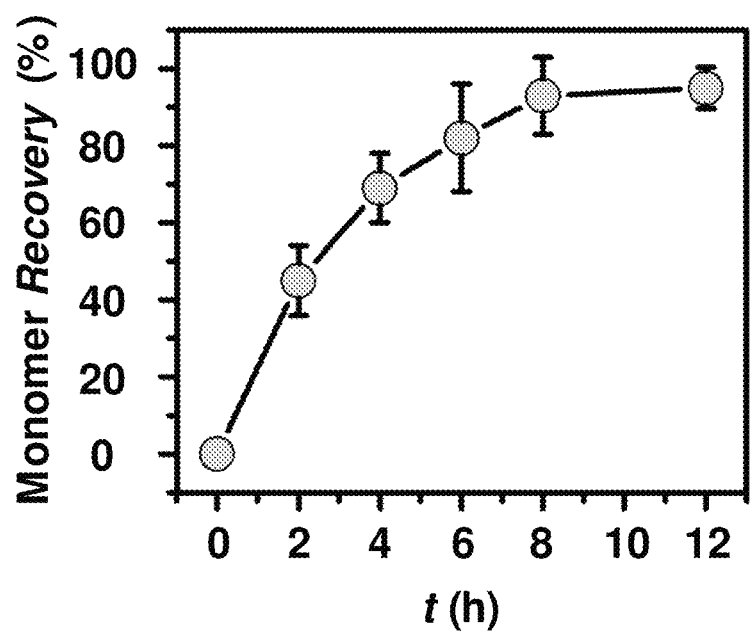
FIG. 26. Triketone monomer can be recovered in yields greater than 95%.
Figure 27:
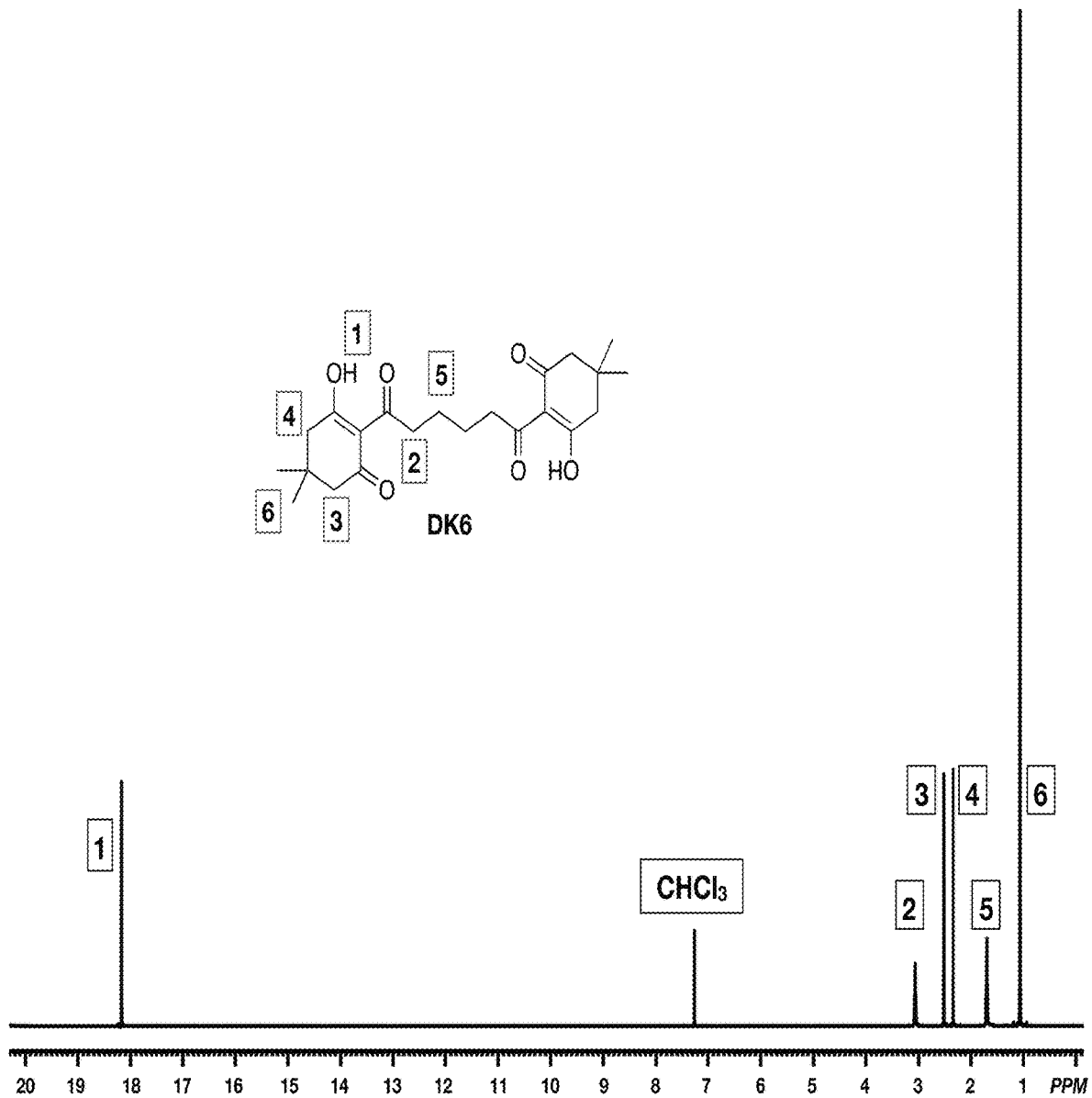
FIG. 27. Triketone monomer can be recovered in yields greater than in purities >99%.
Figure 28:
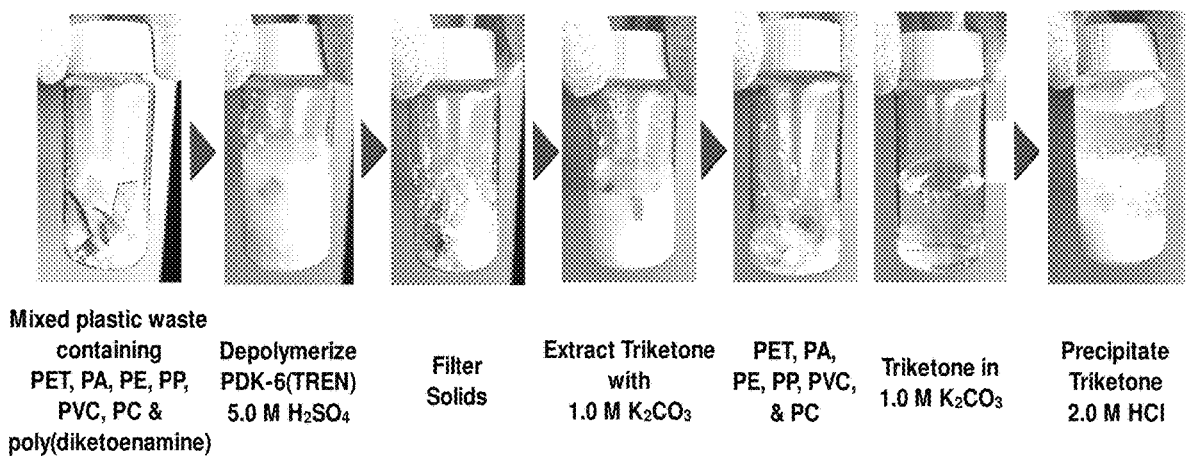
FIG. 28. Poly(diketoenamine) waste can be selectively chemically recycled.

Poly(diketoenamines) can be depolymerized to yield pure triketone monomer in the presence of acidified water. We demonstrate that both triketone and amine monomers can be recovered in a closed-loop process (FIG. 22 and FIG. 23). The rate of depolymerization of poly(diketoenamines) is dependent on the concentration of acid (FIG. 24 and FIG. 25), and we demonstrate that the triketone monomer can be recovered in yields greater than 95% (FIG. 26) and in purities >99% by $^1$H NMR (FIG. 27). We also demonstrate that poly(diketoenamine) waste can be selectively chemically recycled in the presence of common plastics, including but not limited to: (poly(ethylene terephthalate) (PET), polyamide nylon-6,6 (PA), polyethylene (PE), polypropylene (PP), poly(vinyl chloride) (PVC), polycarbonate (PC), obviating laborious and expensive material sorting (FIG. 28). Analysis of the material obtained from polymer waste shows a remarkably high purity as determined by $^1$H NMR, demonstrating that high-performance network materials can be both dynamic and easily recyclable using cradle-to-cradle and closed-loop design principles.

Figure 29:
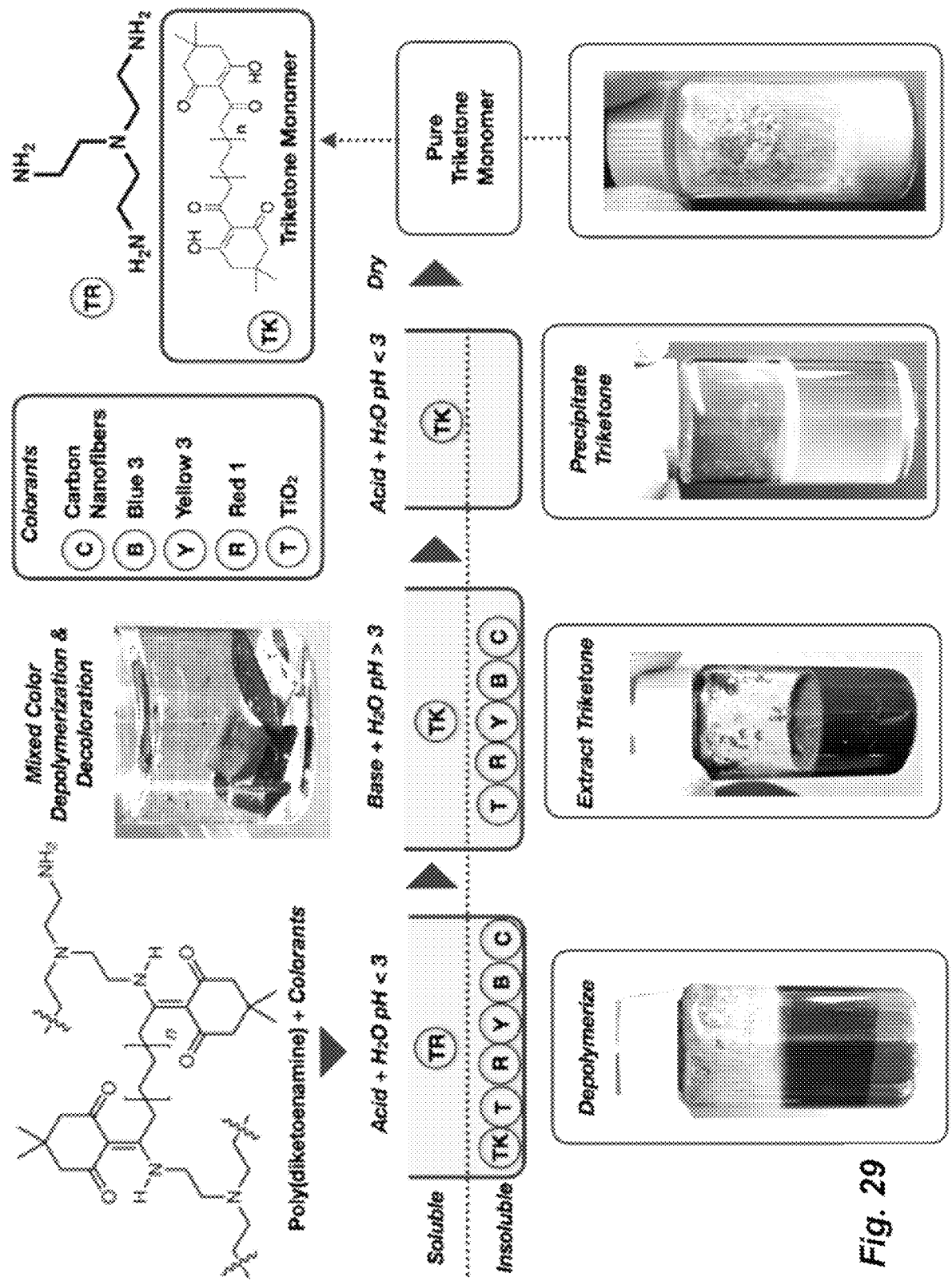
FIG. 29. Colored poly(diketoenamine) materials can be depolymerized to yield pure, colorless triketone monomer.

We demonstrate that colored poly(diketoenamine) materials can be depolymerized to yield pure, colorless triketone monomer (FIG. 29).

Figure 30:
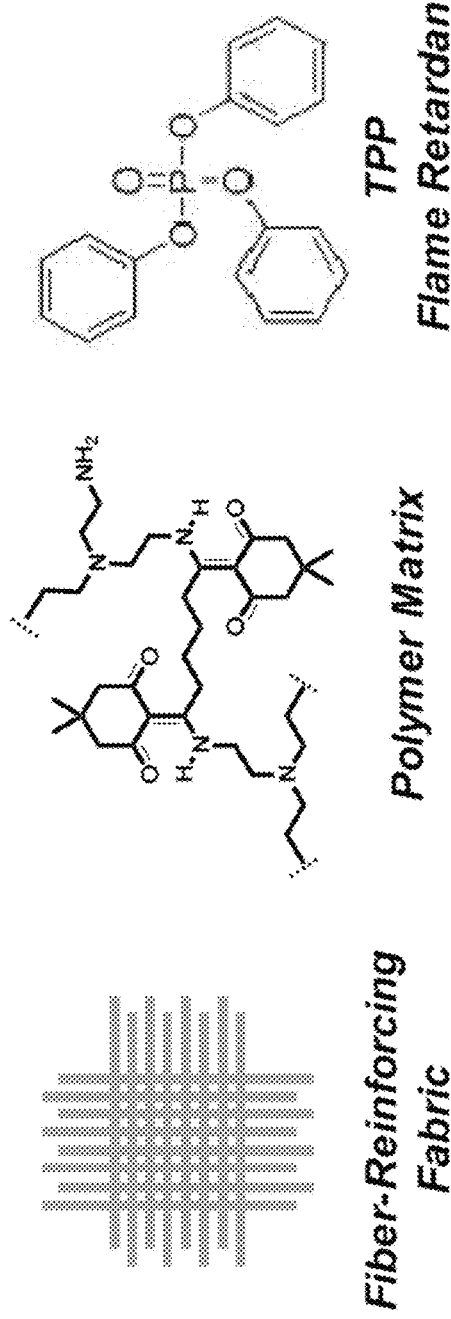
FIG. 30. Fiber-reinforced poly(diketoenamine) composite materials containing 25% (w/w) triphenylphosphine (TPP) flame retardant, can be depolymerized to recover pure triketone monomer, pure TPP flame retardant, as well as the fiber reinforcing fabric.
Figure 30:
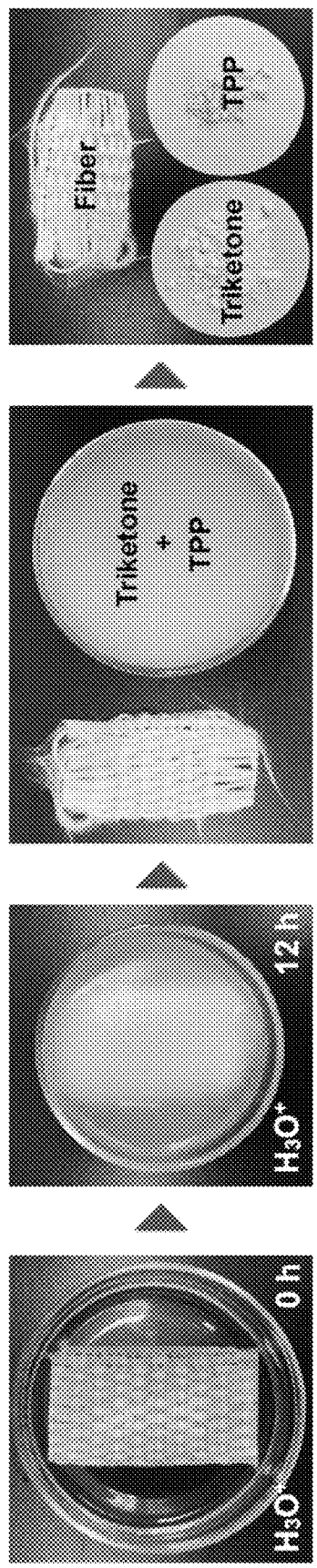

We demonstrate fiber-reinforced poly(diketoenamine) composite materials containing 25% (w/w) triphenylphosphine (TPP) flame retardant, can be depolymerized to recover pure triketone monomer, pure TPP flame retardant, as well as the fiber reinforcing fabric (FIG. 30).

Poly(Diketoenamine) Formulation and Thermomechanical Properties

Figure 31:
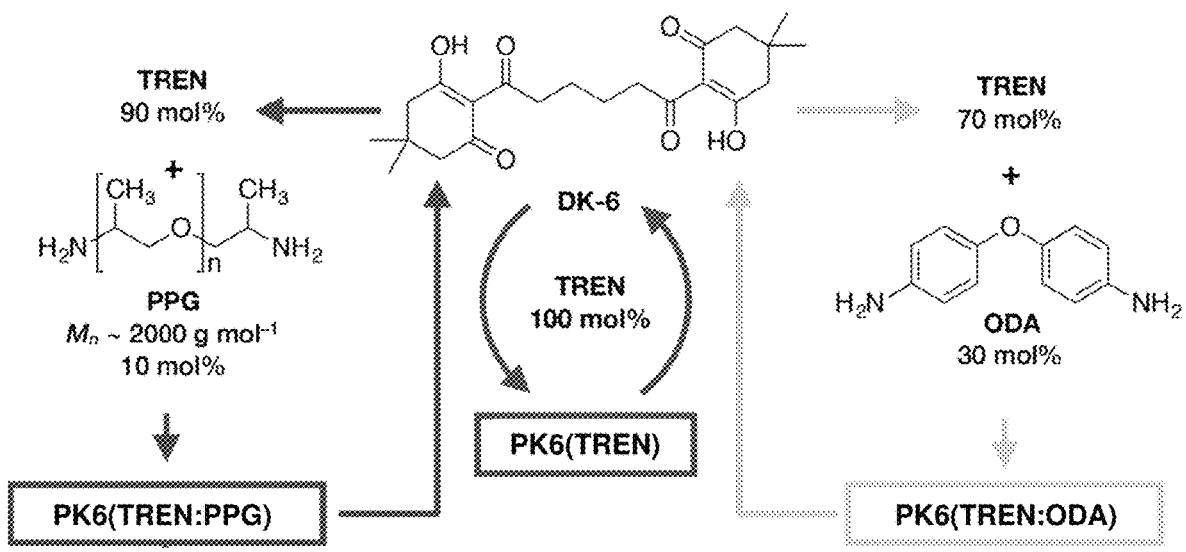
FIG. 31. The recovery of pure triketone monomer in the recycling process allows poly(diketoenamine)s to be re-polymerized into the same polymers with the same formulation, or differentiated formulations.
Figure 32:
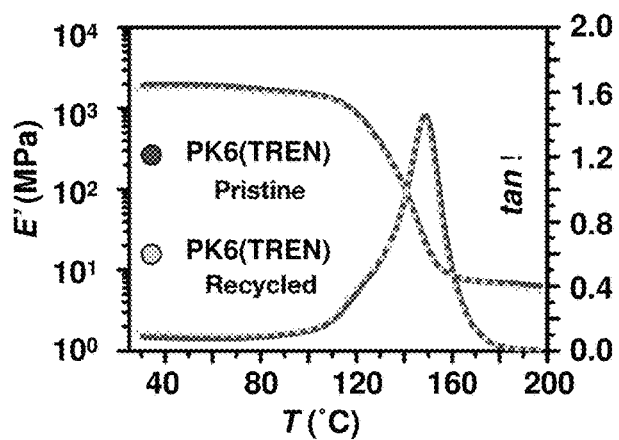
FIG. 32. Recycled triketone monomer can be repolymerized to achieve materials with identical storage modulus (E') as measured by DMA.

The recovery of pure triketone monomer in the recycling process allows poly(diketoenamine)s to be re-polymerized into the same polymers with the same formulation, or differentiated formulations (FIG. 31). We demonstrate that recycled triketone monomer can be repolymerized to achieve materials with identical storage modulus (E') as measured by DMA (FIG. 32).

Figure 33:
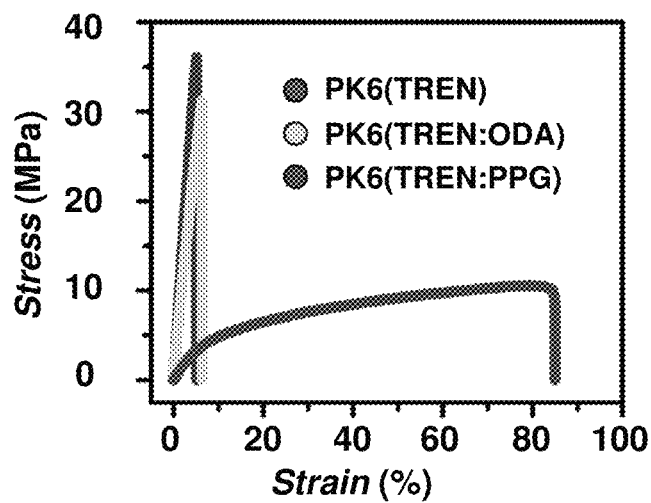
FIG. 33. Stress versus strain for PK6(TREN), PK6(TREN:ODA), and PK6(TREN:PPG).
Figure 34:
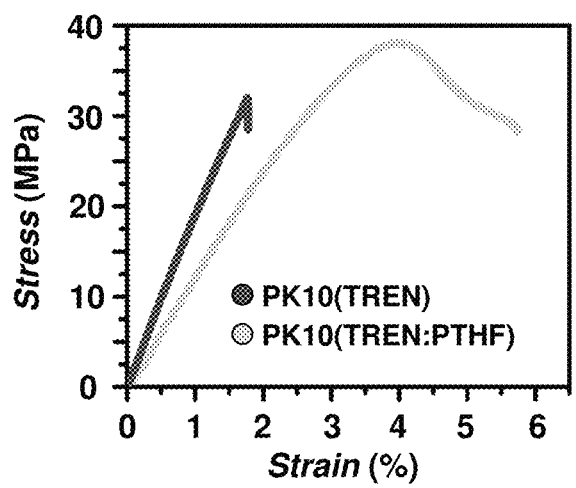
FIG. 34. Stress versus strain for PK10(TREN) and PK10(TREN:PTHF).

We demonstrate that the addition of various diamines (FIG. 31) including but not limited to 4,4'oxydianiline (ODA), poly(propylene glycol) bis(2-aminopropyl ether) (PPG), poly(tetrahydrofuran) bis(3-aminopropyl) terminated (PTHF) as well as tris(2-aminoethylamine) (TREN), into poly(diketoenamine) networks results in differentiated polymer properties (FIG. 33 and FIG. 34).

Temperature-Dependent Stress-Relaxation of Poly(Diketoenamine)s

Figure 35:
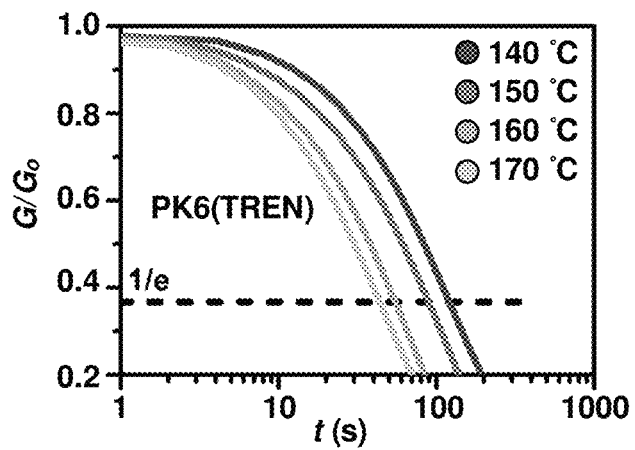
FIG. 35. $G/G_0$ versus time for PK6(TREN) at various temperatures.
Figure 36:
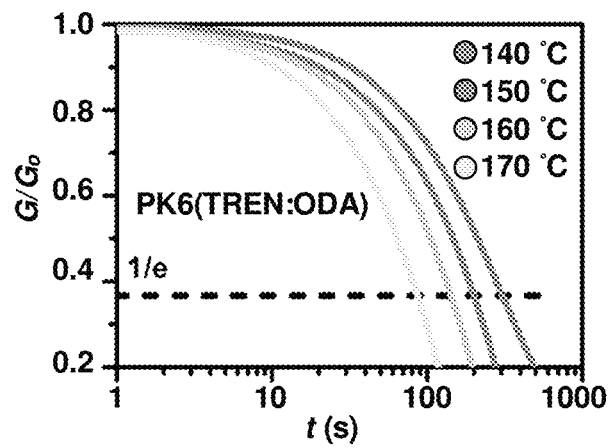
FIG. 36. $G/G_0$ versus time for PK6(TREN:ODA) at various temperatures.
Figure 37:
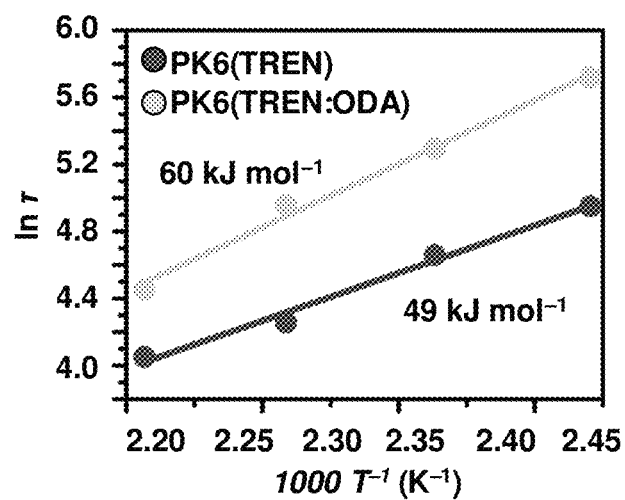
FIG. 37. Ln T versus 1000 $T^{-1}$ for PK6(TREN) and PK6(TREN:ODA) at various temperatures.

The temperature-dependent stress-relaxation ($G/G_o$) behavior of poly(diketoenamine) networks was used to calculate the solid-state activation energy ($E_a$) for diketoenamine bond exchange. Stress-relaxation data show Arrhenius-type behavior, with an activation energy of 49 kJ mol$^{-1}$ for PK6(TREN) for purely aliphatic amine bond-exchange, and 60 kJ mol$^{-1}$ for PK6(TREN:ODA), containing a mixture of both aliphatic and aromatic amines (FIG. 35, FIG. 36. and FIG. 37).

REFERENCES CITED HEREIN

1. Rahimi, A., García, J. M. *Nat. Rev. Chem.* 1, 0046 (2017).
2. Helms, B. A., Russell, T. P. *Chem.* 1, 816-818 (2016).
3. Otto, S. et al. *Chem. Rev.* 106, 3652-3711 (2006).
4. Zhang, W. et al. *Chem. Soc. Rev.* 42, 6634-6654 (2013).
5. Stoddart, J. F. et al. *Angew. Chem. Int. Ed.* 41, 898-952 (2002)
6. Leibler, L. et al. *Science*, 334, 965 (2011).
7. Dichtel, W. R. et al. *J. Am. Chem. Soc.* 137, 14019 (2015).
8. Du Prez, F. E. et al. *Adv. Funct. Mater.* 25, 2451 (2015).
9. Hillmyer, M. A. et al. *ACS Macro Lett.* 3, 607 (2014).
10. Leibler L. et al. *Science*, 356, 62-65 (2017).
11. Du Prez, F. E. et al. *Nat. Chem.* 6, 815-821 (2014).
12. Anslyn, E. V. et al. *Nat. Chem.* 8, 968-973 (2016).
13. Chan, W. C. et al. *Tetrahedron Lett.* 37, 2625 (1996).
14. Chhabra, S. R. et al. *Tetrahedron Lett.* 38, 4849 (1997).
15. Lindner, W. et al. *Tetrahedron*, 71, 2698 (2015).
16. Borchardt, L. et al. *RSC Adv.*, 6, 64799 (2016).

Example 1

Synthesis of Triketone (1)

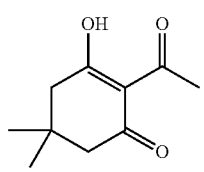

2-Acetyl-5,5-dimethyl-1,3-cyclohexanedione (1) was prepared as previously reported.[1] (1) Characterization Data: $^1$H NMR (500 MHz, CDCl$_3$) 18.11 (s, 1H), 2.58 (s, 3H) 2.51 (s, 2H), 2.34 (s, 2H), 1.05 (s, 6H) ppm; $^{13}$C NMR (125 MHz, CDCl$_3$) 202.53, 197.98, 195.28, 112.40, 52.51, 46.93, 30.71, 28.64, 28.25 ppm; FT-IR (neat, cm$^{-1}$) 3630, 3319, 2959, 2889, 2872, 2815, 1738, 1665, 1554, 1467, 1442, 1420, 1406, 1389, 1370, 1333, 1319, 1292, 1259, 1237, 1199, 1166, 1149, 1126, 1048, 1029, 976, 948, 934, 925, 890, 819, 764, 750, 705, 663; HRMS (EI) m/z for C$_{10}$H$_{14}$O$_3$ calculated 182.0943, found 182.094; analysis (calculated, found for C$_{10}$H$_{14}$O$_3$): C (65.92, 65.74), H (7.74, 7.74).

Example 2

Synthesis of Diketoenamine (2)

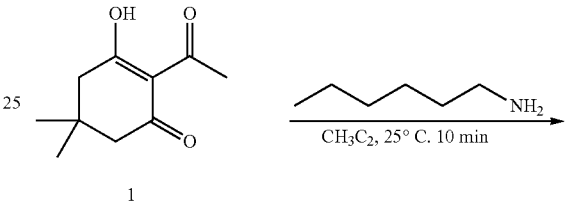

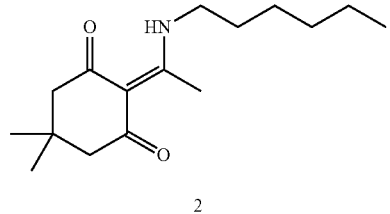

1 (1 mmol) and hexylamine (1 mmol) were dissolved in 500 μL CHCl$_3$ and stirred at room temperature. The reaction was monitored using TLC (silica, 3:1 Hex:EtOAc) and was determined to be complete after 10 minutes. The solidified mixture was dissolved in EtOAc and purified by column chromatography using n-hexane/EtOAc as the eluent (SiO$_2$, 0-50% EtOAc). Column fractions containing pure product were combined and solvent was removed under reduced pressure to yield 2 as an oily pale yellow solid (80% isolated yield). Characterization Data: $^1$H NMR (500 MHz, CDCl$_3$): δ 13.39 (broad s, 1H), 3.359 (m, 2H), 2.54 (s, 3H), 2.36 (s, 2H), 2.33 (s, 2H), 1.66 (m, 2H), 1.39 (m, 2H), 1.35-1.26 (m, 4H), 1.09 (s, 6H), 0.87 (t, J=6.8 Hz, 3H) ppm; $^{13}$C NMR (125 MHz, CDCl$_3$): δ 199.06, 196.88, 173.49, 107.90, 53.63, 52.38, 43.60, 31.43, 30.21, 29.12, 28.38, 26.65, 18.03, 14.09 ppm; FT-IR (neat, cm$^{-1}$) 3525, 3175, 2955, 2930, 2892, 2865, 2816, 1638, 1574, 1465, 1422, 1385, 1367, 1334, 1301, 1287, 1237, 1211, 1198, 1165, 1142, 1125, 1090, 1034, 1018, 981, 954, 938, 897, 885, 824, 764, 748, 726, 709, 667, 662; HRMS (ESI) m/z for C$_{16}$H$_{28}$NO$_2^+$ (MH)$^+$ calculated 266.2120, found 266.2115; analysis (calculated, found for C$_{16}$H$_{27}$NO$_2$): C (72.41, 72.51), H (10.25, 10.09), N (5.28, 5.24).

Example 3

Synthesis of Diketoenamine (3)

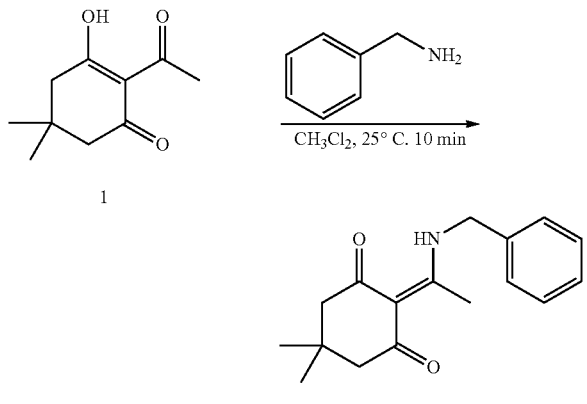

1 (1 mmol) and benzylamine (1 mmol) were dissolved in 500 μL CHCl₃ and stirred at room temperature. The reaction was monitored using TLC (silica, 3:1 Hex:EtOAc) and was determined to be complete after 10 min. The solidified mixture was dissolved in EtOAc and purified by column chromatography using n-hexane/EtOAc as the eluent (SiO$_2$, 0-50% EtOAc). Column fractions containing pure product were combined and solvent was removed under reduced pressure to yield 3 as a white solid (76% isolated yield). Characterization Data: $^1$H NMR (500 MHz, CDCl$_3$): δ 13.76 (broad s, 1H), 7.37 (m, 2H), 7.32 (m, 1H), 7.27 (m, 2H), 4.60 (d, J=5.65 Hz, 2H), 2.59 (s, 3H), 2.40 (s, 2H), 2.35 (s, 2H), 1.03 (s, 6H) ppm; $^{13}$C NMR (125 MHz, CDCl$_3$): δ 199.28, 196.89, 173.87, 135.63, 129.21, 128.19, 127.26, 108.28, 53.66, 52.37, 47.40, 30.18, 28.37, 18.21 ppm; FT-IR (neat, cm$^{-1}$) 3458, 3159, 3146, 3107, 3089, 3023, 3053, 3030, 3005, 2956, 2936, 2888, 2869, 2816, 1947, 1871, 1855, 1804, 1739, 1663, 1633, 1575, 1493, 1463, 1454, 1413, 1385, 1368, 1335, 1303, 1288, 1270, 1260, 1229, 1217, 1202, 1166, 1145, 1130, 1096, 1072, 1036, 1025, 1001, 988, 975, 941, 917, 903, 846, 824, 793, 764, 750, 733, 704, 694, 665; HRMS (ESI): m/z for C$_{17}$H$_{22}$NO$_3^+$ (MH)$^+$ calculated 272.1572, found 272.1647; analysis (calculated, found for C$_{17}$H$_{21}$NO$_3$) C (75.25, 75.04), H (7.80, 7.82), N (5.16, 5.16).

Example 4

Synthesis of Diketoenamine (4)

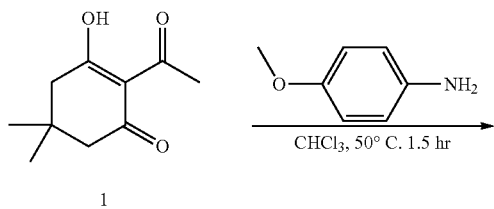

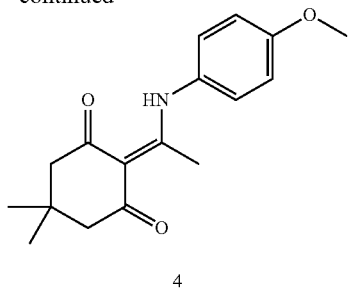

1 (1 mmol) and para-methoxyaniline (anisidine) (1 mmol) were dissolved in 500 μL CHCl$_3$ and stirred at 50° C. The reaction was monitored using TLC (silica, 1:1 Hex:EtOAc) and was determined to be complete after 1.5 hours as indicated by complete consumption of 1. The reaction mixture was purified by column chromatography (SiO$_2$, 0-50% EtOAc) and recrystallized in Hex/EtOAc to yield 4 as colorless crystals (47% isolated yield). Characterization Data: $^1$H NMR (500 MHz, CDCl$_3$): δ 14.81 (br s, 1H), 7.05 (m, 2H), 6.92 (m, 2H), 3.81 (s, 3H), 2.74 (s, 3H), 2.46 (s, 2H), 2.38 (s, 2H), 1.06 (s, 6H) ppm; $^{13}$C NMR (500 MHz, CDCl$_3$): δ 199.67, 197.09, 172.87, 159.00, 129.37, 127.06, 114.72, 108.53, 55.64, 53.74, 52.38, 30.27, 28.44, 20.31 ppm; FT-IR (neat, cm$^{-1}$): 3516, 3057, 3001, 2956, 2937, 2890, 2868, 2838, 1643, 1610, 1562, 1513, 1459, 1422, 1411, 1385, 1369, 1339, 1299, 1287, 1272, 1250, 1229, 1178, 1140, 1125, 1110, 1042, 1032, 1012, 949, 939, 928, 886, 846, 829, 768, 737, 705; HRMS (ESI) m/z for C$_{17}$H$_{22}$NO$_3^+$ (MH)$^+$ calculated 288.1572, found 288.1595; analysis (calculated, found for C$_{17}$H$_{21}$NO$_3$): C (71.06, 71.10), H (7.37, 7.19), N (4.82, 4.82).

Example 5

Synthesis of Diketoenamine (5)

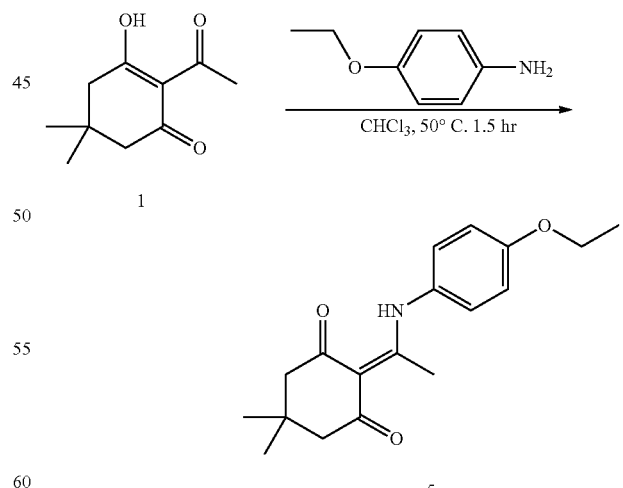

1 (1 mmol) and para-ethoxyaniline (1 mmol) were dissolved in 500 μL CHCl$_3$ and stirred at 50° C. The reaction was monitored using TLC (silica, 1:1 Hex:EtOAc) and was determined to be complete after 2 h. The reaction mixture solidified at room temperature and was recrystallized in Hex/EtOAc to yield colorless crystals (47% yield). Analytically pure samples were prepared by column chromatography with n-hexane/EtOAc as eluent (SiO$_2$, 0-30% EtOAc gradient). Characterization Data: $^1$H NMR (500 MHz, CDCl$_3$): δ 14.08 (s, 1H), 7.03 (d, J=8.8 Hz, 2H), 6.90 (d, J=8.9 Hz, 2H), 4.03 (q, J=7 Hz, 2H), 2.48 (s, 3H), 2.42 (s, 4H), 1.42 (t, J=7 Hz, 2H), 1.07 (s, 6H) ppm; $^{13}$C NMR (125 MHz, CDCl$_3$): δ 199.59, 197.04, 172.81, 158.35, 129.15, 126.98, 115.16, 108.49, 63.85, 53.70, 52.34, 30.22, 28.40, 20.28, 14.84 ppm; FT-IR (neat, cm$^{-1}$) 3265, 3074, 3046, 2976, 2955, 2936, 2867, 2543, 2488, 2356, 2224, 2075, 2030, 1968, 1901, 1687, 1637, 1609, 1575, 1510, 1455, 1420, 1408, 1394, 1387, 1367, 1342, 1298, 1287, 1248, 1228, 1173, 1141, 1118, 1090, 1049, 1006, 979, 948, 939, 925, 897, 890, 859, 846, 826, 811, 792, 764, 739, 707, 666; HRMS (ESI) m/z for C$_{18}$H$_{24}$NO$_3^+$ (MH)$^+$ calculated 302.1678, found 302.1754; analysis (calculated, found for C$_{18}$H$_{23}$NO$_3$): C (71.73, 71.74), H (7.69, 7.60), N (4.65, 4.63).

Example 6

Synthesis of Ditopic Triketone (DK6)

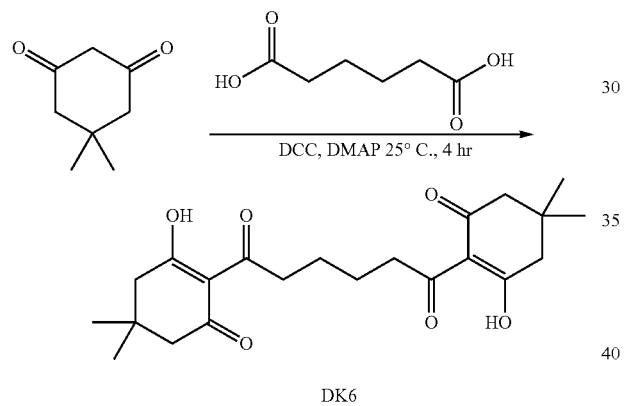

DK6

Dimedone (2.1 mol), adipic acid (1 mol) and DMAP (3 mol) were dissolved in dichloromethane (1.0 M dimedone) with stirring. A separate solution of DCC (2.4 mol) in dichloromethane (1.0 M DCC) was added slowly at room temperature to the stirring solution of dimedone, adipic acid and DMAP. The reaction was allowed to proceed 4 h with stirring at room temperature, at which point the white dicyclohexylurea precipitate was filtered off and washed with dichloromethane until completely white. The dichloromethane filtrate was collected and washed with 3% HCl until the pH of the aqueous phase was <3. The organic phase was separated, dried over MgSO$_4$, filtered and the solvent was removed under vacuum. The crude, pale yellow solid was recrystallized from ethyl acetate/hexanes to yield white crystals (90% isolated yield). Characterization Data: $^1$H NMR (500 MHz, CDCl$_3$): δ 18.17 (s, 2H), 3.06 (s, 4H), 2.51 (s, 4H), 2.33 (s, 4H), 1.69 (t, 4H), 1.06 (s, 12H) ppm; $^{13}$C NMR (125 MHz, CDCl$_3$): δ 203.37, 197.65, 195.15, 112.07, 52.71, 46.88, 40.30, 30.78, 28.30, 24.19 ppm; FT-IR (neat, cm$^{-1}$): 3302, 2956, 2933, 2894, 2871, 2736, 1746, 1656, 1621, 1548, 1466, 1457, 1438, 1422, 1406, 1389, 1367, 1325, 1311, 1291, 1256, 1246, 1173, 1149, 1130, 1067, 1048, 1017, 991, 947, 933, 918, 893, 858, 821, 789, 765, 750, 734, 660; HRMS (EI) m/z for C$_{22}$H$_{30}$O$_6$ (M) calculated 390.2042, found 390.2045; analysis (calculated, found for C$_{22}$H$_{30}$O$_6$): C (67.67, 67.82), H (7.74, 7.64).

Example 7

Synthesis of Ditopic Triketone (DK8)

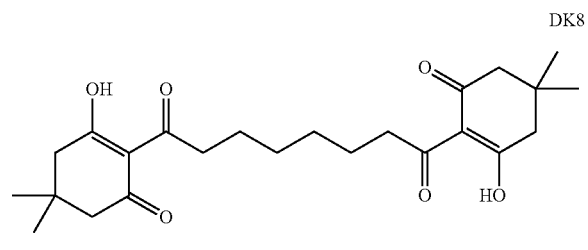

DK8 was synthesized in an identical fashion to DK6, except that suberic acid was used in place of adipic acid. Crude product was recrystallized from ethyl acetate to yield white crystals (93% isolated yield) Characterization Data: $^1$H NMR (500 MHz, CDCl$_3$): δ 18.23 (s, 2H), 3.00 (br s, 4H), 2.52 (s, 4H), 2.34 (s, 4H), 1.61 (br s, 4H), 1.39 (br s, 4H), 1.06 (s, 12H); $^{13}$C NMR (125 MHz, CDCl$_3$): δ 205.72, 197.93, 195.22, 112.07, 52.78, 47.02, 40.39, 30.79, 29.27, 28.32, 24.65; FT-IR (neat, cm$^{-1}$): 2960, 2930, 2851, 1663, 1557, 1466, 1438, 1400, 1385, 1316, 1146, 1064, 946, 923, 723. HRMS (EI) m/z for C$_{24}$H$_{34}$O$_6$ (M) calculated 418.2355, found 418.2358; analysis (calculated, found for C$_{24}$H$_{34}$O$_6$): C (68.88, 68.75), H (8.19, 8.05).

Example 8

Synthesis of Ditopic Triketone (DK10)

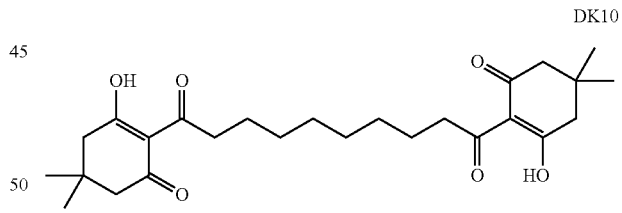

DK10 was synthesized in an identical fashion to DK6, except that sebacic acid was used in place of adipic acid. Crude product was recrystallized from ethyl acetate to yield white crystals (91% isolated yield). Characterization Data: $^1$H NMR (500 MHz, CDCl$_3$): δ 18.28 (s, 2H), 3.03 (br s, 4H), 2.55 (s, 4H), 2.37 (s, 4H), 1.62 (br s, 4H), 1.34 (br s, 8H), 1.12 (s, 12H); $^{13}$C NMR (125 MHz, CDCl$_3$): δ 205.83, 197.94, 195.22, 112.06, 52.07, 47.04, 40.44, 30.78, 29.44, 29.40, 28.31, 24.79; FT-IR (neat, cm$^{-1}$): 2959, 2940, 2915, 2872, 1657, 1565, 1463, 1437, 1418, 1402, 1390, 1369, 1324, 1308, 1286, 1200, 1167, 1149, 1124, 1039, 1019, 1000, 949, 894, 864, 756. HRMS (EI) m/z for C$_{26}$H$_{38}$O$_6$ (M) calculated 446.2668, found 446.2669; analysis (calculated, found for C$_{26}$H$_{38}$O$_6$): C (69.93, 69.75), H (8.58, 8.31).

Example 9

Synthesis of Ditopic Triketone (DL10)

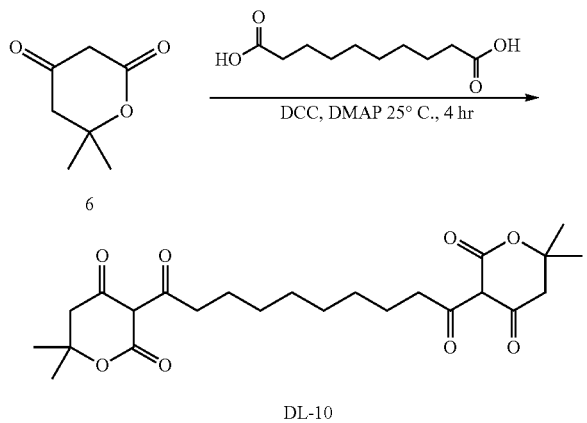

DL-10

Ketolactone 6 (2.1 mol), sebacic acid (1 mol) and DMAP (3 mol) were dissolved in dichloromethane (1.0 M LACTONE) with stirring. A separate solution of DCC (2.4 mol) in dichloromethane (1.0 M DCC) was added slowly at room temperature to the stirring solution of 6, sebacic acid and DMAP. The reaction was allowed to proceed 4 h with stirring at room temperature, at which point the white dicyclohexylurea precipitate was filtered off and washed with dichloromethane until completely white. The dichloromethane filtrate was collected and washed with 3% HCl until the pH of the aqueous phase was <3. The organic phase was separated, dried over $MgSO_4$, filtered and the solvent was removed under vacuum. The crude, pale yellow solid was recrystallized from ethyl acetate/hexanes to yield white crystals (90% isolated yield). Characterization Data: $^1$H NMR (500 MHz, $CDCl_3$): Two isomers are present in a roughly 4:1 ratio. [Isomer 1, major component] δ 17.96 (s, 2H), 3.03 (m, 4H), 2.70 (s, 4H), 1.65 (m, 4H), 1.46 (s, 12H), 1.36 (br m, 4H), 1.32 (br m, 4H) ppm; [Isomer 2, minor component]δ 16.28 (s, 2H), 2.62 (s, 4H), 2.35 (m, 4H), 1.65 (m, 4H), 1.47 (s, 12H), 1.36 (br m, 4H), 1.32 (br m, 4H) ppm.

Example 10

Synthesis of Ditopic Triketone (BA10)

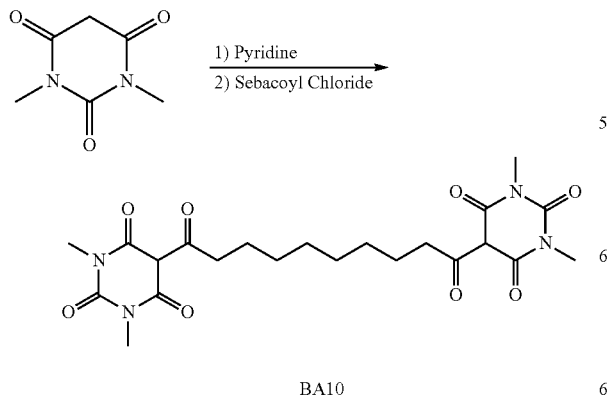

BA10

1,3-dimethylbarbituric acid (10 g, 64 mmol) dissolved acid in pyridine, cooled to 0° C., and sebacoyl chloride (7.5 g, 31 mmol) was added drop-wise to the vigorous stirring. Immediately, an off-white solid precipitates from the pale yellow solution. The reaction was warmed to room temperature and allowed to proceed an additional 15 min. The reaction mixture was again cooled to 0° C. and 3% HCl was added slowly until a pH of <3 was reached. The off-white solid that had precipitated was filtered, and dried under vacuum. The crude product (95% isolated yield) showed no detectable impurities by $^1$H NMR and was used as prepared. Characterization Data: $^1$H NMR (500 MHz, $CDCl_3$): δ 17.52 (s, 2H), 3.36 (s, 6H), 3.12 (t, 4H, J=7.6 Hz), 1.68 (m, 4H), 1.41 (m, 4H), 1.34 (m, 4H) ppm; HRMS (ESI) m/z for $C_{22}H_{29}O_8N_4^-$ (M-H)$^-$ calculated 477.1991, found 477.1982.

Example 11

Synthesis of Ditopic Triketone DIMER (MA10)

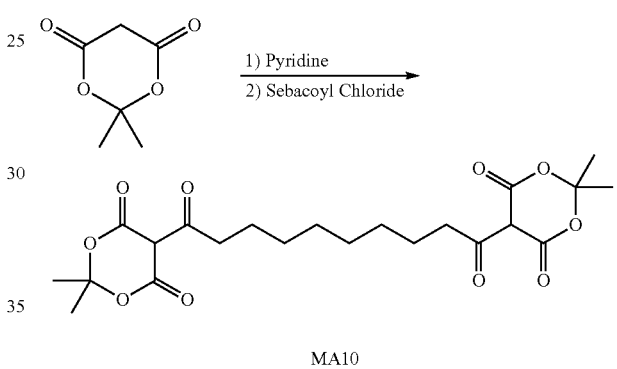

MA10

MA10 was synthesized in an identical fashion to BA10, except that Meldrum's acid was used instead of 1,3-dimethylbarbituric acid. The crude product was purified by extracting MA10 into aqueous $K_2CO_3$, filtering off undissolved solids and precipitating the MA10 monomer from HCl aq. (pH<3). The light yellow solid was recrystallized from ethyl acetate to yield yellow needle-shaped crystals (75% isolated yield). Characterization Data: $^1$H NMR (500 MHz, $CDCl_3$): δ 15.30 (s, 2H), 3.06 (t, 4H, J=7.65 Hz), 1.73 (s, 12H), 1.69 (m, 4H), 1.41 (m, 4H), 1.34 (m, 4H) ppm; HRMS (ESI) m/z for $C_{22}H_{29}O_{10}^-$ (M-H)$^-$ calculated 453.1766, found 453.1757.

Example 12

Synthesis of Diketoenamine-Based Linear or Branched Polymers

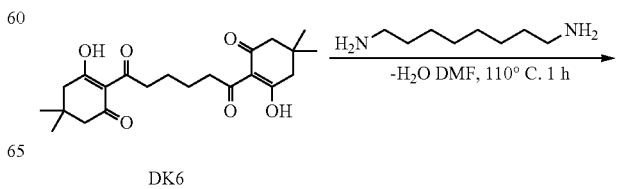

DK6

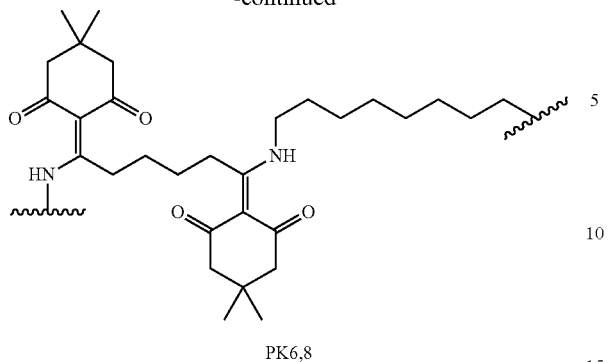

PK6,8

The general procedure for synthesizing all linear polymers involved dissolving DK6, DK8, or DK10 (1 mmol) in N,N-dimethylformamide (0.4 mL, 2.5 M) at 110° C., with gentle stirring. 1,4-diaminooctane (DAO) (1 mmol) was added at once to the stirring triketone solution, forming a viscous solution immediately. The polymerization was allowed to proceed with gentle stirring, in an open container to facilitate water removal at 110° C. for 1 h. The reaction mixture was then cooled to room temperature, diluted using dichloromethane, and precipitated from diethyl ether. The precipitate was collected by centrifugation, dissolved in dichloromethane, and precipitated from diethyl ether two more times. The collected precipitate was dried under vacuum and characterized using SEC, and DSC and $^1$H NMR.

Example 13

Characterization of Linear Polymer (Pk6,8)

Characterization Data: $^1$H NMR (500 MHz, CDCl$_3$): δ 13.45 (m, 2H), 3.44 (m, 4H), 3.03 (m, 4H), 2.37 (br s, 4H), 2.31 (br s, 4H), 1.68 (m, 8H), 1.43 (m, 4H), 1.36 (m, 4H), 1.01 (s, 12H) ppm. Size Exclusion Chromatography (Solvent=THF): Mw=29,000 g mol$^{-1}$, Mn=22,000 g mol$^{-1}$, PDI=1.28. Glass Transition Temperature (DSC)=65° C.

Example 14

Characterization of Linear Polymer (Pk8,8)

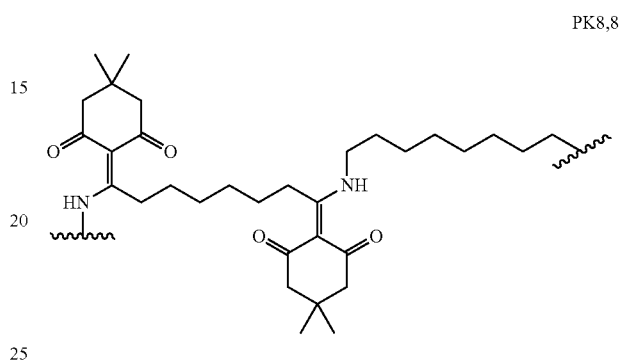

PK8,8

Characterization Data: $^1$H NMR (500 MHz, CDCl$_3$): δ 13.41 (m, 2H), 3.40 (q, 4H), 2.96 (m, 4H), 2.37 (br s, 4H), 2.31 (br s, 4H), 1.67 (p, 4H), 1.53 (br s, 8H), 1.43 (m, 4H), 1.37 (m, 4H), 1.01 (s, 12H) ppm. Size Exclusion Chromatography (Solvent=THF): Mw=81,000 g mol$^{-1}$, Mn=65,000 g mol$^{-1}$, PDI=1.25. Glass Transition Temperature (DSC)=55° C.

Example 15

Characterization of Linear Polymer (PK10,8)

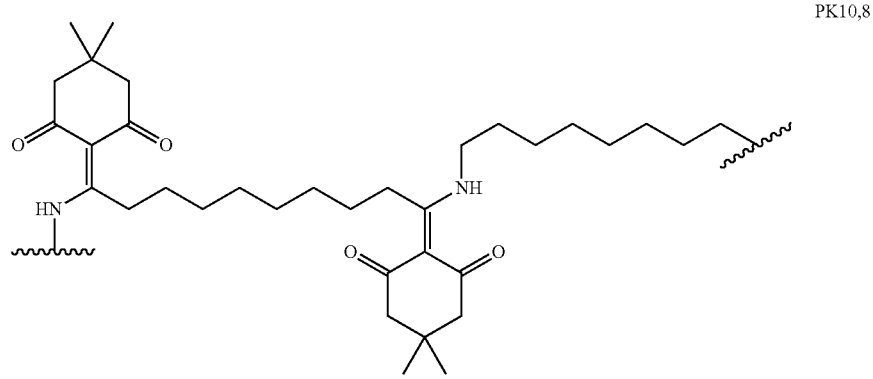 [SMILES: *CCCCCCCCNC(CCCCCCCCC(N*)=C1C(=O)CC(C)(C)CC1=O)=C1C(=O)CC(C)(C)CC1=O]

PK10,8

Characterization Data: $^1$H NMR (500 MHz, CDCl$_3$): δ 13.45 (m, 2H), 3.39 (q, 4H), 2.94 (m, 4H), 2.35 (br s, 4H), 2.32 (br s, 4H), 1.67 (p, 4H), 1.51 (m, 4H), 1.46 (m, 8H), 1.37 (m, 8H), 1.01 (s, 12H) ppm. Size Exclusion Chromatography (Solvent=THF): Mw=165,000 g mol$^{-1}$, Mn=117,000 g mol$^{-1}$, PDI=1.41. Glass Transition Temperature (DSC)=40° C.

Example 16

Synthesis of Diketoenamine-Based Linear or Network Polymers

The general procedure for synthesizing all network polymers involved first weighing out the appropriate amount of ditopic triketone monomer and placing the powder at the bottom of the ball mill, along with the ball bearings. To the ditopic triketone monomer was added one or more polyamines, which was (were) immediately followed by ball-milling the contents of the closed container in 15 min intervals. In general, no solvent is required to induce efficient polymerization, however, it was found that the rubber-like polymer PK6(TREN:PPG) would become increasingly viscous and sticky after ~15 min of ball-milling, completely arresting all of the bearings and preventing further reactivity. In this case, it was found that a small amount of dichloromethane was useful in lubricating the contents of the container to ensure the mobility of the bearings, allowing the reaction to progress (specific reaction details below).

Example 17

Controlling Network Density by Ball Milling

DK6 (1.0 g, 2.5 mmol) was placed in a ball mill along with TREN, at either 0.9 eq. amine (0.225 g, 1.54 mmol), 1.0 eq. amine (0.250 g, 1.71 mmol), 1.1 eq. amine (0.275 g, 1.88 mmol) or 1.2 eq. amine (0.300 g, 2.05 mmol). The mixture of DK6 and TREN was ball milled in 15 min intervals. After each 15-minute interval, 100 mg of material was removed from the reaction for solid-state NMR (FIG. 13), DSC (FIG. 14), and gel-fraction (FIG. 15) analyses.

Example 18

Procedure for the Large-Scale Synthesis of PK6(TREN)

Figure 16:
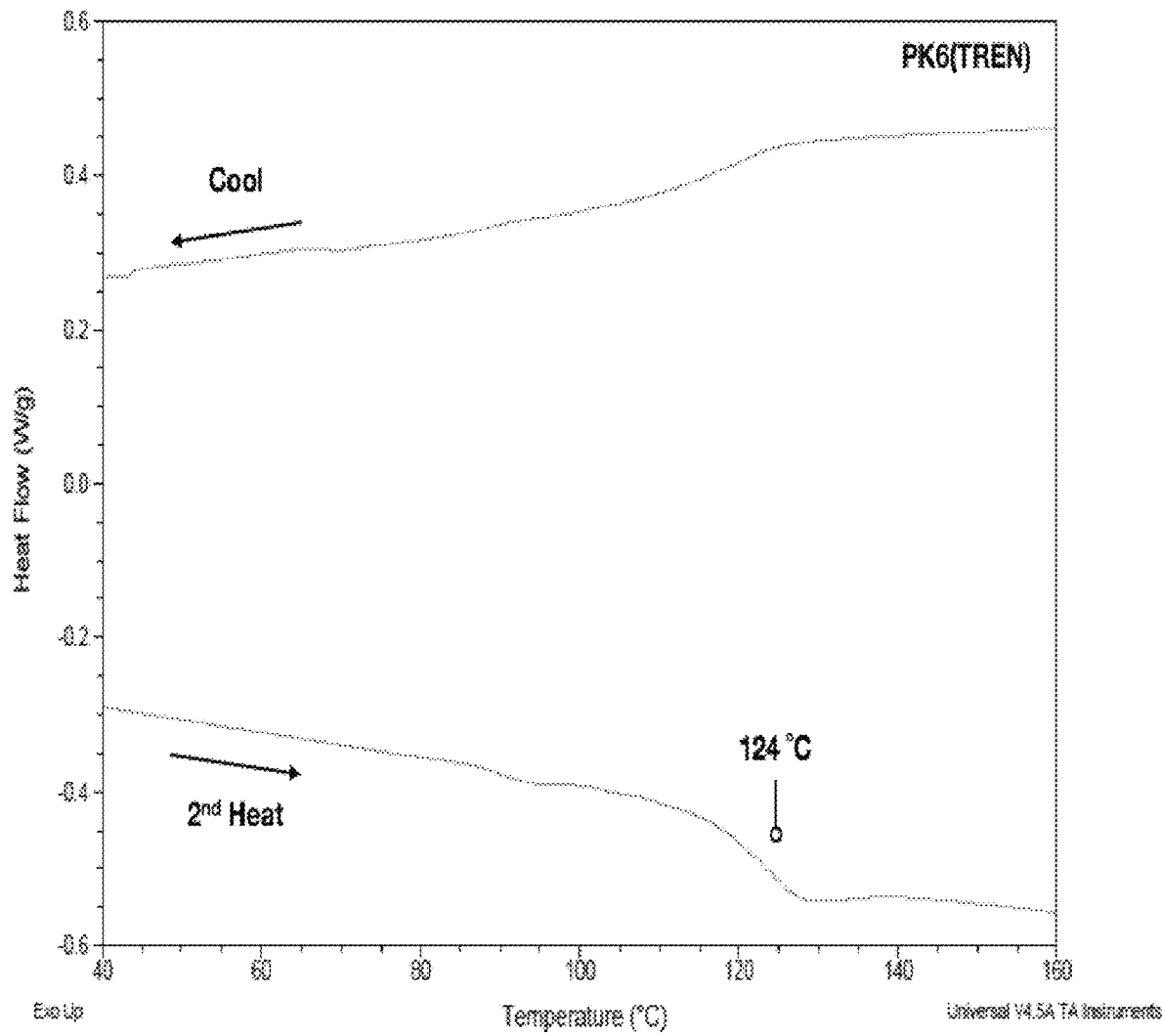
FIG. 16. Heat flow versus temperature for PK6(TREN).

DK6 (10.0 g, 25.6 mmol) was ball milled along with TREN (2.75 g, 18.8 mmol). The reaction was ball milled in 15 min increments until no further changes were observed in the glass transition temperature (FIG. 16). Reaction completion was further confirmed using solid-state NMR. The material was obtained as an off-white powder.

Example 19

Procedure for the Large-Scale Synthesis of PK6(TREN:ODA)

Figure 17:
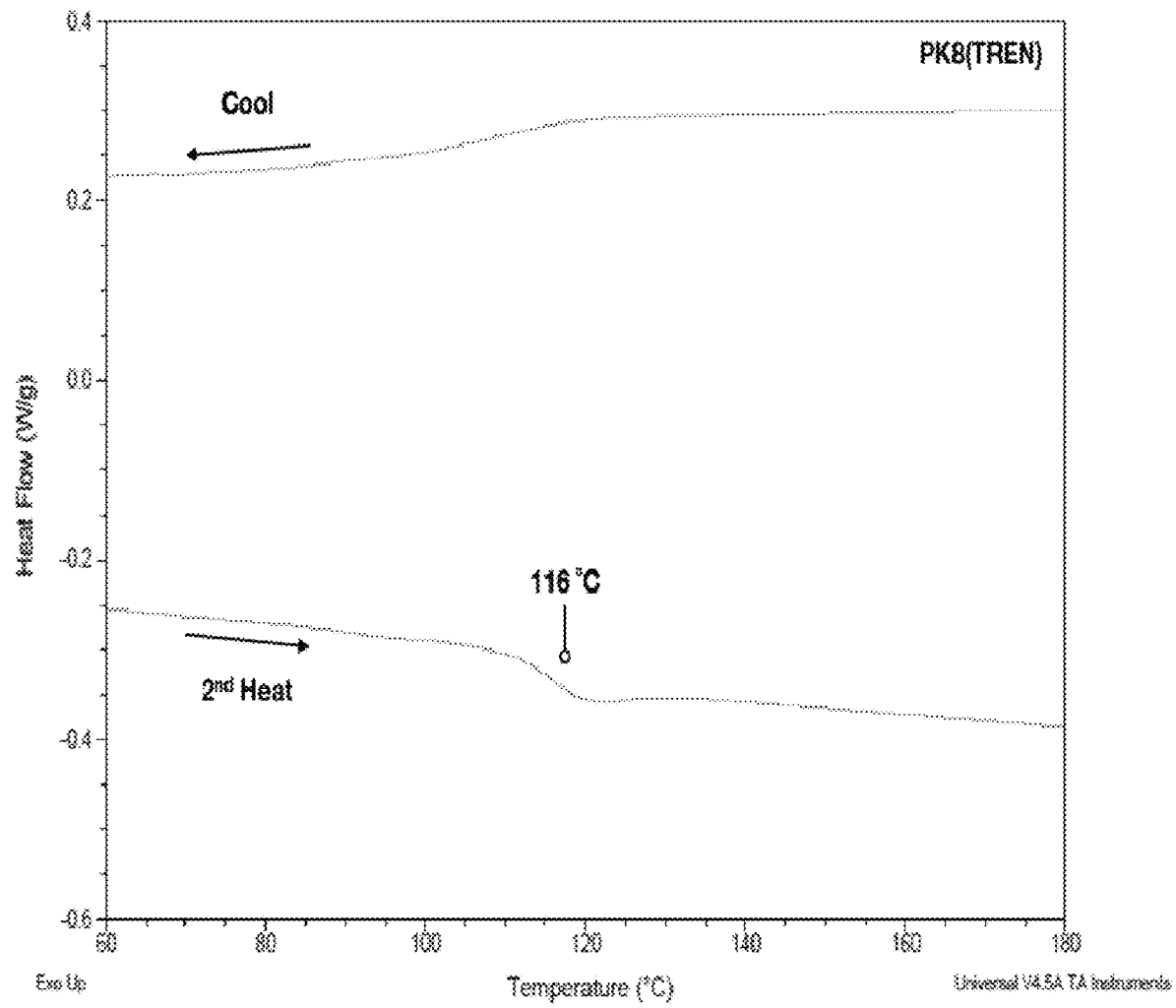
FIG. 17. Heat flow versus temperature for PK8(TREN).
Figure 18:
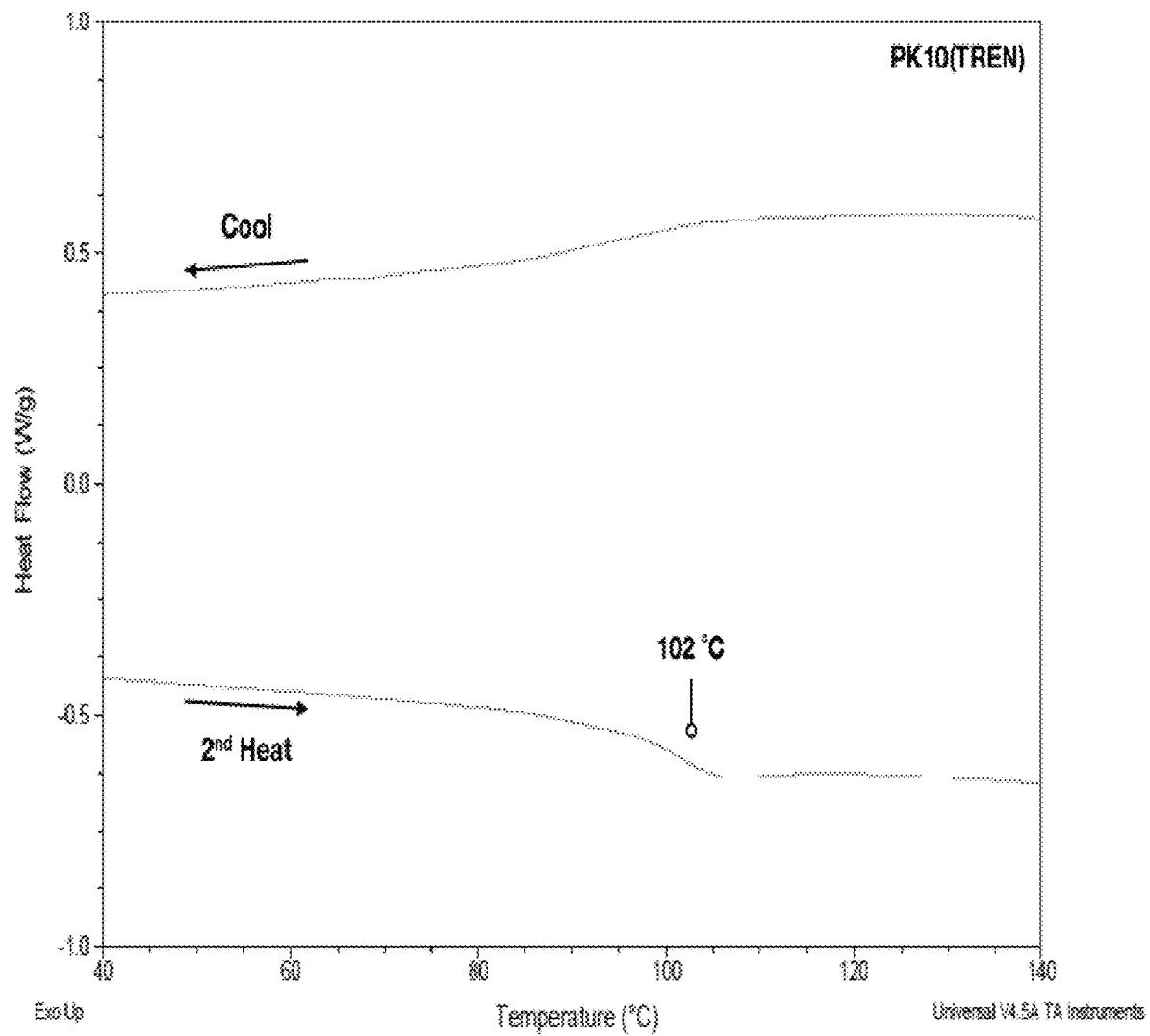
FIG. 18. Heat flow versus temperature for PK10(TREN).

DK6 (10.0 g, 25.6 mmol) was ball milled along with TREN (1.92 g, 13.2 mmol, 70 mol % total amine) and 4,4'-oxydianiline (1.69 g, 8.5 mmol, 30 mol % total amine). The reaction was ball milled in 15 min increments until no further changes were observed in the glass transition temperature (FIG. 17). Reaction completion was further confirmed using solid-state NMR. The obtained material was an off-white powder much like polymer 3.

Example 20

Procedure for the Large-Scale Synthesis of PK6(TREN:PPG)

Triketone monomer 2 (5.0 g, 12.8 mmol) was ball milled along with TREN (1.24 g, 8.45 mmol, 90 mol % total amine) and poly(propylene glycol) bis(2-aminopropyl ether) M$_n$~2000 (2.82 g, 1.41 mmol, 10 mol % total amine). The dimer and amine mixture were separately dissolved in ~1 mL dichloromethane each and the solutions were mixed together in the ball mill. The reaction was ball milled in 15-min increments until no further changes were observed in the glass transition temperature. The material, when dry, is an off-white clay-like solid.

Example 21

Figure 38:
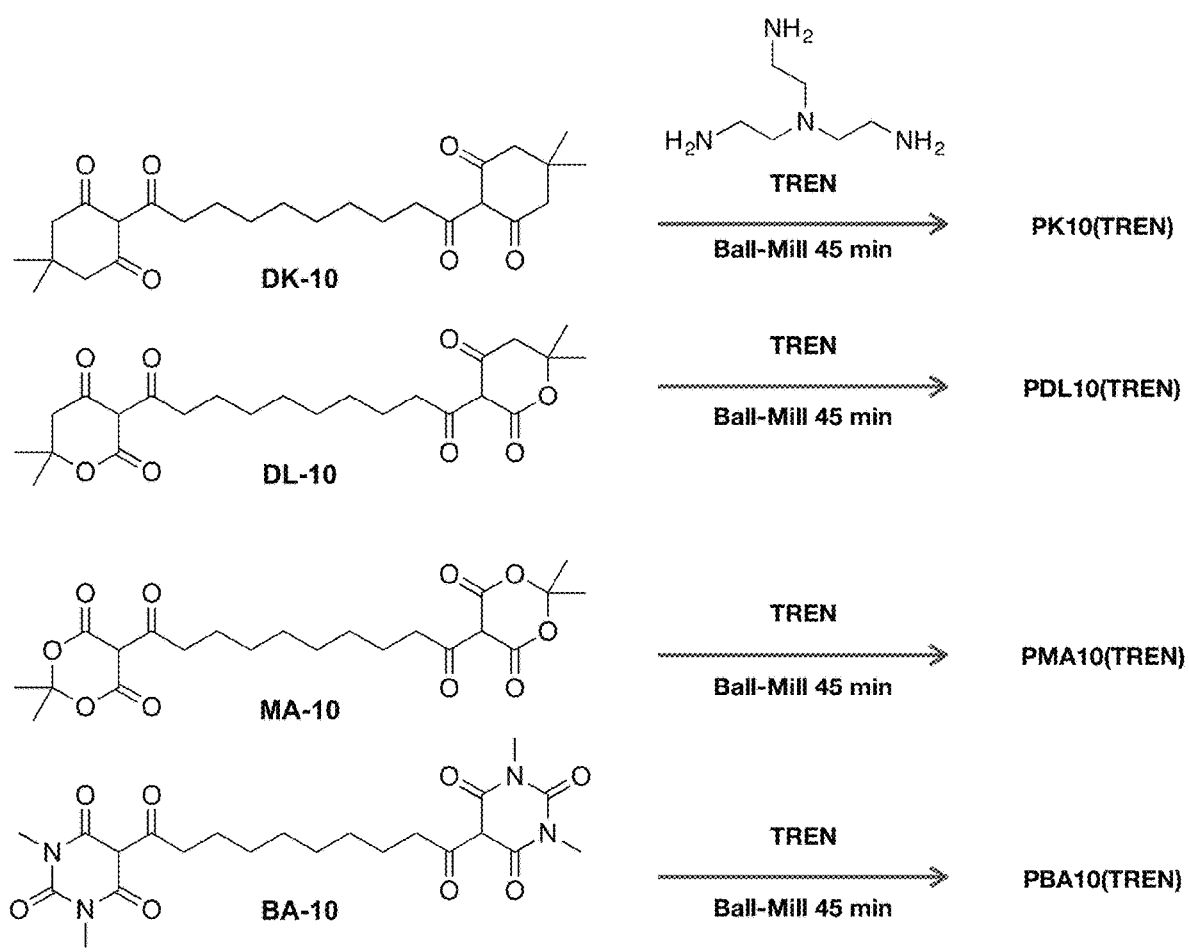
FIG. 38. Reactions for PK10(TREN), PDL10(TREN), PMA10(TREN), and PBA10(TREN).
Figure 39:
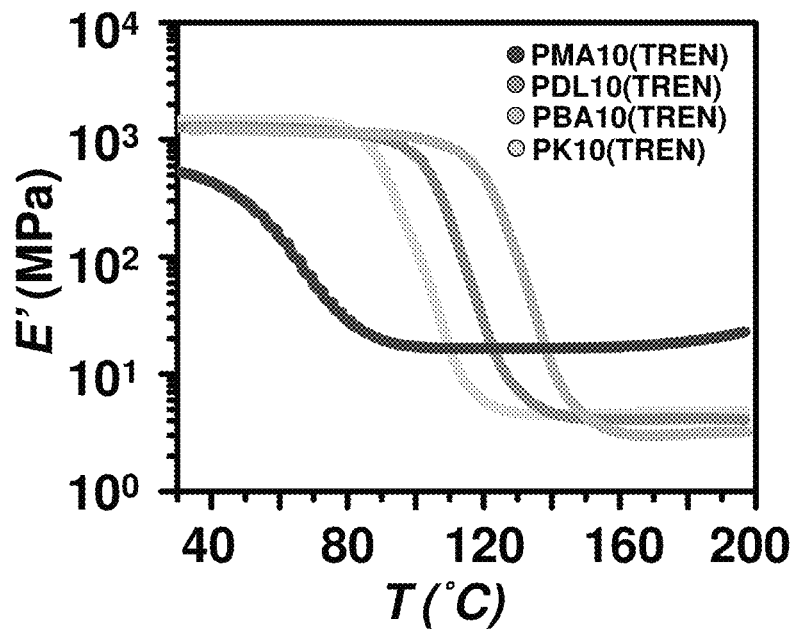
FIG. 39. E' versus temperature for PK10(TREN), PDL10(TREN), PMA10(TREN), and PBA10(TREN).
Figure 40:
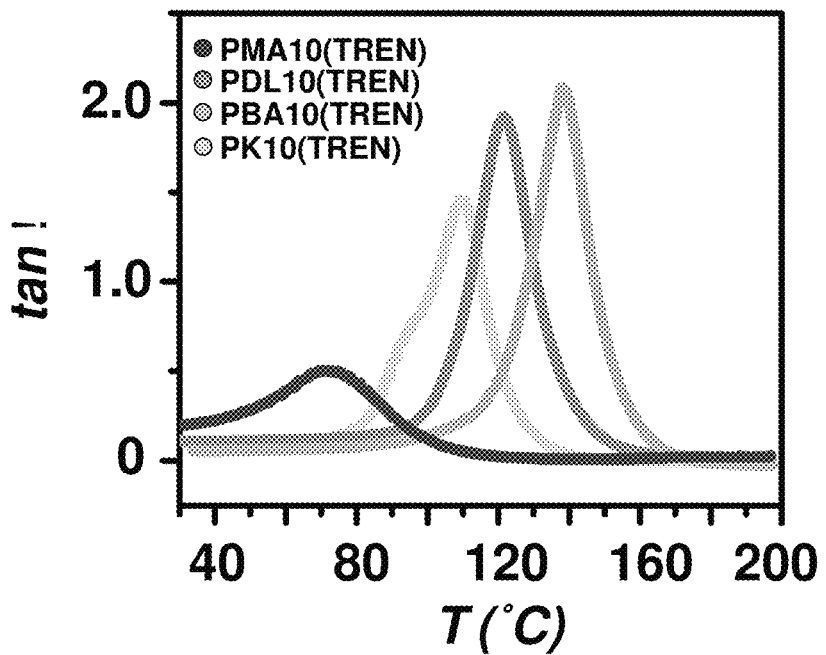
FIG. 40. tan ! versus temperature for PK10(TREN), PDL10(TREN), PMA10(TREN), and PBA10(TREN)

Formulation and Thermomechanical Properties of Poly(Diketoenamine)s from Heteroatom-Containing Triketone Monomers The general procedure for synthesizing poly(diketoenamine) polymers from heteroatom-containing triketone monomers involves ball-milling heteroatom-containing triketone monomers (including but not limited to DL10, MA10, and/or BA10 (FIG. 38)) with polytopic amines, including, but not limited to TREN. Generally speaking, the triketone monomer was polymerized with TREN in a ball mill for 45 min to yield the polymer as a fine powder. Dynamic mechanical analysis (DMA) of DL10, MA10, and BA10 (FIG. 39 and FIG. 40) show very similar storage moduli at room temperature (E'=1.2-1.5 GPa), except for PMA10(TREN) which shows a lower storage modulus (E' ~500 MPa). The glass transition temperature, as indicated by the maximum value obtained from the tan □ data obtained using DMA (FIG. 40) ranges from ~75° C. to >130° C. for polymer formulations containing different heteroatom substitution patterns for the various monomer repeat units.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising a polymer, or polymer network, having at least one unit of the formula (I), (II), (III), (IV), (V), (VI), (VII), (VIII), (IX), (X), (XI), (XII), (XIII), (XIV), (XV), (XVI), (XVII), (XVIII), (XIX), and/or (XX), or a mixture thereof;

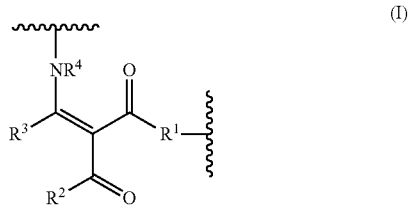

-continued
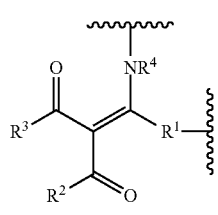
(II)
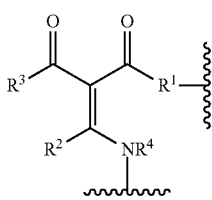
(III)
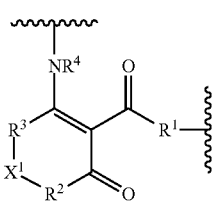
(IV)
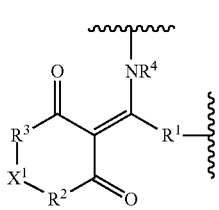
(V)
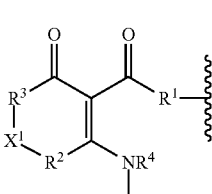
(VI)
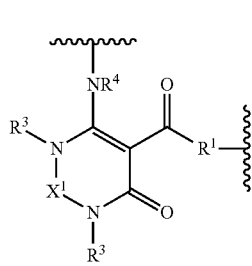
(VII)
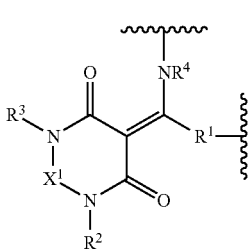
(VIII)
-continued
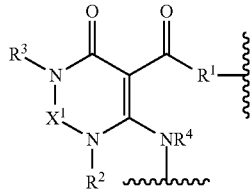
(IX)
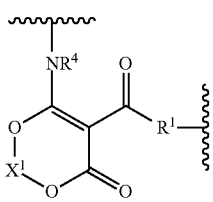
(X)
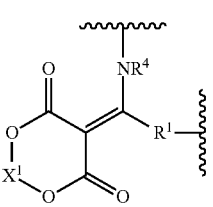
(XI)
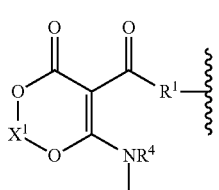
(XII)
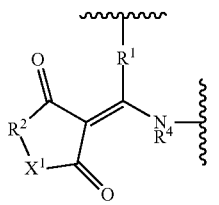
(XIII)
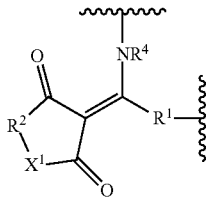
(XIV)
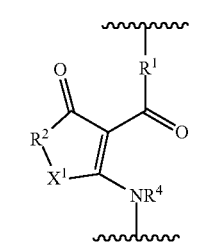
(XV)

-continued
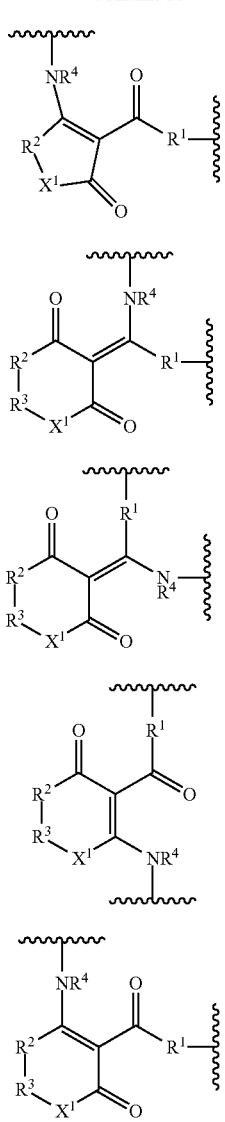
(XVI)
(XVII)
(XVIII)
(XIX)
(XX)
wherein said polymer, or polymer network, is obtained by connecting one compound Y comprising at least two functional groups selected from the group (A), (B), (C), (D), (E), (F), (G), (H), (I), (J), (K), (L), (M), (N), (O), (P), (Q), (R), (S), (T), (U), (V), and/or (W), or a mixture thereof;
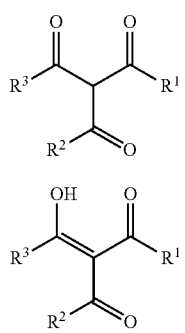
(A)
(B)
-continued
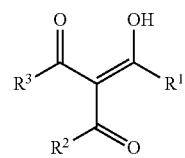
(C)
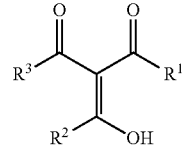
(D)
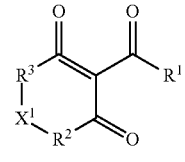
(E)
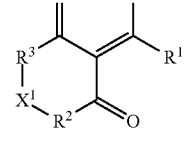
(F)
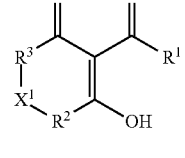
(G)
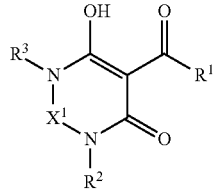
(H)
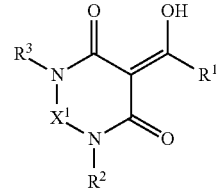
(I)
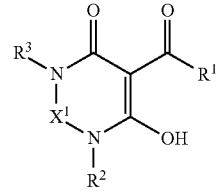
(J)
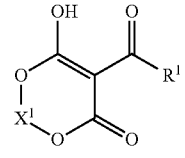
(K)

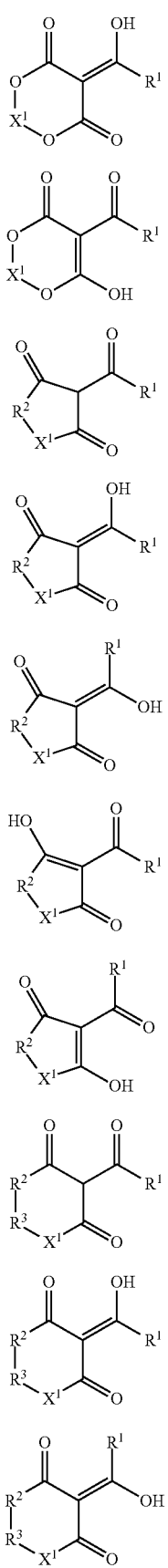
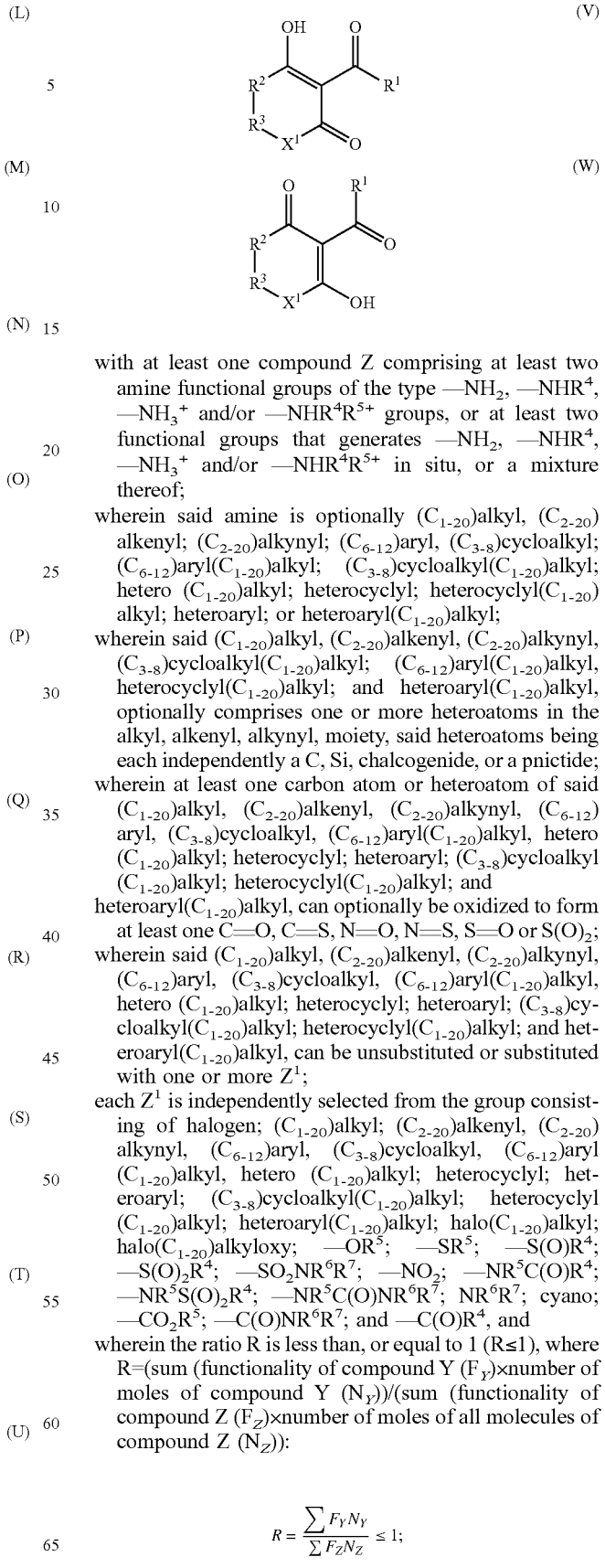

with at least one compound Z comprising at least two amine functional groups of the type —$NH_2$, —$NHR^4$, —$NH_3^+$ and/or —$NHR^4R^{5+}$ groups, or at least two functional groups that generates —$NH_2$, —$NHR^4$, —$NH_3^+$ and/or —$NHR^4R^{5+}$ in situ, or a mixture thereof;

wherein said amine is optionally ($C_{1-20}$)alkyl, ($C_{2-20}$)alkenyl; ($C_{2-20}$)alkynyl; ($C_{6-12}$)aryl, ($C_{3-8}$)cycloalkyl; ($C_{6-12}$)aryl($C_{1-20}$)alkyl; ($C_{3-8}$)cycloalkyl($C_{1-20}$)alkyl; hetero ($C_{1-20}$)alkyl; heterocyclyl; heterocyclyl($C_{1-20}$)alkyl; heteroaryl; or heteroaryl($C_{1-20}$)alkyl;

wherein said ($C_{1-20}$)alkyl, ($C_{2-20}$)alkenyl, ($C_{2-20}$)alkynyl, ($C_{3-8}$)cycloalkyl($C_{1-20}$)alkyl; ($C_{6-12}$)aryl($C_{1-20}$)alkyl, heterocyclyl($C_{1-20}$)alkyl; and heteroaryl($C_{1-20}$)alkyl, optionally comprises one or more heteroatoms in the alkyl, alkenyl, alkynyl, moiety, said heteroatoms being each independently a C, Si, chalcogenide, or a pnictide;

wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero ($C_{1-20}$)alkyl; heterocyclyl; heteroaryl; ($C_{3-8}$)cycloalkyl ($C_{1-20}$)alkyl; heterocyclyl($C_{1-20}$)alkyl; and heteroaryl($C_{1-20}$)alkyl, can optionally be oxidized to form at least one C=O, C=S, N=O, N=S, S=O or $S(O)_2$;

wherein said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero ($C_{1-20}$)alkyl; heterocyclyl; heteroaryl; ($C_{3-8}$)cycloalkyl($C_{1-20}$)alkyl; heterocyclyl($C_{1-20}$)alkyl; and heteroaryl($C_{1-20}$)alkyl, can be unsubstituted or substituted with one or more $Z^1$;

each $Z^1$ is independently selected from the group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl ($C_{1-20}$)alkyl, hetero ($C_{1-20}$)alkyl; heterocyclyl; heteroaryl; ($C_{3-8}$)cycloalkyl($C_{1-20}$)alkyl; heterocyclyl ($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$; —$S(O)_2R^4$; —$SO_2NR^6R^7$; —$NO_2$; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$, and wherein the ratio R is less than, or equal to 1 (R≤1), where R=(sum (functionality of compound Y ($F_Y$)×number of moles of compound Y ($N_Y$))/(sum (functionality of compound Z ($F_Z$)×number of moles of all molecules of compound Z ($N_Z$)):

$$R = \frac{\sum F_Y N_Y}{\sum F_Z N_Z} \leq 1;$$

wherein $R_1$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or S(O)$_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$, —NR$^5$C(O)NR$^6$R$^7$; NR$^6$R$^7$; cyano; —CO$_2$R$^5$; —C(O)NR$^6$R$^7$; and —C(O)R$^4$; and wherein $R_2$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenid), or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or S(O)$_2$;

wherein said $(C_{1-20})$alkyl, $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$; and wherein $R^2$ and $R^3$ are optionally directly bonded together to form a, 5 membered cycloalkyl, heterocyclyl, or heteroaryl;

wherein $R^2$ and $R^3$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is independently optionally substituted with one or more $Z^2$ wherein each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$, —S(O)$_2$R$^4$; —SO$_2$NR$^5$R$^6$; nitro; —NR$^5$C(O)R$^4$; —NR$^5$S(O)$_2$R$^4$, —NR$^5$C(O)NR$^6$R$^7$; NR$^6$R$^7$; cyano; —CO$_2$R$^5$; —C(O)NR$^6$R$^7$; and —C(O)R$^4$;

wherein $R^2$ and $R_1$ are optionally directly bonded together to form a, 5 membered cycloalkyl, heterocyclyl, or heteroaryl;

wherein $R^2$ and $R_1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein $X^1$ and $R^2$ are optionally directly bonded together to form a, 5, 6, 7, or 8 membered heterocyclyl, or heteroaryl;

wherein $X^1$ and $R^3$ are optionally directly bonded together to form a, 5, 6, 7, or 8 membered cycloalkyl, heterocyclyl, or heteroaryl;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^5$R$^6$; nitro; —NR$^5$C(O)R$^4$; —NRSS(O)$_2$R$^4$; —NR$^5$C(O)NR$^6$R$^7$; NR$^6$R$^7$; cyano; —CO$_2$R$^5$; —C(O)NR$^6$R$^7$; and —C(O)R$^4$, wherein $R_3$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictide;

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl ($C_{1-20}$)alkyl; heterocyclyl($C_{1-20}$)alkyl; and heteroaryl($C_{1-20}$)alkyl; is optionally oxidized to form at least one C=O, C=S, N=O, N=S, S=O or S(O)$_2$;

wherein said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; and heteroaryl($C_{1-20}$)alkyl; is unsubstituted or substituted with one or more $Z^1$;

wherein each $Z^1$ is independently selected from the group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$; —$S(O)_2R^4$; —$SO_2NR^6R^7$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$, and wherein $R^3$ and $R^1$ are optionally directly bonded together to form a, 5 membered cycloalkyl, heterocyclyl, or heteroaryl;

wherein $R^3$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Se), or a pnictide (such as N, or P);

wherein each said heterocyclyl; or heteroaryl is optionally substituted with one or more $Z^2$ where each $Z^2$ is independently selected from the following group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$, —$S(O)_2R^4$; —$SO_2NR^5R^6$; nitro; —$NR^5C(O)R^4$; —$NR^5S(O)R^4$; —$NR^5C(O)NR^6R^7$; $NR^6R^7$; cyano; —$CO_2R^5$; —$C(O)NR^6R^7$; and —$C(O)R^4$ wherein $R^3$ is linked to $R^1$ with a linker $X^1$ to form a 4, 5, 6, or 7 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is optionally substituted with one or more $Z^2$ where each $Z^2$ is independently selected from the following group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$, —$S(O)_2R^4$; —$SO_2NR^5R^6$; nitro; —$NR^5C(O)R^4$; —$NR^5S(O)$; $R^4$; —$NR^5C(O)NR^6R^7$; $NR^6R^7$; cyano; —$CO_2R^5$; —$C(O)NR^6R^7$; and —$C(O)R^4$;

each $R^4$ is independently selected from the group consisting of hydrogen, $C_{(1-20)}$alkyl, $C_{(2-20)}$alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)akyl; and heteroaryl($C_{1-20}$)alkyl;

wherein said ($C_{1-20}$)alkyl, ($C_{2-20}$)alkenyl, ($C_{2-20}$)alkynyl, ($C_{6-12}$)aryl($C_{1-20}$)alkyl, heterocyclyl($C_{1-20}$)alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^5$ is independently selected from the group consisting of hydrogen, ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{6-12}$)aryl($C_{1-20}$)alkyl, heterocyclyl($C_{1-20}$)alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^6$ and $R^7$ is independently selected from the group consisting of hydrogen; ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{3-8}$)cycloalkyl($C_{1-20}$)alkyl; ($C_{6-12}$)aryl($C_{1-20}$)alkyl, heterocyclyl($C_{1-20}$)alkyl; and heteroaryl($C_{1-20}$)alkyl, optionally comprises one or more heteroatoms in the alkyl, alkenyl, alkynyl moiety, each heteroatom is independently a C, Si, chalcogenide, or a pnictide;

and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

or wherein $R^6$ and $R^7$ together with the atom to which they are attached form a 5-, 6-, or 7-membered heterocyclyl.

2. A method for synthesizing a polymer from one or more precursors in one or more solvents, said method comprising:

(a) dissolving, dispersing, or suspending one or more precursors individually in the same solvent, or individually in different and/or separate solvents, optionally with one or more surfactants;

(b) optionally heating the solvent or one or more solvents of the different and/or separate solvents;

(c) mixed the solvent comprising the one or more precursors together to form a polymer; wherein said polymer has at least one unit of the formula (I), (II), (III), (IV), (V), (VI), (VII), (VIII), (IX), (X), (XI), (XII), (XIII), (XIV), (XV), (XVI), (XVII), (XVIII), (XIX), and/or (XX), or a mixture thereof;

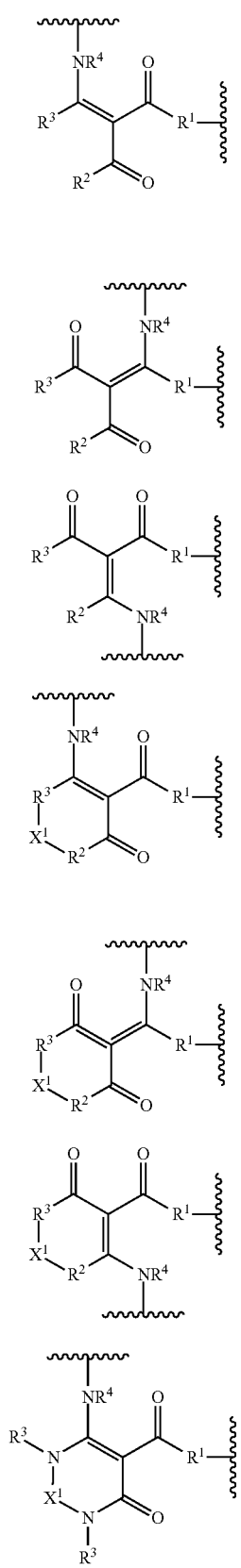
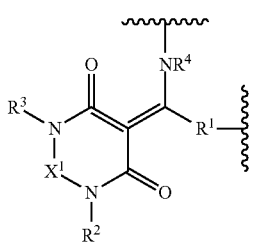
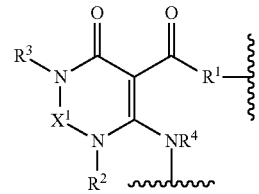
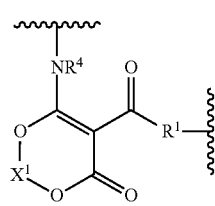
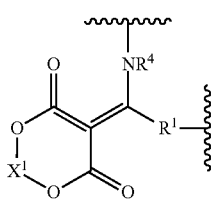
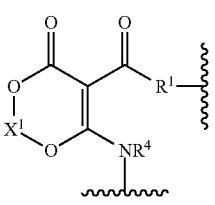
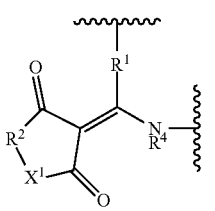
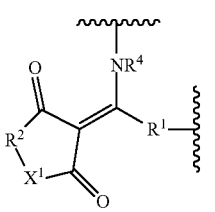

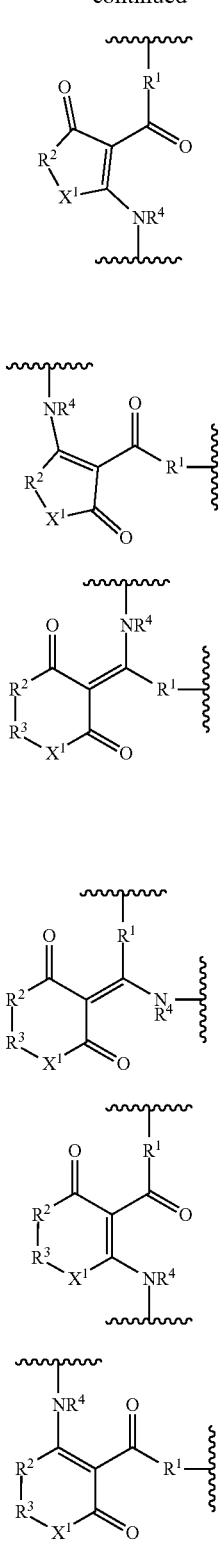
(XV)
(XVI)
(XVII)
(XVIII)
(XIX)
(XX)
wherein said polymer, or polymer network, is obtained by connecting one compound Y comprising at least two functional groups selected from the group (A), (B), (C), (D), (E), (F), (G), (H), (I), (J), (K), (L), (M), (N), (O), (P), (Q), (R), (S), (T), (U), (V), and/or (W), or a mixture thereof;
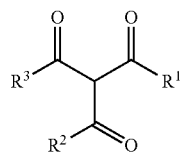
(A)
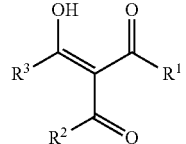
(B)
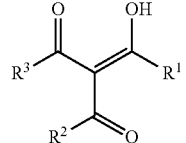
(C)
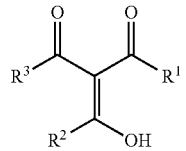
(D)
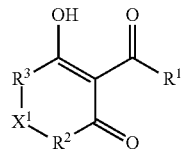
(E)
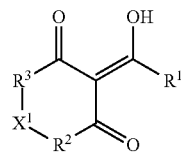
(F)
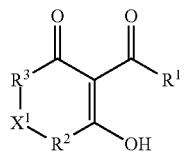
(G)
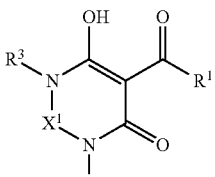
(H)
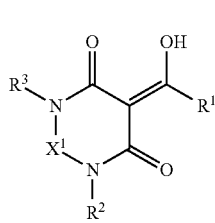
(I)

(J) 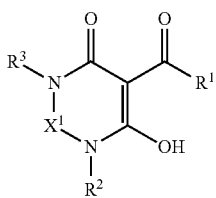

(K) 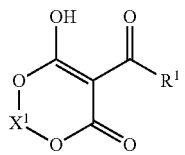

(L) 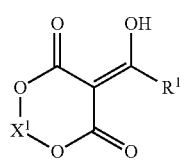

(M) 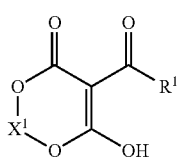

(N) 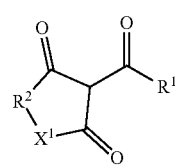

(O) 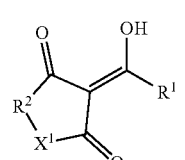

(P) 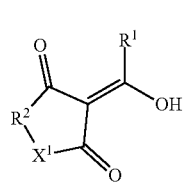

(Q) 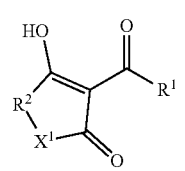

(R) 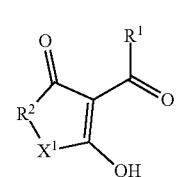

(S) 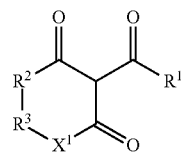

(T) 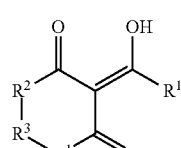

(U) 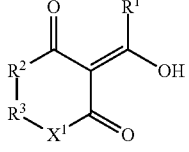

(V) 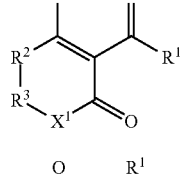

(W) 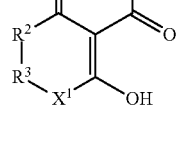

with at least one compound Z comprising at least two amine functional groups of the type —NH$_2$, —NHR$^4$, —NH$_3^+$ and/or —NHR$^4$R$^{5+}$ groups, or at least two functional groups that generates —NH$_2$, —NHR$^4$, —NH$_3^+$ and/or —NHR$^4$R$^{5+}$ in situ, or a mixture thereof;

wherein said amine is optionally (C$_{1-20}$)alkyl, (C$_{2-20}$)alkenyl), (C$_{2-20}$)alkynyl; (C$_{6-12}$)aryl, (C$_{3-8}$)cycloalkyl; (C$_{6-12}$)aryl(C$_{1-20}$)alkyl; (C$_{3-8}$)cycloalkyl(C$_{2-20}$)alkyl; hetero(C$_{1-20}$)alkyl; heterocyclyl; heterocyclyl(C$_{1-20}$)alkyl; heteroaryl; or heteroaryl(C$_{1-20}$)alkyl;

wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl, moiety, said heteroatoms being each independently a C, Si, chalcogenide, or a pnictide;

wherein at least one carbon atom or heteroatom of said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and heteroaryl(C$_{1-20}$)alkyl; can optionally be oxidized to form at least one C=O, C=S, N=O, N=S, S=O or S(O);

wherein said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and heteroaryl(C$_{1-20}$)alkyl; can be unsubstituted or substituted with one or more Z$^1$;

each Z$^1$ is independently selected from the group consisting of halogen: (C$_{1-20}$)alkyl; (C$_{2-20}$)alkenyl, (C$_{2-20}$)

alkynyl, $(C_{6-12})$aryl, $(C_{3-8})$cycloalkyl, $(C_{6-12})$aryl $(C_{1-20})$alkyl, hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$R$^6$R$^7$; —NO$_2$; —NR$^5$C(O)R$^4$; —NR$^5$S(O)R$^4$; NR$^5$C(O)NR$^6$R$^7$; NR$^6$R$^7$; cyano; —CO$_2$R$^5$; —C(O)NR$^6$R$^7$; and —C(O)R$^4$; and wherein the ratio R is less than, or equal to 1 (R≤1), where R=(sum (functionality of compound Y (F$_Y$)×number of moles of compound Y (N$_Y$))/(sum (functionality of compound Z (F$_Z$)×number of moles of all molecules of compound Z (N$_Z$)):

$$R = \frac{\sum F_Y N_Y}{\sum F_Z N_Z} \leq 1;$$

wherein R$^1$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl $(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or S(O)$_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more Z$^1$;

each Z$^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl $(C_{1-20})$alkyl, hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$; NR$^5$C(O)$_2$NR$^6$R$^7$; NR$^6$R$^7$; cyano; —COR$^5$; —C(O)NR$^6$R$^7$; and —C(O)R$^4$; and wherein R$_2$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenid), or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero $(C_{1-20})$alkyl; heterocyclyl; heteroaryl; $(C_{3-8})$cycloalkyl $(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or S(O);

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more Z$^1$;

each Z$^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl $(C_{1-20})$alkyl hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl; halo$(C_{1-20})$alkyloxy; —OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$; NR$^5$C(O)$_2$NR$^6$R$^7$; NR$^6$R$^7$; cyano; —COR$^5$; —C(O)NR$^6$R$^7$; and —C(O)R$^4$; and wherein R$^2$ and R$^3$ are optionally directly bonded together to form a, 5 membered cycloalkyl, heterocyclyl, or heteroaryl;

wherein R$^2$ and R$^3$ are optionally bonded together with a linker X$^1$ to form a 6, 7, or 8 membered cycloalkyl, heterocyclyl, or heteroaryl;

wherein X$^1$ within said cycloalkyl, heterocyclyl, or heteroaryl is independently selected from the group consisting of C, Si, chalcogenide, or a pnictide;

wherein each said heterocyclyl; or heteroaryl is independently optionally substituted with one or more Z$^2$ wherein each Z$^2$ is independently selected from the following group consisting of halogen; $(C_{1-20})$alkyl; $(C_{2-20})$alkenyl$(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl halo $(C_{1-20})$alkyl; halo$(C_{1-20})$alkyloxy; —OR$^5$; —SR$^5$; —S(O)R$^4$; —S(O)$_2$R$^4$; —SO$_2$NR$^5$R$^6$; nitro; —NR$^5$C(O)R$^4$; —NR$^5$S(O)R$^4$, —NR$^5$C(O)NR$^6$R$^7$, NR$^6$R$^7$; cyano; —CO$_2$R$^5$; —C(O)NR$^6$R$^7$; and —C(O)R$^4$;

wherein R$^2$ and R$^1$ are optionally directly bonded together to form a, 5 membered cycloalkyl, heterocyclyl, or heteroaryl;

wherein R$^2$ and R$^1$ are optionally bonded together with a linker X$^1$ to form a 6, 7, or 8 membered cycloalkyl, heterocyclyl, or heteroaryl;

wherein X$^1$ within said cycloalkyl, heterocyclyl, or heteroaryl is independently selected from the group consisting of C, Si, chalcogenide, or a pnictide;

wherein X$^1$ and R$^2$ are optionally directly bonded together to form a, 5, 6, 7, or 8 membered heterocyclyl, or heteroaryl;

wherein X$^1$ and R$^3$ are optionally directly bonded together to form a, 5, 6, 7, or 8 membered cycloalkyl, heterocyclyl, or heteroaryl;

wherein each said heterocyclyl; or heteroaryl is optionally substituted with one or more Z$^2$ where each Z$^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl $(C_{1-20})$alkyl, hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl;

halo($C_{1-20}$)alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)R^4$; —$NR^5C(O)NR^6R^7$; $NR^6R^7$; cyano; —$CO_2R^3$; —$C(O)NR^6R^7$; and —$C(O)R^4$;

wherein $R_3$ is selected from the group consisting of ($C_{1-20}$)alkyl, ($C_{2-20}$)alkenyl; ($C_{2-20}$)alkynyl; ($C_{6-12}$)aryl, ($C_{3-8}$)cycloalkyl; ($C_{6-12}$)aryl($C_{1-20}$)alkyl; ($C_{3-8}$)cycloalkyl($C_{1-20}$)alkyl; hetero($C_{1-20}$)alkyl; heterocyclyl; heterocyclyl($C_{1-20}$)alkyl; heteroaryl; and heteroaryl($C_{1-20}$)alkyl;

wherein said ($C_{1-20}$)alkyl, ($C_{2-20}$)alkenyl, ($C_{2-20}$)alkynyl, ($C_{3-8}$)cycloalkyl($C_{1-20}$)alky); ($C_{6-12}$)aryl($C_{1-20}$)alkyl, heterocyclyl($C_{1-20}$)alkyl; and heteroaryl($C_{1-20}$)alkyl, optionally comprises one or more heteroatoms in the alkyl, alkenyl, alkynyl moiety, each heteroatom is independently a C, Si, chalcogenide, or a pnictide;

wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; and heteroaryl($C_{1-20}$)alkyl; is optionally oxidized to form at least one C=O, C=S, N=O, N=S, S=O or S(O);

wherein said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; and heteroaryl($C_{1-20}$)alkyl; is unsubstituted or substituted with one or more $Z^1$;

wherein each $Z^1$ is independently selected from the group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$; —$S(O)_2R^4$; —$SO_2NR^6R^7$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and $C(O)R^4$; and wherein $R^3$ and $R^1$ are optionally directly bonded together to form a, 5 membered cycloalkyl, heterocyclyl, or heteroaryl;

wherein $R^3$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Se), or a pnictide (such as N, or P);

wherein each said heterocyclyl; or heteroaryl is optionally substituted with one or more $Z^2$ where each $Z^2$ is independently selected from the following group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)_2R^4$, —$NR^5C(O)NR^6R^7$; $NR^6R^7$; cyano; —$CO_2R^5$; —$C(O)NR^6R^7$; and —$C(O)R^4$;

wherein $R^3$ is linked to $R^1$ with a linker $X^1$ to form a 4, 5, 6, or 7 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is optionally substituted with one or more $Z^2$ where each $Z^2$ is independently selected from the following group consisting of halogen; ($C_{1-20}$)alkyl; ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; ($C_{3-8}$)cycloalkyl($C_{1-20}$)alkyl; heterocyclyl($C_{1-20}$)alkyl; heteroaryl($C_{1-20}$)alkyl; halo($C_{1-20}$)alkyl; halo($C_{1-20}$)alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)_2R^4$; —$NR^5C(O)NR^6R^7$; $NR^6R^7$; cyano; —$CO_2R^5$; —$C(O)NR^6R^7$; and —$C(O)R^4$;

each $R^4$ is independently selected from the group consisting of hydrogen, $C_{(1-20)}$alkyl, $C_{(2-20)}$alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{6-12}$)aryl($C_{1-20}$)alkyl, heterocyclyl($C_{1-20}$)alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^5$ is independently selected from the group consisting of hydrogen, ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{6-12}$)aryl($C_{1-20}$)alkyl, heterocyclyl($C_{1-20}$)alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^6$ and $R^7$ is independently selected from the group consisting of hydrogen; ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{3-8}$)cycloalkyl($C_{1-20}$)alkyl; ($C_{6-12}$)aryl($C_{1-20}$)alkyl, heterocyclyl($C_{1-20}$)alkyl; and heteroaryl($C_{1-20}$)alkyl, optionally comprises one or more heteroatoms in the alkyl, alkenyl, alkynyl moiety, each heteroatom is independently a C, Si, chalcogenide, or a pnictide;

and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

or wherein $R^6$ and $R^7$ together with the atom to which they are attached form a 5-, 6-, or 7-membered heterocyclyl.

3. A method for synthesizing a polymer by melting one or more solid precursors, said method comprising:
- (c) melting one or more precursors together to form a polymer, wherein at least one precursor is solid prior to melting;
- (d) optionally mixing the one or more precursors are solids prior to, during, and/or subsequent to the melting step, or melting the precursors which are solid are optionally first melted individually then mixed together to form a polymer;

wherein optionally the melting of the one or more precursors is in a single or twin screw compound extrusion device;

wherein said polymer has at least one unit of the formula (I), (II), (III), (IV), (V), (VI), (VII), (VIII), (IX), (X), (XI), (XII), (XIII), (XIV), (XV), (XVI), (XVII), (XVIII), (XIX), and/or (XX), or a mixture thereof;

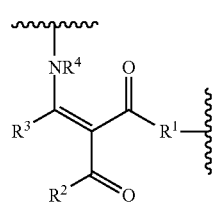
(I)

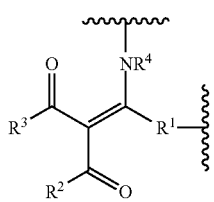
(II)

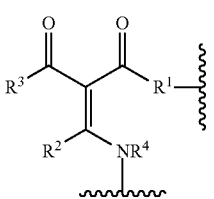
(III)

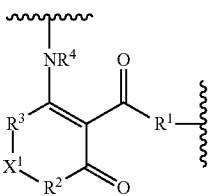
(IV)

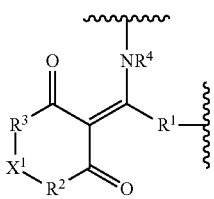
(V)

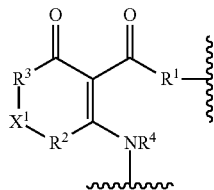
(VI)

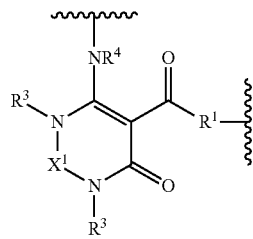
(VII)

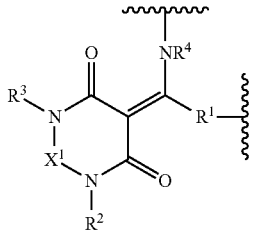
(VIII)

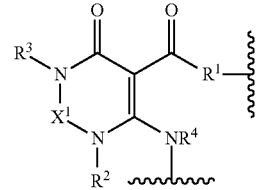
(IX)

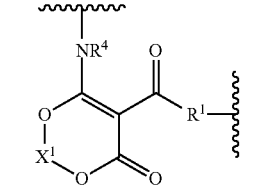
(X)

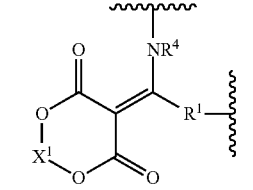
(XI)

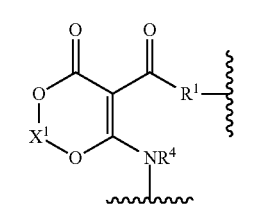
(XII)

-continued
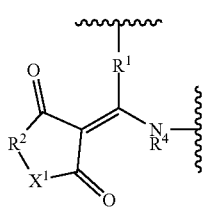
(XIII)
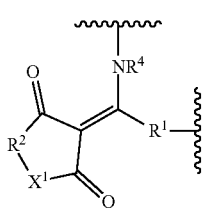
(XIV)
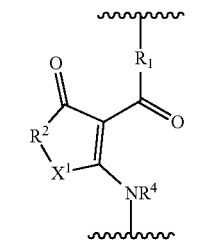
(XV)
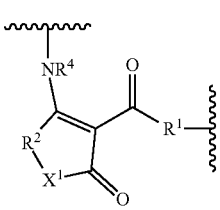
(XVI)
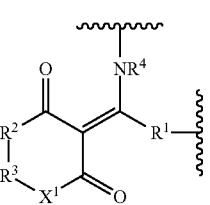
(XVII)
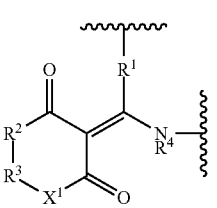
(XVIII)
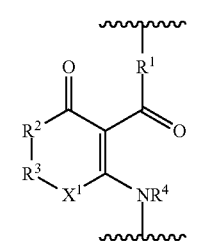
(XIX)
-continued
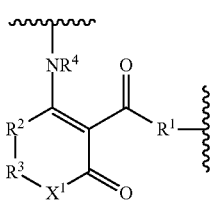
(XX)
wherein said polymer, or polymer network, is obtained by connecting one compound Y comprising at least two functional groups selected from the group (A), (B), (C), (D), (E), (F), (G), (H), (I), (J), (K), (L), (M), (N), (O), (P), (Q), (R), (S), (T), (U), (V), and/or (W), or a mixture thereof;
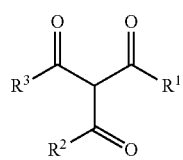
(A)
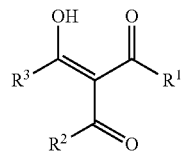
(B)
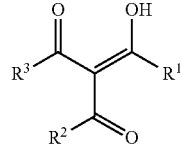
(C)
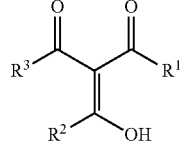
(D)
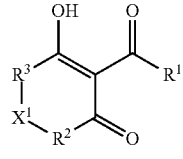
(E)
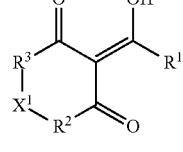
(F)
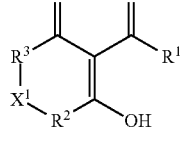
(G)

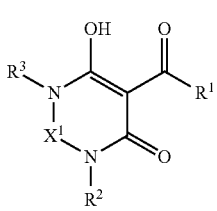 (H)

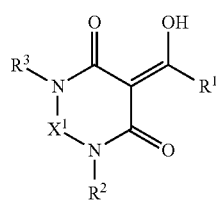 (I)

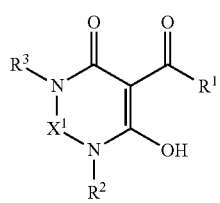 (J)

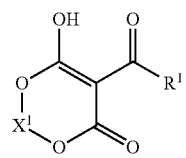 (K)

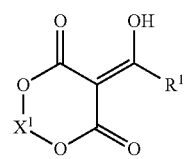 (L)

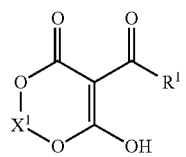 (M)

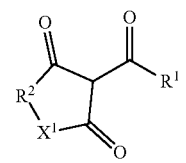 (N)

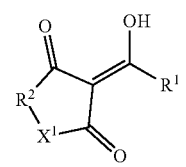 (O)

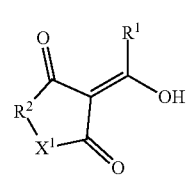 (P)

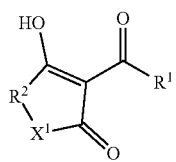 (Q)

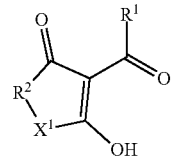 (R)

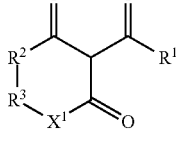 (S)

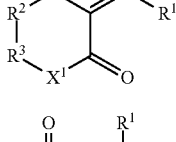 (T)

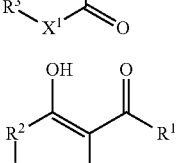 (U)

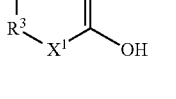 (V)

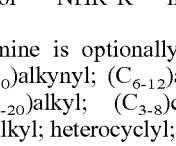 (W)

with at least one compound Z comprising at least two amine functional groups of the type —$NH_2$, —$NHR^4$, —$NH_3^+$ and/or —$NHR^4R^{5+}$ groups, or at least two functional groups that generates —$NH_2$, —$NHR^4$, —$NH_3^+$ and/or —$NHR^4R^{5+}$ in situ, or a mixture thereof;

wherein said amine is optionally $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; or heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl, moiety, said heteroatoms being each independently a C, Si, chalcogenide, or a pnictide;

wherein at least one carbon atom or heteroatom of said $(C_{1-20})$alkyl, $(C_{2-20})$alkenyl, $(C_{2-20})$alkynyl, $(C_{6-12})$ aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; can optionally be oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; can be unsubstituted or substituted with one or more $Z^1$;

each $Z^1$ is independently selected from the group consisting of halogen: $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^6R^7$; —$NO_2$; —$NR^5C(O)R^4$; —$NR_5S(O)_2R^4$; —$NR^5C(O)NR^6R^7$; $NR^6R^7$; cyano; —$CO_2R^5$; —$C(O)NR^6R^7$; and —$C(O)R^4$; and wherein the ratio R is less than, or equal to 1 (R≤1), where R=(sum (functionality of compound Y ($F_Y$)×number of moles of compound Y ($N_Y$))/(sum (functionality of compound Z ($F_Z$)×number of moles of all molecules of compound Z ($N_Z$)):

$$R = \frac{\sum F_Y N_Y}{\sum F_Z N_Z} \leq 1;$$

wherein $R_1$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^6R^7$; nitro; —$NR^5C(O)R^4$;

—$NR^5S(O)_2R_4$; —$NR^5C(O)NR^6R^7$, $NR^6R^7$; cyano; —$CO_2R^5$; —$C(O)NR^6R^7$; and —$C(O)R^4$; and wherein $R_2$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenid), or a pnictid);

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; can be oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-2})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and/or heteroaryl$(C_{1-20})$alkyl; is unsubstituted or substituted with one or more $Z^1$;

each $Z^1$ is independently selected from the group consisting of halogen: $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^6R^7$; nitro; —$NR^5C(O)R^4$; —$NR_5S(O)_2R^4$; $NR^5C(O)NR^6R^7$; $NR^6R^7$; cyano; —$CO_2R^5$; —$C(O)NR^6R^7$; and —$C(O)R^4$; and wherein $R^2$ and $R^3$ are optionally directly bonded together to form a, 5 membered cycloalkyl, heterocyclyl, or heteroaryl;

wherein $R^2$ and $R^3$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is independently optionally substituted with one or more $Z^2$ wherein each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; —$OR^5$; —$SR^5$; —$S(O)R^4$; —$S(O)_2R^4$; —$SO_2NR^5R^6$; nitro; —$NR^5C(O)R^4$; —$NR^5S(O)_2R^4$, —$NR^5C(O)$ $NR^6R^7$; $NR^6R^7$; cyano; —$CO_2R^5$; —$C(O)NR^6R^7$; and —$C(O)R^4$;

wherein $R^2$ and $R^1$ are optionally directly bonded together to form a, 5 membered cycloalkyl, heterocyclyl, or heteroaryl;

wherein $R^2$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein $X^1$ and $R^2$ are optionally directly bonded together to form a, 5, 6, 7, or 8 membered heterocyclyl, or heteroaryl;

wherein $X^1$ and $R^3$ are optionally directly bonded together to form a, 5, 6, 7, or 8 membered cycloalkyl, heterocyclyl, or heteroaryl;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $-NR^5C(O)R^4$; $-NR^5S(O)_2R^4$, $-NR^5C(O)NR^6R^7$, $NR^6R^7$; cyano; $-CO_2R^5$; $C(O)NR^6R^7$; and $-C(O)R^4$;

wherein $R^3$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero $(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictide;

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is optionally oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is unsubstituted or substituted with one or more $Z^1$;

wherein each $Z^1$ is independently selected from the group consisting of halogen; $(C_{1-20})$alkyl; $(C_{2-20})$alkenyl, $(C_{2-20})$alkynyl, $(C_{6-12})$aryl$(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)R^4$; $-SO_2NR^6R^7$; nitro; $NR^5C(O)R^4$; $-NR^5S(O)_2R^4$; $-NR^5C(O)NR^6R^7$, $NR^6R^7$; cyano; $-CO_2R_5$; $-C(O)NR^6R^7$; and $-C(O) R^4$; and wherein $R^3$ and $R^1$ are optionally directly bonded together to form a, 5 membered cycloalkyl, heterocyclyl, or heteroaryl;

wherein $R^3$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Se), or a pnictide (such as N, or P);

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $-NR^5C(O)R^4$; $-NR^5S(O)_2R^4$; $-NR^5C(O)NR^6R^7$, $NR^6R^7$; cyano; $-CO_2R^5$; $-C(O)NR^6R^7$; and $-C(O)R^4$ wherein $R^3$ is linked to $R^1$ with a linker $X^1$ to form a 4, 5, 6, or 7 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl$(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $-NR^5C(O)R^4$; $-NR^5S(O)_2R^4$; $-NR^5C(O)NR^6R^7$; $NR^6R^7$; cyano; $-CO_2R^5$; $-C(O)NR^6R^7$; and $-C(O)R^4$;

each $R^4$ is independently selected from the group consisting of hydrogen, $C_{(1-20)}$alkyl, $C_{(2-20)}$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{6-12})$aryl$(C_{1-20})$alkyl, heterocyclyl$(C_{1-20})$alkyl; heteroaryl$(C_{1-20})$alkyl, optionally comprise one or more heteroatoms in the alkyl, alkenyl or alkynyl moiety, said heteroatoms being each independently selected from O, S and N; and wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; is optionally oxidized to form at least one C=O, C=S, N=O, N=S, S=O or $S(O)_2$;

each $R^5$ is independently selected from the group consisting of hydrogen, $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{6-12})$aryl$(C_{1-20})$alkyl, heterocyclyl$(C_{1-20})$alkyl; heteroaryl$(C_{1-20})$alkyl, optionally comprise one or more heteroatoms in the alkyl, alkenyl or alkynyl moiety, said heteroatoms being each independently selected from O, S and N; and wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl; is optionally oxidized to form at least one C=O, C=S, N=O, N=S, S=O or $S(O)_2$;

each $R^6$ and $R^7$ is independently selected from the group consisting of hydrogen; $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl moiety, each heteroatom is independently a C, Si, chalcogenide, or a pnictide;

and wherein at least one carbon atom or heteroatom of said (C$_{1-20}$)alkyl, (C$_{2-20}$)alkenyl(C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; heterocyclyl(C$_{1-20}$)alkyl; and heteroaryl(C$_{1-20}$)alkyl; is optionally oxidized to form at least one C═O, C═S, N═O, N═S, S═O or S(O)$_2$;

or wherein R$^6$ and R$^7$ together with the atom to which they are attached form a 5-, 6-, or 7-membered heterocyclyl.

4. A method for synthesizing a polymer from one or more precursors using mechanical grinding, said method comprising:

mixing one or more said precursors together in a shaking or rotating chamber to form a polymer;

wherein said shaking or rotating chamber is optionally a ball mill, wherein optionally said shaking or rotating chamber contains a grinding medium;

wherein said grinding medium optionally comprises of one or several sizes of spheres or rods made of metallic, composite, ceramic, or polymer materials;

wherein said precursors are optionally dissolved in a solvent prior to mechanical grinding in said rotating chamber, also optionally called a ball mill;

wherein said precursors are optionally mixed together in a solvent during mechanical grinding;

wherein if one or more precursors are solids, precursors are optionally melted together before mixing;

wherein the duration of mixing of precursors within said shaking or rotating chamber, optionally with said grinding medium, is used to control the extent of polymerization;

wherein the duration of mixing of said precursors within said shaking or rotating chamber is used to control polymer properties;

wherein said polymer properties may optionally include the glass transition temperature (T$_g$), polymer solubility, modulus, tensile strength, polymer color, polymer toughness, polymer rigidity;

wherein said polymer has at least one unit of the formula (I), (II), (III), (IV), (V), (VI), (VII), (VIII), (IX), (X), (XI), (XII), (XIII), (XIV), (XV), (XVI), (XVII), (XVIII), (XIX), and/or (XX), or a mixture thereof;

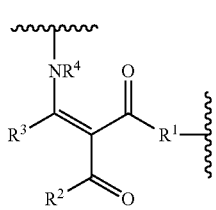

(I)

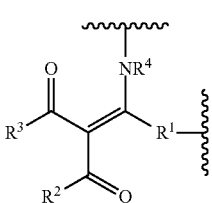

(II)

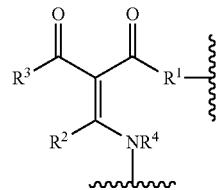

(III)

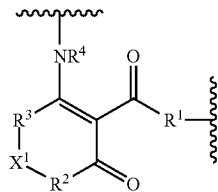

(IV)

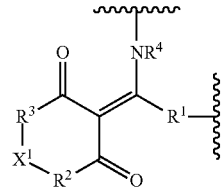

(V)

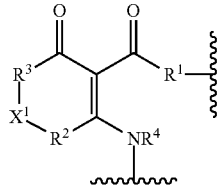

(VI)

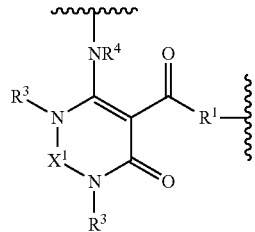

(VII)

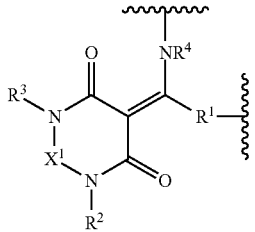

(VIII)

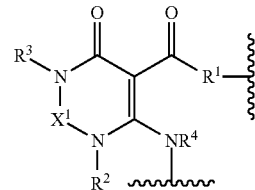

(IX)

(X)
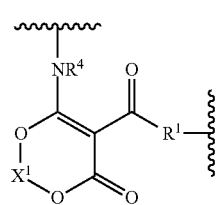
(XI)
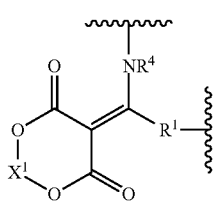
(XII)
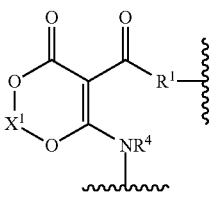
(XIII)
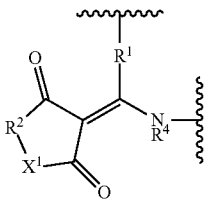
(XIV)
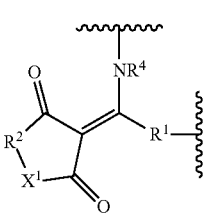
(XV)
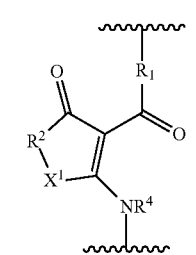
(XVI)
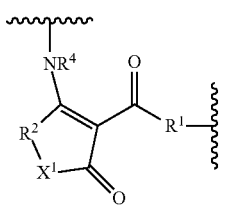
(XVII)
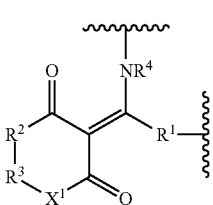
(XVIII)
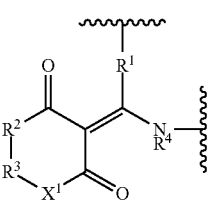
(XIX)
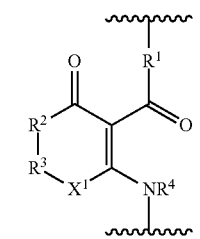
(XX)
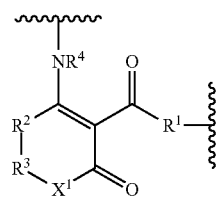
wherein said polymer, or polymer network, is obtained by connecting one compound Y comprising at least two functional groups selected from the group (A), (B), (C), (D), (E), (F), (G), (H), (I), (J), (K), (L), (M), (N), (O), (P), (Q), (R), (S), (T), (U), (V), and/or (W), or a mixture thereof;
(A)
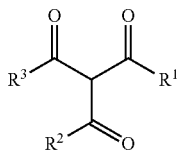
(B)
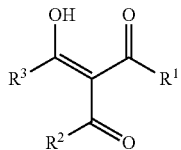
(C)
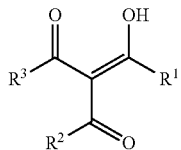

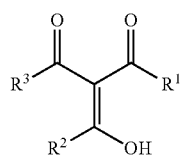 (D)
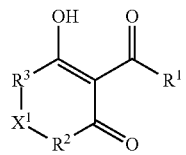 (E)
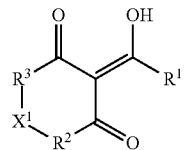 (F)
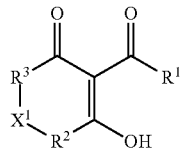 (G)
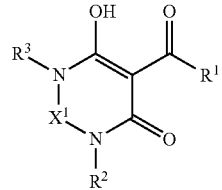 (H)
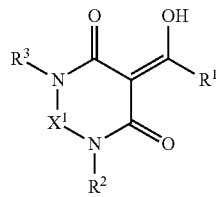 (I)
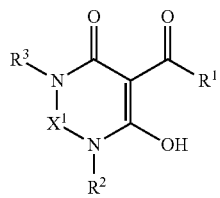 (J)
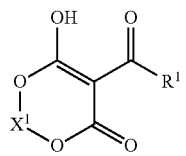 (K)
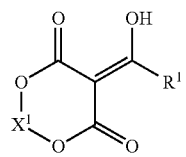 (L)
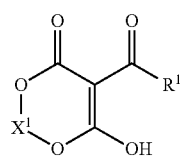 (M)
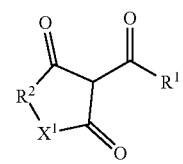 (N)
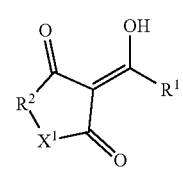 (O)
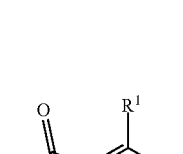 (P)
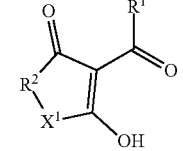 (Q)
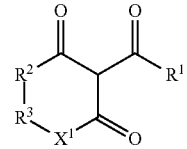 (R)
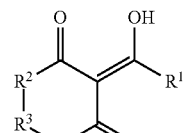 (S)
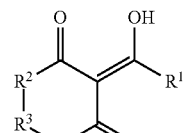 (T)
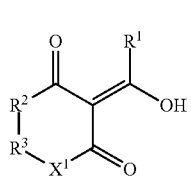 (U)

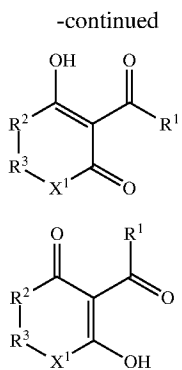

with at least one compound Z comprising at least two amine functional groups of the type —NH$_2$, —NHR$^4$, —NH$_3^+$ and/or —NHR$^4$R$^{5+}$ groups, or at least two functional groups that generates —NH$_2$, —NHR$^4$, —NH$_3^+$ and/or —NHR$^4$R$^{5+}$ in situ, or a mixture thereof;

wherein said amine is optionally (C$_{1-20}$)alkyl, (C$_{2-20}$)alkenyl, (C$_{2-20}$)alkynyl, (C$_{6-12}$)aryl(C$_{3-8}$)cycloalkyl; (C$_{6-12}$)aryl(C$_{1-20}$)alkyl; (C$_{3-8}$)cycloalkyl(C$_{1-20}$)alkyl; hetero(C$_{1-20}$)alkyl; heterocyclyl; heterocyclyl(C$_{1-20}$)alkyl; heteroaryl; or heteroaryl(C$_{1-20}$)alkyl; wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl, moiety, said heteroatoms being each independently a C, Si, chalcogenide, or a pnictide;

wherein at least one carbon atom or heteroatom of said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero (C$_{1-20}$)alkyl; heterocyclyl; heteroaryl; (C$_{3-8}$)cycloalkyl (C$_{1-20}$)alkyl; heterocyclyl(C$_{1-20}$)alkyl; and heteroaryl (C$_{1-20}$)alkyl; can optionally be oxidized to form at least one C=O, C=S, N=O, N=S, S=O or S(O)$_2$;

wherein said (C$_{1-20}$)alkyl, (C$_{2-20}$)alkenyl, (C$_{2-20}$)alkynyl, (C$_{6-12}$)aryl, (C$_{3-8}$)cycloalkyl; (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and heteroaryl(C$_{1-20}$)alkyl; can be unsubstituted or substituted with one or more Z$^1$;

each Z$^1$ is independently selected from the group consisting of halogen: (C$_{1-20}$)alkyl; (C$_{2-20}$)alkenyl, (C$_{2-20}$) alkynyl, (C$_{6-12}$)aryl, (C$_{3-8}$)cycloalkyl, (C$_{6-12}$)aryl (C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl (C$_{1-20}$)alkyl; heteroaryl(C$_{1-20}$)alkyl; halo(C$_{1-20}$)alkyl; halo(C$_{1-20}$)alkyloxy; OR$^5$; —SR$^5$; —S(O)R$^4$; —S(O)$_2$ R$^4$; —SO$_2$NR$^6$R$^7$; —NO$_2$; —NR$^5$C(O)R$^4$; —NR$^5$S (O)$_2$ R$^4$; —NR$^5$C(O)NR$^6$R$^7$; NR$^6$R$^7$; cyano; —CO$_2$R$^5$; —C(O)NR$^6$R$^7$; and —C(O)R$^4$, and wherein the ratio R is less than, or equal to 1 (R≤1), where R=(sum (functionality of compound Y (F$_Y$)×number of moles of compound Y (N$_Y$))/(sum (functionality of compound Z (F$_Z$)×number of moles of all molecules of compound Z (N$_Z$)):

$$R = \frac{\sum F_Y N_Y}{\sum F_Z N_Z} \le 1;$$

wherein R$_{ii}$s is selected from the group consisting of (C$_{1-20}$)alkyl, (C$_{2-20}$)alkenyl; (C$_{2-20}$)alkynyl; (C$_{6-12}$) aryl, (C$_{3-8}$)cycloalkyl; (C$_{6-12}$)aryl(C$_{1-20}$)alkyl; (C$_{3-8}$) cycloalkyl(C$_{1-20}$)alkyl; hetero(C$_{1-20}$)alkyl; heterocyclyl; heterocyclyl(C$_{1-20}$)alkyl; heteroaryl; and heteroaryl(C$_{1-20}$)alkyl;

wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl moiety, each heteroatom is independently a C, Si, chalcogenide, or a pnictid);

wherein at least one carbon atom or heteroatom of said (C$_{1-20}$)alkyl, (C$_{2-20}$)alkenyl, (C$_{2-20}$)alkynyl, (C$_{6-12}$) aryl, (C$_{3-2}$)cycloalkyl, (C$_{6-12}$)aryl(C$_{1-20}$)alkyl, hetero (C$_{1-20}$)alkyl; heterocyclyl; heteroaryl; (C$_{3-8}$)cycloalkyl (C$_{1-20}$)alkyl; heterocyclyl(C$_{1-20}$)alkyl; and/or heteroaryl(C$_{1-20}$)alkyl; can be oxidized to form at least one C=O, C=S, N=O, N=S, S=O or S(O)$_2$;

wherein said (C$_{1-20}$)alkyl, (C$_{2-20}$)alkenyl, (C$_{2-20}$)alkynyl, (C$_{6-12}$)aryl, (C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and/or heteroaryl(C$_{1-20}$)alkyl; is unsubstituted or substituted with one or more Z$^1$;

each Z$^1$ is independently selected from the group consisting of halogen; (C$_{1-20}$)alkyl; (C$_{2-20}$)alkenyl, (C$_{2-20}$) alkynyl, (C$_{6-12}$)aryl, (C$_{3-8}$)cycloalkyl, (C$_{6-12}$)aryl (C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl (C$_{1-20}$)alkyl; heteroaryl(C$_{1-20}$)alkyl; halo(C$_{1-20}$)alkyl; halo(C$_{1-20}$)alkyloxy; —OR$^5$; —SR$^5$; —S(O)R$^4$; —S(O)$_2$R$^4$; —SO$_2$NR$^6$R$^7$; nitro; —NR$^5$C(O)R$^4$; —NR$^5$S(O)$_2$R$^4$; —NR$^5$C(O) NR$^6$R$^7$; NR$^6$R$^7$; cyano; —CO$_2$R$^5$; —C(O)NR$^6$R$^7$; and —C(O)R$^4$; and wherein R$^2$ is selected from the group consisting of (C$_{1-20}$)alkyl, (C$_{2-20}$)alkenyl; (C$_{2-20}$)alkynyl; (C$_{6-12}$) aryl, (C$_{3-8}$)cycloalkyl; (C$_{6-12}$)aryl(C$_{1-20}$)alkyl; (C$_{3-8}$) cycloalkyl(C$_{1-20}$)alkyl; hetero(C$_{1-20}$)alkyl; heterocyclyl; heterocyclyl(C$_{1-20}$)alkyl; heteroaryl; and heteroaryl(C$_{1-20}$)alkyl;

wherein said (C$_{1-20}$)alkyl, (C$_{2-20}$)alkenyl, (C$_{2-20}$)alkynyl, (C$_{3-8}$)cycloalkyl(C$_{1-20}$)alkyl; (C$_{6-12}$)aryl(C$_{1-20}$)alkyl, heterocyclyl(C$_{1-20}$)alkyl; and heteroaryl(C$_{1-20}$)alkyl, optionally comprises one or more heteroatoms in the alkyl, alkenyl, alkynyl moiety each heteroatom is independently a C, Si, chalcogenid), or a pnictid);

wherein at least one carbon atom or heteroatom of said (C$_{1-20}$)alkyl, (C$_{2-20}$)alkenyl, (C$_{2-20}$)alkynyl, (C$_{6-12}$) aryl, (C$_{3-8}$)cycloalkyl, (C$_{6-12}$)aryl(C$_{1-20}$)alkyl, hetero (C$_{1-20}$)alkyl; heterocyclyl; heteroaryl; (C$_{3-8}$)cycloalkyl (C$_{1-20}$)alkyl; heterocyclyl(C$_{1-20}$)alkyl; and/or heteroaryl(C$_{1-20}$)alkyl; can be oxidized to form at least one C=O, C=S, N=O, N=S, S=O or S(O)$_2$;

wherein said (C$_{1-20}$)alkyl, (C$_{2-20}$)alkenyl, (C$_{2-20}$)alkynyl, (C$_{6-12}$)aryl(C$_{3-8}$)cycloalkyl, (C$_{6-12}$)aryl(C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl(C$_{1-20}$)alkyl; and/or heteroaryl(C$_{1-20}$)alkyl; is unsubstituted or substituted with one or more Z$^1$;

each Z$^1$ is independently selected from the group consisting of halogen: (C$_{1-20}$)alkyl; (C$_{2-20}$)alkenyl, (C$_{2-20}$) alkynyl, (C$_{6-12}$)aryl, (C$_{3-8}$)cycloalkyl, (C$_{6-12}$)aryl (C$_{1-20}$)alkyl, hetero(C$_{1-20}$)alkyl; heterocyclyl; heteroaryl; (C$_{3-8}$)cycloalkyl(C$_{1-20}$)alkyl; heterocyclyl (C$_{1-20}$)alkyl; heteroaryl(C$_{1-20}$)alkyl; halo(C$_{1-20}$)alkyl; halo(C$_{1-20}$)alkyloxy; OR$^5$; —SR$^5$; —S(O)R$^4$; —

$S(O)_2R^4$; $-SO_2NR^6R^7$; nitro; $-NR^5C(O)R^4$; $-NR^5S(O)_2R^4$; $-NR^5C(O)NR^6R^7$; $NR^6R^7$; cyano; $-CO_2R^5$; $-C(O)NR^6R^7$; and $-C(O)R^4$; and wherein $R^2$ and $R^3$ are optionally directly bonded together to form a, 5 membered cycloalkyl, heterocyclyl, or heteroaryl;

wherein $R^2$ and $R^3$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is independently optionally substituted with one or more $Z^2$ wherein each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$ cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $-NR^5C(O)R^4$; $-NR^5S(O)_2R^4$; $-NR^5C(O)NR^6R^7$, $NR^6R^7$; cyano; $-CO_2R^5$; $-C(O)NR^6R^7$; and $-C(O)R^4$;

wherein $R^2$ and $R^1$ are optionally directly bonded together to form a, 5 membered cycloalkyl, heterocyclyl, or heteroaryl;

wherein $R^2$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein $X^1$ and $R^2$ are optionally directly bonded together to form a, 5, 6, 7, or 8 membered heterocyclyl, or heteroaryl;

wherein $X^1$ and $R^3$ are optionally directly bonded together to form a, 5, 6, 7, or 8 membered cycloalkyl, heterocyclyl, or heteroaryl;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl $(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $NR^5C(O)R^4$; $-NR^5(O)_2R^4$, $-NR^5C(O)NR^6R^7$, $NR^6R^7$; cyano; $-CO_2R^5$; $-C(O)NR^6R^7$; and $C(O)R^4$;

wherein $R^3$ is selected from the group consisting of $(C_{1-20})$alkyl, $(C_{2-20})$alkenyl; $(C_{2-20})$alkynyl; $(C_{6-12})$aryl, $(C_{3-8})$cycloalkyl; $(C_{6-12})$aryl$(C_{1-20})$alkyl; $(C_{3-8})$cycloalkyl$(C_{1-20})$alkyl; hetero$(C_{1-20})$alkyl; heterocyclyl; heterocyclyl$(C_{1-20})$alkyl; heteroaryl; and heteroaryl$(C_{1-20})$alkyl;

wherein said $(C_{1-20})$alkyl, $(C_{2-20})$alkenyl, $(C_{2-20})$alkynyl, $(C_{3-8})$cycloalkyl$(C_{1-20})$alkyl; $(C_{6-12})$aryl$(C_{1-20})$alkyl, heterocyclyl$(C_{1-20})$alkyl; and heteroaryl$(C_{1-20})$alkyl, optionally comprises one or more heteroatoms in the alkyl, alkenyl, alkynyl moiety, each heteroatom is independently a C, Si, chalcogenide, or a pnictide;

wherein at least one carbon atom or heteroatom of said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is optionally oxidized to form at least one C=O, C=S, N=O, N=S, S=O or $S(O)_2$;

wherein said $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; and heteroaryl$(C_{1-20})$alkyl; is unsubstituted or substituted with one or more $Z^1$;

wherein each $Z^1$ is independently selected from the group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^6R^7$; nitro; $-NR^5C(O)R^4$;— $NR^5S(O)_2R^4$; $-NR^5C(O)$ $NR^6R^7$; $NR^6R^7$; cyano; $-CO_2R^5$; $-C(O)_2NR^6R^7$; and $C(O)R^4$; and wherein $R^3$ and $R^1$ are optionally directly bonded together to form a, 5 membered cycloalkyl, heterocyclyl, or heteroaryl;

wherein $R^3$ and $R^1$ are optionally bonded together with a linker $X^1$ to form a 6, 7, or 8 membered cycloalkyl, heterocyclyl, or heteroaryl;

wherein $X^1$ within said cycloalkyl, heterocyclyl, or heteroaryl is independently selected from the group consisting of C, Si, chalcogenide (such as O, S, or Se), or a pnictide (such as N, or P);

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl, $(C_{6-12})$aryl $(C_{1-20})$alkyl, hetero$(C_{1-20})$alkyl; heterocyclyl; heteroaryl; $(C_{3-8})$cycloalkyl$(C_{1-20})$alkyl; heterocyclyl $(C_{1-20})$alkyl; heteroaryl$(C_{1-20})$alkyl; halo$(C_{1-20})$alkyl; halo$(C_{1-20})$alkyloxy; $-OR^5$, $-SR^5$; $-S(O)R^4$; $-S(O)_2R^4$; $-SO_2NR^5R^6$; nitro; $NR^5C(O)R^4$; $-NR^5(O)_2R^4$,—$NR^5C(O)$ $NR^6R^7$; $NR^6R^7$; cyano; $-CO_2R^7$; $-C(O)NR^6R^7$; and $-C(O)R^4$ wherein $R^3$ is linked to $R^1$ with a linker $X^1$ to form a 4, 5, 6, or 7 membered cycloalkyl, heterocyclyl, or heteroaryl;

wherein $X^1$ within said cycloalkyl, heterocyclyl, or heteroaryl is independently selected from the group consisting of C, Si, chalcogenide, or a pnictide;

wherein each said heterocyclyl; or heteroaryl is optionally substituted with one or more $Z^2$ where each $Z^2$ is independently selected from the following group consisting of halogen; $(C_{1-20})$alkyl; $(C_{2-20})$alkenyl, $(C_{2-20})$alkynyl, $(C_{6-12})$aryl, $(C_{3-8})$cycloalkyl$(C_{6-12})$aryl$(C_{1-20})$alkyl, hetero$(C_{1-20})$alkyl; heterocyclyl; heteroaryl; $(C_{3-8})$cycloalkyl$(C_{1-20})$alkyl; heterocyclyl$(C_{1-20})$alkyl; heteroaryl$(C_{1-20})$alkyl; halo$(C_{1-20})$alkyl; halo$(C_{1-20})$alkyloxy; $-OR^5$; $-SR^5$; $-S(O)R^4$; $-S(O)_2R^4$; $-SO_2NR^5R^6$; nitro; $-NR^5C(O)R^4$; $-NR^5S(O)_2R^4$; $-NR^5C(O)$ $NR^6R^7$; $NR^6R^7$; cyano; $-CO_2R^5$; $-C(O)NR^6R^7$; and $-C(O)R^4$;

each $R^4$ is independently selected from the group consisting of hydrogen, $C_{(1-20)}$alkyl, $C_{(2-20)}$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl; heterocyclyl; heteroaryl; heterocyclyl$(C_{1-20})$alkyl; and heteroaryl$(C_{1-20})$alkyl;

wherein said $(C_{1-20})$alkyl, $(C_{2-20})$alkenyl, $(C_{2-20})$alkynyl, $(C_{6-12})$aryl$(C_{1-20})$alkyl, heterocyclyl$(C_{1-20})$alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^5$ is independently selected from the group consisting of hydrogen, ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{6-12}$)aryl($C_{1-20}$)alkyl, heterocyclyl($C_{1-20}$)alkyl; heteroaryl($C_{1-20}$)alkyl, optionally comprise one or more heteroatoms in the alkyl, alkenyl or alkynyl moiety, said heteroatoms being each independently selected from O, S and N; and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

each $R^6$ and $R^7$ is independently selected from the group consisting of hydrogen; ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl;

wherein said ($C_{1-20}$)alkyl, ($C_{2-20}$)alkenyl, ($C_{2-20}$)alkynyl, ($C_{3-8}$)cycloalkyl($C_{1-20}$)alkyl; ($C_{6-12}$)aryl($C_{1-20}$)alkyl, heterocyclyl($C_{1-20}$)alkyl; and heteroaryl($C_{1-20}$)alkyl, optionally comprises one or more heteroatoms in the alkyl, alkenyl, alkynyl moiety, each heteroatom is independently a C, Si, chalcogenide, or a pnictide;

and wherein at least one carbon atom or heteroatom of said ($C_{1-20}$)alkyl, ($C_{2-20}$)alkenyl, ($C_{2-20}$)alkynyl, ($C_{6-12}$)aryl, ($C_{3-8}$)cycloalkyl, ($C_{6-12}$)aryl($C_{1-20}$)alkyl, hetero($C_{1-20}$)alkyl; heterocyclyl; heteroaryl; heterocyclyl($C_{1-20}$)alkyl; and heteroaryl($C_{1-20}$)alkyl; is optionally oxidized to form at least one C=O, C=S, N=O, N=S, S=O or S(O)$_2$;

or wherein $R^6$ and $R^7$ together with the atom to which they are attached form a 5-, 6-, or 7-membered heterocyclyl.

5. The composition of claim 1, wherein each chalcogenide is independently O, S, or Se.

6. The composition of claim 1, wherein each pnictide ius independently N or P.

* * * * *